US006787316B2

(12) United States Patent
Stewart et al.

(10) Patent No.: US 6,787,316 B2
(45) Date of Patent: Sep. 7, 2004

(54) DNA CLONING METHOD

(75) Inventors: Francis Stewart, Leimen (DE); Youming Zhang, Heidelberg (DE); Frank Buchholz, Bremen (DE)

(73) Assignee: Europaisches Laboratorium fur Molekularbiologie (EMBL), Heidelberg (DE)

( * ) Notice: Subject to any disclaimer, the term of this patent is extended or adjusted under 35 U.S.C. 154(b) by 0 days.

(21) Appl. No.: 10/231,013

(22) Filed: Aug. 30, 2002

(65) Prior Publication Data

US 2003/0036198 A1 Feb. 20, 2003

Related U.S. Application Data

(62) Division of application No. 09/555,510, filed as application No. PCT/EP98/07945 on Dec. 7, 1998, now Pat. No. 6,509,156.

(30) Foreign Application Priority Data

Dec. 5, 1997 (EP) ............................................ 97121462
Oct. 5, 1998 (EP) ............................................ 98118756

(51) Int. Cl.[7] ............................ C12Q 1/68; C12N 1/20; C12N 1/00; C12N 15/00; C12N 15/09; C12N 15/63; C12N 15/70; C12N 15/74
(52) U.S. Cl. ...................... 435/6; 435/252.3; 435/320.1
(58) Field of Search ........................ 435/6, 252.3, 320.1

(56) References Cited

FOREIGN PATENT DOCUMENTS

WO    WO 95/22625    8/1995

OTHER PUBLICATIONS

Hall, D. S. et al., "Homologous Pairing and strand exchange promoted by the *Escherichia coli* RecT protein", PNAS USA, vol. 91, pp. 3205–3209 (1994).
Oliner et al., "In vivo cloning of PCR Products in *E. coli* ", Nucleic Acids Research, vol. 21, No. 22, 1993, pp. 5192–5197.
Nussbaum et al., "Restriction–stimulated homologous recombination of plasmids by th RecE pathway of Escherichia coli", Genetics, vol. 130, No. 1, Jan. 1992, pp. 37–49.
Zhang et al., "A new logic for DNA engineering using recombination in *Escherichia coli*", Nature Genetics, vol. 20, No. 2, Oct. 1998, pp. 123–128.
Kolodner et al., "homologous paring proteins encoded by the *Escherichia coli* recE and recT genes" Molecular Microbiology, vol. 11, No. 1, 1994, pp. 23–30.
Luisi–Deluca et al., "Genetic and physical analysis of plasmid recombination in recB recC sbcB and recB recC sbcA *Escherichia coli* K–12 mutants", Genetics, vol. 122, 1989, pp. 269–278.
Degryse et al., "Evaluation of *Eschericia coli* recBC sbcBC mutants for cloning by recombination in vivo", Journal of Biotechnology, vol. 39, Apr. 16, 1995, pp. 181–187.
Yang et al., "Homologous recombination based modification in *Escherichia coli* and germ lline transmission in transgenic mice of a bacterial artificial chromosome", Nature Biotechnology, vol. 15, Sep. 1997, pp. 859–865.
Murphy, "Lambda Gam protein inhibits the helicase and Chl–stimulated recombination activities of *Escherichia coli* RecBCD enzyme", Journal of Bacteriology, vol. 173, No. 18, Sep. 1991, pp. 5808–5821.
GeneBank Accession No. V00638, "Lambda genome from map unit 74 backward to map unit 67" (1995).
Stratagena Catalog, p. 39 (1998).
Hall, S.D., et al., "Identification and Characterization of the *Escherichia coli* RecT Protein, a Protein Encoded by the recE Region That Promotes Resturation of Homologous Single–Stranded DNA", Journal of Bacteriology, Washington, D.C., vol. 175, No. 1, Jan. 1993, pp. 277–287.

*Primary Examiner*—Jeffrey Fredman
*Assistant Examiner*—Teresa Strzelecka
(74) *Attorney, Agent, or Firm*—Rothwell, Figg, Ernst & Manbeck, P.C.

(57) ABSTRACT

The invention relates to methods for cloning DNA molecules using recE/recT-mediated homologous recombination mechanism between at least two DNA molecules where one DNA molecule is a circular or linear DNA molecule and the second DNA molecule is a circular DNA molecule, and the second DNA molecule contains two regions with sequence homology to the first DNA molecule. Competent cells and vectors are also described.

29 Claims, 65 Drawing Sheets

Figure 1:
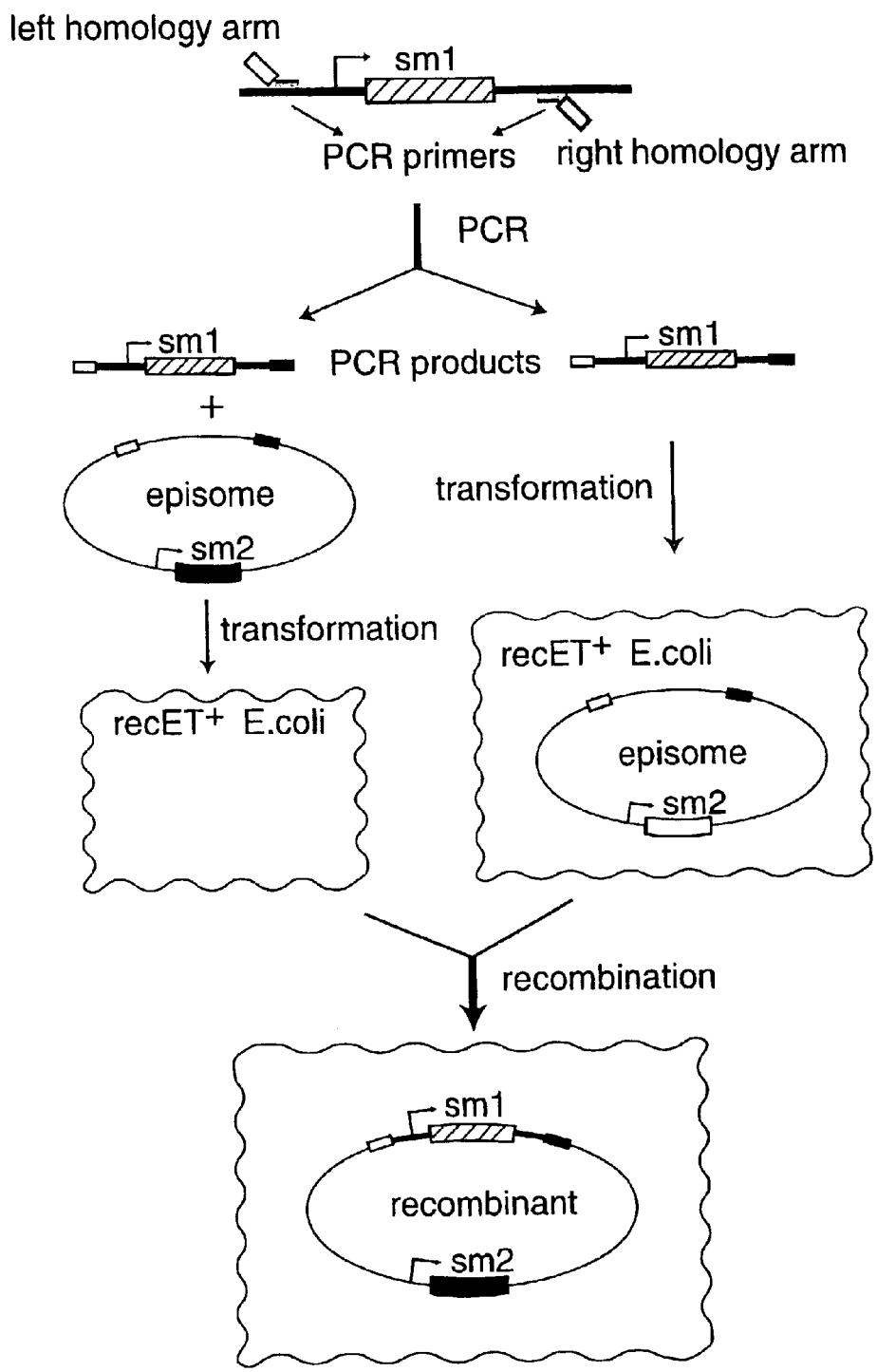

P1 DNA digested with EcoRI | hybridized with a bla probe (Amp) | hybridized with a Hoxa-1 probe Lane 1: 1 of p1-Hox clone in NS3145 original bacterial strain (Kan resistance)

Lane 2-3: 2 of p1-Hox cloned in JC9604 before homologous recombination *Kan resistance)

Lane 4-6: 3 of P1-Hox clones in JC9604 after homologous recombination (Amp resistance)

Pvu II digestion

IPTG + Kan

JC5547
(recA⁻, recB⁻, recC⁻)

+ t-recE---truncated recE (from 588 aa ---> end. 866 aa)

Fig.7b

```
  1 ATCGATGCATAATGTGCCTGTCAAATGGACGAAGCAGGGATTC

44 TGCAAACCCTATGCTACTCCGTCAAGCCGTCAATTGTCTGATT

87 CGTTACCAA TTA TGA CAA CTT GAC GGC TAC ATC
        293◀··· Ser Leu Lys Val Ala Val Asp

120 ATT CAC TTT TTC TTC ACA ACC GGC ACG GAA CTC
285◀Asn Val Lys Glu Glu Cys Gly Ala Arg Phe Glu

153 GCT CGG GCT GGC CCC GGT GCA TTT TTT AAA TAC
274◀Ser Pro Ser Ala Gly Thr Cys Lys Lys Phe Val

186 CCG CGA GAA ATA GAG TTG ATC GTC AAA ACC AAC
263◀Arg Ser Phe Tyr Leu Gln Asp Asp Phe Gly Val

219 ATT GCG ACC GAC GGT GGC GAT AGG CAT CCG GGT
252◀Asn Arg Gly Val Thr Ala Ile Pro Met Arg Thr

252 GGT GCT CAA AAG CAG CTT CGC CTG GCT GAT ACG
241◀Thr Ser Leu Leu Leu Lys Ala Gln Ser Ile Arg

285 TTG GTC CTC GCG CCA GCT TAA GAC GCT AAT CCC
230◀Gln Asp Glu Arg Trp Ser Leu Val Ser Ile Gly

318 TAA CTG CTG GCG GAA AAG ATG TGA CAG ACG CGA
219◀Leu Gln Gln Arg Phe Leu His Ser Leu Arg Ser

351 CGG CGA CAA GCA AAC ATG CTG TGC GAC GCT GGC
208◀Pro Ser Leu Cys Val His Gln Ala Val Ser Ala
    EcoRV
384 GAT ATC AAA ATT GCT GTC TGC CAG GTG ATC GCT
197◀Ile Asp Phe Asn Ser Asp Ala Leu His Asp Ser

417 GAT GTA CTG ACA AGC CTC GCG TAC CCG ATT ATC
186◀Ile Tyr Gln Cys Ala Glu Arg Val Arg Asn Asp
```

Fig.7c

```
450  CAT  CGG  TGG  ATG  GAG  CGA  CTC  GTT  AAT  CGC  TTC
175◄Met  Pro  Pro  His  Leu  Ser  Glu  Asn  Ile  Ala  Glu

483  CAT  GCG  CCG  CAG  TAA  CAA  TTG  CTC  AAG  CAG  ATT
164◄Met  Arg  Arg  Leu  Leu  Leu  Gln  Glu  Leu  Leu  Asn

516  TAT  CGC  CAG  CAG  CTC  CGA  ATA  GCG  CCC  TTC  CCC
153◄Ile  Ala  Leu  Leu  Glu  Ser  Tyr  Arg  Gly  Glu  Gly

549  TTG  CCC  GGC  GTT  AAT  GAT  TTG  CCC  AAA  CAG  GTC
142◄Gln  Gly  Ala  Asn  Ile  Ile  Gln  Gly  Phe  Leu  Asp

582  GCT  GAA  ATG  CGG  CTG  GTG  CGC  TTC  ATC  CGG  GCG
131◄Ser  Phe  His  Pro  Gln  His  Ala  Glu  Asp  Pro  Arg

615  AAA  GAA  CCC  CGT  ATT  GGC  AAA  TAT  TGA  CGG  CCA
120◄Phe  Phe  Gly  Thr  Asn  Ala  Phe  Ile  Ser  Pro  Trp

648  GTT  AAG  CCA  TTC  ATG  CCA  GTA  GGC  GCG  CGG  ACG
109◄Asn  Leu  Trp  Glu  His  Trp  Tyr  Ala  Arg  Pro  Arg

681  AAA  GTA  AAC  CCA  CTG  GTG  ATA  CCA  TTC  GCG  AGC
 98◄Phe  Tyr  Val  Trp  Gln  His  Tyr  Trp  Glu  Arg  Ala

714  CTC  CGG  ATG  ACG  ACC  GTA  GTG  ATG  AAT  CTC  TCC
 87◄Glu  Pro  His  Arg  Gly  Tyr  His  His  Ile  Glu  Gly

747  TGG  CGG  GAA  CAG  CAA  AAT  ATC  ACC  CGG  TCG  GCA
 76◄Pro  Pro  Phe  Leu  Leu  Ile  Asp  Gly  Pro  Arg  Cys

780  AAC  AAA  TTC  TCG  TCC  CTG  ATT  TTT  CAC  CAC  CCC
 65◄Val  Phe  Glu  Arg  Gly  Gln  Asn  Lys  Val  Val  Gly

813  CTG  ACC  GCG  AAT  GGT  GAG  ATT  GAG  AAT  ATA  ACC
 54◄Gln  Gly  Arg  Ile  Thr  Leu  Asn  Leu  Ile  Tyr  Gly

846  TTT  CAT  TCC  CAG  CGG  TCG  GTC  GAT  AAA  AAA  ATC
 43◄Lys  Met  Gly  Leu  Pro  Arg  Asp  Ile  Phe  Phe  Asp
```

Fig.7d

```
 879 GAG ATA ACC GTT GGC CTC AAT CGG CGT TAA ACC
  32◄Leu Tyr Gly Asn Ala Glu Ile Pro Thr Leu Gly
 912 CGC CAC CAG ATG GGC ATT AAA CGA GTA TCC CGG
  21◄Ala Val Leu His Ala Asn Phe Ser Tyr Gly Pro
 945 CAG CAG GGG ATC ATT TTG CGC TTC AGC CAT
  10◄Leu Leu Pro Asp Asn Gln Ala Glu Ala Met
 975 ACTTTTCATA CTCCCGCCAT TCAGAGAAGA AACCAATTGT
1015 CCATATTGCA TCAGACATTG CCGTCACTGC GTCTTTTACT
1055 GGCTCTTCTC GCTAACCAAA CCGGTAACCC CGCTTATTAA
1095 AAGCATTCTG TAACAAAGCG GGACCAAAGC CATGACAAAA
1135 ACGCGTAACA AAAGTGTCTA TAATCACGGC AGAAAAGTCC
1175 ACATTGATTA TTTGCACGGC GTCACACTTT GCTATGCCAT
                                         BamHI
1215 AGCATTTTTA TCCATAAGAT TAGCGGATCC TACCTGACGC
1255 TTTTTATCGC AACTCTCTAC TGTTTCTCCA TACCCGTTTT
           NheI          EcoRI      NcoI
1295 TTTGGGCTAG CAGGAGGAAT TCACC ATG GAT CCC GTA
                                  1►Met Asp Pro Val
1332 ATC GTA GAA GAC ATA GAG CCA GGT ATT TAT TAC
   5►Ile Val Glu Asp Ile Glu Pro Gly Ile Tyr Tyr
1365 GGA ATT TCG AAT GAG AAT TAC CAC GCG GGT CCC
  16►Gly Ile Ser Asn Glu Asn Tyr His Ala Gly Pro
1398 GGT ATC AGT AAG TCT CAG CTC GAT GAC ATT GCT
```

Fig.7e

```
   27▶Gly  Ile  Ser  Lys  Ser  Gln  Leu  Asp  Asp  Ile  Ala
 1431 GAT  ACT  CCG  GCA  CTA  TAT  TTG  TGG  CGT  AAA  AAT

38▶Asp  Thr  Pro  Ala  Leu  Tyr  Leu  Trp  Arg  Lys  Asn
 1464 GCC  CCC  GTG  GAC  ACC  ACA  AAG  ACA  AAA  ACG  CTC

49▶Ala  Pro  Val  Asp  Thr  Thr  Lys  Thr  Lys  Thr  Leu
 1497 GAT  TTA  GGA  ACT  GCT  TTC  CAC  TGC  CGG  GTA  CTT

60▶Asp  Leu  Gly  Thr  Ala  Phe  His  Cys  Arg  Val  Leu
                      EcoRI
 1530 GAA  CCG  GAA  GAA  TTC  AGT  AAC  CGC  TTT  ATC  GTA

71▶Glu  Pro  Glu  Glu  Phe  Ser  Asn  Arg  Phe  Ile  Val
 1563 GCA  CCT  GAA  TTT  AAC  CGC  CGT  ACA  AAC  GCC  GGA

82▶Ala  Pro  Glu  Phe  Asn  Arg  Arg  Thr  Asn  Ala  Gly
 1596 AAA  GAA  GAA  GAG  AAA  GCG  TTT  CTG  ATG  GAA  TGC

93▶Lys  Glu  Glu  Glu  Lys  Ala  Phe  Leu  Met  Glu  Cys
 1629 GCA  AGC  ACA  GGA  AAA  ACG  GTT  ATC  ACT  GCG  GAA

104▶Ala  Ser  Thr  Gly  Lys  Thr  Val  Ile  Thr  Ala  Glu
 1662 GAA  GGC  CGG  AAA  ATT  GAA  CTC  ATG  TAT  CAA  AGC

115▶Glu  Gly  Arg  Lys  Ile  Glu  Leu  Met  Tyr  Gln  Ser
```

Fig.7f

```
1695  GTT ATG GCT TTG CCG CTG GGG CAA TGG CTT GTT
126▶  Val Met Ala Leu Pro Leu Gly Gln Trp Leu Val
1728  GAA AGC GCC GGA CAC GCT GAA TCA TCA ATT TAC
137▶  Glu Ser Ala Gly His Ala Glu Ser Ser Ile Tyr
1761  TGG GAA GAT CCT GAA ACA GGA ATT TTG TGT CGG
148▶  Trp Glu Asp Pro Glu Thr Gly Ile Leu Cys Arg
1794  TGC CGT CCG GAC AAA ATT ATC CCT GAA TTT CAC
159▶  Cys Arg Pro Asp Lys Ile Ile Pro Glu Phe His
1827  TGG ATC ATG GAC GTG AAA ACT ACG GCG GAT ATT
170▶  Trp Ile Met Asp Val Lys Thr Thr Ala Asp Ile
1860  CAA CGA TTC AAA ACC GCT TAT TAC GAC TAC CGC
181▶  Gln Arg Phe Lys Thr Ala Tyr Tyr Asp Tyr Arg
1893  TAT CAC GTT CAG GAT GCA TTC TAC AGT GAC GGT
192▶  Tyr His Val Gln Asp Ala Phe Tyr Ser Asp Gly
1926  TAT GAA GCA CAG TTT GGA GTG CAG CCA ACT TTC
203▶  Tyr Glu Ala Gln Phe Gly Val Gln Pro Thr Phe
1959  GTT TTT CTG GTT GCC AGC ACA ACT ATT GAA TGC
214▶  Val Phe Leu Val Ala Ser Thr Thr Ile Glu Cys
1992  GGA CGT TAT CCG GTT GAA ATT TTC ATG ATG GGC
```

Fig.7g

```
225▶Gly Arg Tyr Pro Val Glu Ile Phe Met Met Gly
2025 GAA GAA GCA AAA CTG GCA GGT CAA CAG GAA TAT

236▶Glu Glu Ala Lys Leu Ala Gly Gln Gln Glu Tyr
2058 CAC CGC AAT CTG CGA ACC CTG TCT GAC TGC CTG

247▶His Arg Asn Leu Arg Thr Leu Ser Asp Cys Leu
                      BalI
2091 AAT ACC GAT GAA TGG CCA GCT ATT AAG ACA TTA

258▶Asn Thr Asp Glu Trp Pro Ala Ile Lys Thr Leu
2124 TCA CTG CCC CGC TGG GCT AAG GAA TAT GCAA

269▶Ser Leu Pro Arg Trp Ala Lys Glu Tyr AlaA
2155 ATG ACT AAG CAA CCA CCA ATC GCA AAA GCC GAT
   1▶Met Thr Lys Gln Pro Pro Ile Ala Lys Ala Asp
279▶s nAs p• • •

2188 CTG CAA AAA ACT CAG GGA AAC CGT GCA CCA GCA
  12▶Leu Gln Lys Thr Gln Gly Asn Arg Ala Pro Ala

2221 GCA GTT AAA AAT AGC GAC GTG ATT AGT TTT ATT
  23▶Ala Val Lys Asn Ser Asp Val Ile Ser Phe Ile

2254 AAC CAG CCA TCA ATG AAA GAG CAA CTG GCA GCA
  34▶Asn Gln Pro Ser Met Lys Glu Gln Leu Ala Ala
                      NdeI
2287 GCT CTT CCA CGC CAT ATG ACG GCT GAA CGT ATG
  45▶Ala Leu Pro Arg His Met Thr Ala Glu Arg Met
```

Fig.7h

```
2320 ATC CGT ATC GCC ACC ACA GAA ATT CGT AAA GTT
  56▶Ile Arg Ile Ala Thr Thr Glu Ile Arg Lys Val
2353 CCG GCG TTA GGA AAC TGT GAC ACT ATG AGT TTT
  67▶Pro Ala Leu Gly Asn Cys Asp Thr Met Ser Phe
2386 GTC AGT GCG ATC GTA CAG TGT TCA CAG CTC GGA
  78▶Val Ser Ala Ile Val Gln Cys Ser Gln Leu Gly
2419 CTT GAG CCA GGT AGC GCC CTC GGT CAT GCA TAT
  89▶Leu Glu Pro Gly Ser Ala Leu Gly His Ala Tyr
2452 TTA CTG CCT TTT GGT AAT AAA AAC GAA AAG AGC
 100▶Leu Leu Pro Phe Gly Asn Lys Asn Glu Lys Ser
2485 GGT AAA AAG AAC GTT CAG CTA ATC ATT GGC TAT
 111▶Gly Lys Lys Asn Val Gln Leu Ile Ile Gly Tyr
2518 CGC GGC ATG ATT GAT CTG GCT CGC CGT TCT GGT
 122▶Arg Gly Met Ile Asp Leu Ala Arg Arg Ser Gly
2551 CAA ATC GCC AGC CTG TCA GCC CGT GTT GTC CGT
 133▶Gln Ile Ala Ser Leu Ser Ala Arg Val Val Arg
2584 GAA GGT GAC GAG TTT AGC TTC GAA TTT GGC CTT
 144▶Glu Gly Asp Glu Phe Ser Phe Glu Phe Gly Leu
2617 GAT GAA AAG TTA ATA CAC CGC CCG GGA GAA AAC
 155▶Asp Glu Lys Leu Ile His Arg Pro Gly Glu Asn
2650 GAA GAT GCC CCG GTT ACC CAC GTC TAT GCT GTC
 166▶Glu Asp Ala Pro Val Thr His Val Tyr Ala Val
2683 GCA AGA CTG AAA GAC GGA GGT ACT CAG TTT GAA
 177▶Ala Arg Leu Lys Asp Gly Gly Thr Gln Phe Glu
2716 GTT ATG ACG CGC AAA CAG ATT GAG CTG GTG CGC
 188▶Val Met Thr Arg Lys Gln Ile Glu Leu Val Arg
```

Fig.7i

```
2749 AGC CTG AGT AAA GCT GGT AAT AAC GGG CCG TGG
 199▶Ser Leu Ser Lys Ala Gly Asn Asn Gly Pro Trp

2782 GTA ACT CAC TGG GAA GAA ATG GCA AAG AAA ACG
 210▶Val Thr His Trp Glu Glu Met Ala Lys Lys Thr

2815 GCT ATT CGT CGC CTG TTC AAA TAT TTG CCC GTA
 221▶Ala Ile Arg Arg Leu Phe Lys Tyr Leu Pro Val

2848 TCA ATT GAG ATC CAG CGT GCA GTA TCA ATG GAT
 232▶Ser Ile Glu Ile Gln Arg Ala Val Ser Met Asp
                                         PstI
2881 GAA AAG GAA CCA CTG ACA ATC GAT CCT GCA GAT
 243▶Glu Lys Glu Pro Leu Thr Ile Asp Pro Ala Asp

2914 TCC TCT GTA TTA ACC GGG GAA TAC AGT GTA ATC
 254▶Ser Ser Val Leu Thr Gly Glu Tyr Ser Val Ile
                             BglII    HindIII
2947 GAT AAT TCA GAG GAA TAG ATCTAAGCTT
 265▶Asp Asn Ser Glu Glu •••

2975 GGCTGTTTTG GCGGATGAGA GAAGATTTTC AGCCTGATAC
3015 AGATTAAATC AGAACGCAGA AGCGGTCTGA TAAAACAGAA
3055 TTTGCCTGGC GGCAGTAGCG CGGTGGTCCC ACCTGACCCC
3095 ATGCCGAACT CAGAAGTGAA ACGCCGTAGC GCCGATGGTA
3135 GTGTGGGGTC TCCCCATGCG AGAGTAGGGA ACTGCCAGGC
3175 ATCAAATAAA ACGAAAGGCT CAGTCGAAAG ACTGGGCCTT
3215 TCGTTTTATC TGTTGTTTGT CGGTGAACGC TCTCCTGAGT
3255 AGGACAAATC CGCCGGGAGC GGATTTGAAC GTTGCGAAGC
3295 AACGGCCCGG AGGGTGGCGG GCAGGACGCC CGCCATAAAC
3335 TGCCAGGCAT CAAATTAAGC AGAAGGCCAT CCTGACGGAT
```

Fig.7j

```
3375 GGCCTTTTTG CGTTTCTACA AACTCTTTTG TTTATTTTTC
3415 TAAATACATT CAAATATGTA TCCGCTCATG AGACAATAAC
3455 CCTGATAAAT GCTTCAATAA TATTGAAAAA GGAAGAGT AT
                                           1▶Me
3495 G AGT ATT CAA CAT TTC CGT GTC GCC CTT ATT
    1▶t Ser Ile Gln His Phe Arg Val Ala Leu Ile
3526 CCC TTT TTT GCG GCA TTT TGC CTT CCT GTT TTT
   12▶Pro Phe Phe Ala Ala Phe Cys Leu Pro Val Phe
3559 GCT CAC CCA GAA ACG CTG GTG AAA GTA AAA GAT
   23▶Ala His Pro Glu Thr Leu Val Lys Val Lys Asp
3592 GCT GAA GAT CAG TTG GGT GCA CGA GTG GGT TAC
   34▶Ala Glu Asp Gln Leu Gly Ala Arg Val Gly Tyr
3625 ATC GAA CTG GAT CTC AAC AGC GGT AAG ATC CTT
   45▶Ile Glu Leu Asp Leu Asn Ser Gly Lys Ile Leu
3658 GAG AGT TTT CGC CCC GAA GAA CGT TTT CCA ATG
   56▶Glu Ser Phe Arg Pro Glu Glu Arg Phe Pro Met
3691 ATG AGC ACT TTT AAA GTT CTG CTA TGT GGC GCG
   67▶Met Ser Thr Phe Lys Val Leu Leu Cys Gly Ala
3724 GTA TTA TCC CGT GTT GAC GCC GGG CAA GAG CAA
   78▶Val Leu Ser Arg Val Asp Ala Gly Gln Glu Gln
3757 CTC GGT CGC CGC ATA CAC TAT TCT CAG AAT GAC
   89▶Leu Gly Arg Arg Ile His Tyr Ser Gln Asn Asp
                  ScaI
3790 TTG GTT GAG TAC TCA CCA GTC ACA GAA AAG CAT
  100▶Leu Val Glu Tyr Ser Pro Val Thr Glu Lys His
3823 CTT ACG GAT GGC ATG ACA GTA AGA GAA TTA TGC
  111▶Leu Thr Asp Gly Met Thr Val Arg Glu Leu Cys
```

Fig.7k

```
3856 AGT GCT GCC ATA ACC ATG AGT GAT AAC ACT GCG
 122▶Ser Ala Ala Ile Thr Met Ser Asp Asn Thr Ala

3889 GCC AAC TTA CTT CTG ACA ACG ATC GGA GGA CCG
 133▶Ala Asn Leu Leu Leu Thr Thr Ile Gly Gly Pro

3922 AAG GAG CTA ACC GCT TTT TTG CAC AAC ATG GGG
 144▶Lys Glu Leu Thr Ala Phe Leu His Asn Met Gly

3955 GAT CAT GTA ACT CGC CTT GAT CGT TGG GAA CCG
 155▶Asp His Val Thr Arg Leu Asp Arg Trp Glu Pro

3988 GAG CTG AAT GAA GCC ATA CCA AAC GAC GAG CGT
 166▶Glu Leu Asn Glu Ala Ile Pro Asn Asp Glu Arg

4021 GAC ACC ACG ATG CCT GTA GCA ATG GCA ACA ACG
 177▶Asp Thr Thr Met Pro Val Ala Met Ala Thr Thr

4054 TTG CGC AAA CTA TTA ACT GGC GAA CTA CTT ACT
 188▶Leu Arg Lys Leu Leu Thr Gly Glu Leu Leu Thr

4087 CTA GCT TCC CGG CAA CAA TTA ATA GAC TGG ATG
 199▶Leu Ala Ser Arg Gln Gln Leu Ile Asp Trp Met

4120 GAG GCG GAT AAA GTT GCA GGA CCA CTT CTG CGC
 210▶Glu Ala Asp Lys Val Ala Gly Pro Leu Leu Arg

4153 TCG GCC CTT CCG GCT GGC TGG TTT ATT GCT GAT
 221▶Ser Ala Leu Pro Ala Gly Trp Phe Ile Ala Asp

4186 AAA TCT GGA GCC GGT GAG CGT GGG TCT CGC GGT
 232▶Lys Ser Gly Ala Gly Glu Arg Gly Ser Arg Gly

4219 ATC ATT GCA GCA CTG GGG CCA GAT GGT AAG CCC
 243▶Ile Ile Ala Ala Leu Gly Pro Asp Gly Lys Pro

4252 TCC CGT ATC GTA GTT ATC TAC ACG ACG GGG AGT
 254▶Ser Arg Ile Val Val Ile Tyr Thr Thr Gly Ser
```

Fig.71

```
4285 CAG GCA ACT ATG GAT GAA CGA AAT AGA CAG ATC
265▶Gln Ala Thr Met Asp Glu Arg Asn Arg Gln Ile
4318 GCT GAG ATA GGT GCC TCA CTG ATT AAG CAT TGG
276▶Ala Glu Ile Gly Ala Ser Leu Ile Lys His Trp
4351 TAA CTGTCAGACC AAGTTTACTC ATATATACTT
287▶•••
4384 TAGATTGATT TACGCGCCCT GTAGCGGCGC ATTAAGCGCG
4424 GCGGGTGTGG TGGTTACGCG CAGCGTGACC GCTACACTTG
4464 CCAGCGCCCT AGCGCCGCT CCTTTCGCTT TCTTCCCTTC
4504 CTTTCTCGCC ACGTTCGCCG GCTTTCCCCG TCAAGCTCTA
4544 AATCGGGGGC TCCCTTTAGG GTTCCGATTT AGTGCTTTAC
4584 GGCACCTCGA CCCCAAAAAA CTTGATTTGG GTGATGGTTC
4624 ACGTAGTGGG CCATCGCCCT GATAGACGGT TTTTCGCCCT
4664 TTGACGTTGG AGTCCACGTT CTTTAATAGT GGACTCTTGT
4704 TCCAAACTTG AACAACACTC AACCCTATCT CGGGCTATTC
4744 TTTTGATTTA TAAGGGATTT TGCCGATTTC GGCCTATTGG
4784 TTAAAAAATG AGCTGATTTA ACAAAAATTT AACGCGAATT
4824 TTAACAAAAT ATTAACGTTT ACAATTTAAA AGGATCTAGG
4864 TGAAGATCCT TTTTGATAAT CTCATGACCA AAATCCCTTA
4904 ACGTGAGTTT TCGTTCCACT GAGCGTCAGA CCCCGTAGAA
4944 AAGATCAAAG GATCTTCTTG AGATCCTTTT TTTCTGCGCG
4984 TAATCTGCTG CTTGCAAACA AAAAAACCAC CGCTACCAGC
5024 GGTGGTTTGT TTGCCGGATC AAGAGCTACC AACTCTTTTT
```

Fig.7m

```
5064  CCGAAGGTAA CTGGCTTCAG CAGAGCGCAG ATACCAAATA
5104  CTGTCCTTCT AGTGTAGCCG TAGTTAGGCC ACCACTTCAA
5144  GAACTCTGTA GCACCGCCTA CATACCTCGC TCTGCTAATC
5184  CTGTTACCAG TGGCTGCTGC CAGTGGCGAT AAGTCGTGTC
5224  TTACCGGGTT GGACTCAAGA CGATAGTTAC CGGATAAGGC
5264  GCAGCGGTCG GGCTGAACGG GGGGTTCGTG CACACAGCCC
5304  AGCTTGGAGC GAACGACCTA CACCGAACTG AGATACCTAC
5344  AGCGTGAGCT ATGAGAAAGC GCCACGCTTC CCGAAGGGAG
5384  AAAGGCGGAC AGGTATCCGG TAAGCGGCAG GGTCGGAACA
5424  GGAGAGCGCA CGAGGGAGCT TCCAGGGGGA AACGCCTGGT
5464  ATCTTTATAG TCCTGTCGGG TTTCGCCACC TCTGACTTGA
5504  GCGTCGATTT TTGTGATGCT CGTCAGGGGG GCGGAGCCTA
5544  TGGAAAAACG CCAGCAACGC GGCCTTTTTA CGGTTCCTGG
5584  CCTTTTGCTG GCCTTTTGCT CACATGTTCT TTCCTGCGTT
5624  ATCCCCTGAT TCTGTGGATA ACCGTATTAC CGCCTTTGAG
5664  TGAGCTGATA CCGCTCGCCG CAGCCGAACG ACCGAGCGCA
5704  GCGAGTCAGT GAGCGAGGAA GCGGAAGAGC GCCTGATGCG
5744  GTATTTTCTC CTTACGCATC TGTGCGGTAT TTCACACCGC
5784  ATAGGGTCAT GGCTGCGCCC CGACACCCGC CAACACCCGC
5824  TGACGCGCCC TGACGGGCTT GTCTGCTCCC GGCATCCGCT
5864  TACAGACAAG CTGTGACCGT CTCCGGGAGC TGCATGTGTC
5904  AGAGGTTTTC ACCGTCATCA CCGAAACGCG CGAGGCAGCA
5944  AGGAGATGGC GCCCAACAGT CCCCCGGCCA CGGGGCCTGC
```

Fig.7n

```
5984  CACCATACCC  ACGCCGAAAC  AAGCGCTCAT  GAGCCCGAAG
6024  TGGCGAGCCC  GATCTTCCCC  ATCGGTGATG  TCGGCGATAT
6064  AGGCGCCAGC  AACCGCACCT  GTGGCGCCGG  TGATGCCGGC
6104  CACGATGCGT  CCGGCGTAGA  GGATCTGCTC  ATGTTTGACA
6144  GCTTATC
```

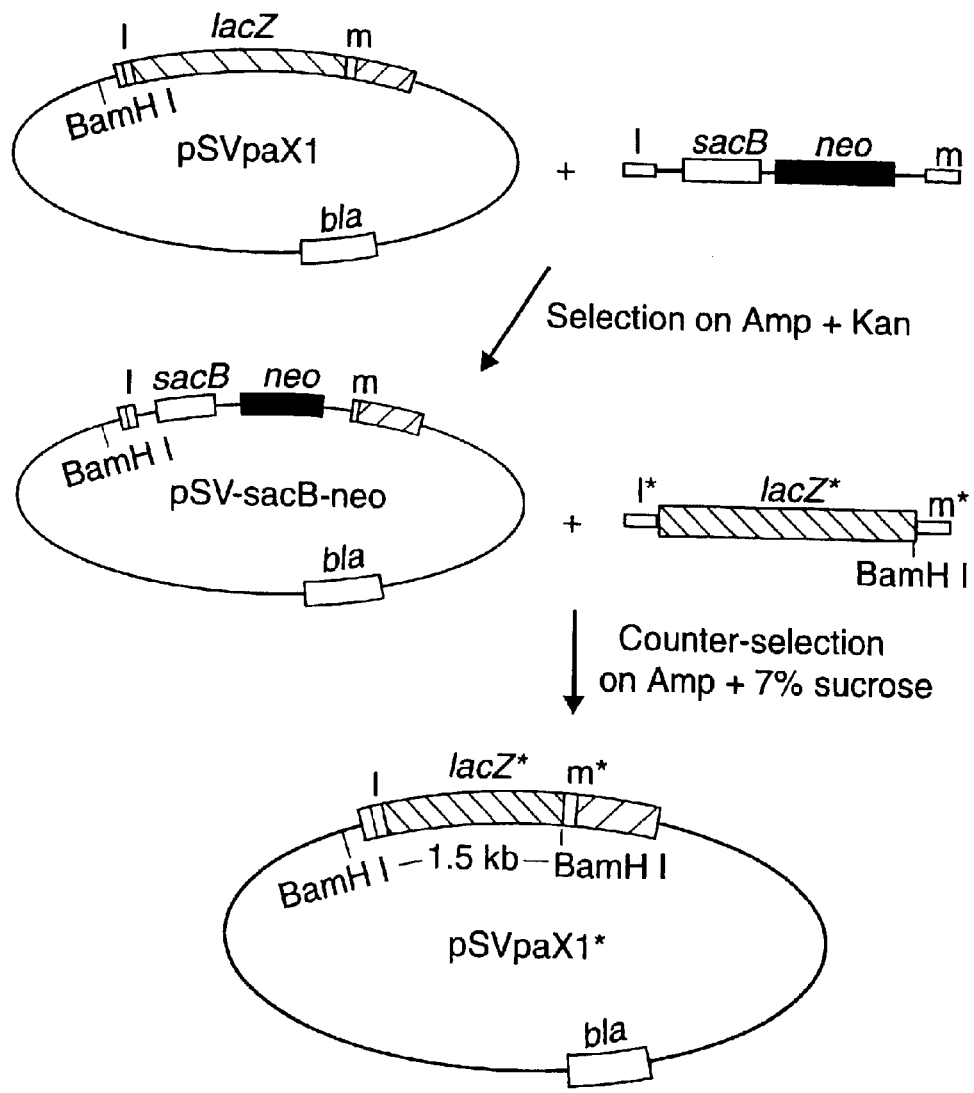

NS3145 (recA⁻, recBC⁺), P1 packaging strain

+

Fig. 13b

```
  1 ATCGATGCATAATGTGCCTGTCAAATGGACGAAGCAGGG
 40 ATTCTGCAAACCCTATGCTACTCCGTCAAGCCGTCAATT
 79 GTCTGATTCGTTACCAA TTA TGA CAA CTT GAC
                    293◄• • • Ser Leu Lys Val
111 GGC TAC ATC ATT CAC TTT TTC TTC ACA ACC
288◄Ala Val Asp Asn Val Lys Glu Glu Cys Gly
141 GGC ACG GAA CTC GCT CGG GCT GGC CCC GGT
278◄Ala Arg Phe Glu Ser Pro Ser Ala Gly Thr
171 GCA TTT TTT AAA TAC CCG CGA GAA ATA GAG
268◄Cys Lys Lys Phe Val Arg Ser Phe Tyr Leu
201 TTG ATC GTC AAA ACC AAC ATT GCG ACC GAC
258◄Gln Asp Asp Phe Gly Val Asn Arg Gly Val
231 GGT GGC GAT AGG CAT CCG GGT GGT GCT CAA
248◄Thr Ala Ile Pro Met Arg Thr Thr Ser Leu
261 AAG CAG CTT CGC CTG GCT GAT ACG TTG GTC
238◄Leu Leu Lys Ala Gln Ser Ile Arg Gln Asp
291 CTC GCG CCA GCT TAA GAC GCT AAT CCC TAA
228◄Glu Arg Trp Ser Leu Val Ser Ile Gly Leu
321 CTG CTG GCG GAA AAG ATG TGA CAG ACG CGA
218◄Gln Gln Arg Phe Leu His Ser Leu Arg Ser
351 CGG CGA CAA GCA AAC ATG CTG TGC GAC GCT
208◄Pro Ser Leu Cys Val His Gln Ala Val Ser
381 GGC GAT ATC AAA ATT GCT GTC TGC CAG GTG
198◄Ala Ile Asp Phe Asn Ser Asp Ala Leu His
411 ATC GCT GAT GTA CTG ACA AGC CTC GCG TAC
```

Fig.13c

```
188◄Asp Ser Ile Tyr Gln Cys Ala Glu Arg Val
441  CCG ATT ATC CAT CGG TGG ATG GAG CGA CTC
178◄Arg Asn Asp Met Pro Pro His Leu Ser Glu
471  GTT AAT CGC TTC CAT GCG CCG CAG TAA CAA
168◄Asn Ile Ala Glu Met Arg Arg Leu Leu Leu
501  TTG CTC AAG CAG ATT TAT CGC CAG CAG CTC
158◄Gln Glu Leu Leu Asn Ile Ala Leu Leu Glu
531  CGA ATA GCG CCC TTC CCC TTG CCC GGC GTT
148◄Ser Tyr Arg Gly Glu Gly Gln Gly Ala Asn
561  AAT GAT TTG CCC AAA CAG GTC GCT GAA ATG
138◄Ile Ile Gln Gly Phe Leu Asp Ser Phe His
591  CGG CTG GTG CGC TTC ATC CGG GCG AAA GAA
128◄Pro Gln His Ala Glu Asp Pro Arg Phe Phe
621  CCC CGT ATT GGC AAA TAT TGA CGG CCA GTT
118◄Gly Thr Asn Ala Phe Ile Ser Pro Trp Asn
651  AAG CCA TTC ATG CCA GTA GGC GCG CGG ACG
108◄Leu Trp Glu His Trp Tyr Ala Arg Pro Arg
681  AAA GTA AAC CCA CTG GTG ATA CCA TTC GCG
 98◄Phe Tyr Val Trp Gln His Tyr Trp Glu Arg
711  AGC CTC CGG ATG ACG ACC GTA GTG ATG AAT
 88◄Ala Glu Pro His Arg Gly Tyr His His Ile
741  CTC TCC TGG CGG GAA CAG CAA AAT ATC ACC
 78◄Glu Gly Pro Pro Phe Leu Leu Ile Asp Gly
771  CGG TCG GCA AAC AAA TTC TCG TCC CTG ATT
 68◄Pro Arg Cys Val Phe Glu Arg Gly Gln Asn
```

Fig.13e

```
1255 TTTTTATCGCAACTCTCTACTGTTTCTCCATACCCGTTT
          Nhel         EcoRI    Ncol  BamHI
1294 TTTTGGGCTAGCAGGAGGAAT TCACC ATG GAT CCC
                                1▶Met Asp Pro
1329 GTA ATC GTA GAA GAC ATA GAG CCA GGT ATT
   4▶Val Ile Val Glu Asp Ile Glu Pro Gly Ile
1359 TAT TAC GGA ATT TCG AAT GAG AAT TAC CAC
  14▶Tyr Tyr Gly Ile Ser Asn Glu Asn Tyr His
1389 GCG GGT CCC GGT ATC AGT AAG TCT CAG CTC
  24▶Ala Gly Pro Gly Ile Ser Lys Ser Gln Leu
1419 GAT GAC ATT GCT GAT ACT CCG GCA CTA TAT
  34▶Asp Asp Ile Ala Asp Thr Pro Ala Leu Tyr
1449 TTG TGG CGT AAA AAT GCC CCC GTG GAC ACC
  44▶Leu Trp Arg Lys Asn Ala Pro Val Asp Thr
1479 ACA AAG ACA AAA ACG CTC GAT TTA GGA ACT
  54▶Thr Lys Thr Lys Thr Leu Asp Leu Gly Thr
1509 GCT TTC CAC TGC CGG GTA CTT GAA CCG GAA
  64▶Ala Phe His Cys Arg Val Leu Glu Pro Glu
     EcoRI
1539 GAA TTC AGT AAC CGC TTT ATC GTA GCA CCT
  74▶Glu Phe Ser Asn Arg Phe Ile Val Ala Pro
1569 GAA TTT AAC CGC CGT ACA AAC GCC GGA AAA
  84▶Glu Phe Asn Arg Arg Thr Asn Ala Gly Lys
1599 GAA GAA GAG AAA GCG TTT CTG ATG GAA TGC
  94▶Glu Glu Glu Lys Ala Phe Leu Met Glu Cys
1629 GCA AGC ACA GGA AAA ACG GTT ATC ACT GCG
 104▶Ala Ser Thr Gly Lys Thr Val Ile Thr Ala
```

Fig.13f

```
1659 GAA GAA GGC CGG AAA ATT GAA CTC ATG TAT
114▶Glu Glu Gly Arg Lys Ile Glu Leu Met Tyr
1689 CAA AGC GTT ATG GCT TTG CCG CTG GGG CAA
124▶Gln Ser Val Met Ala Leu Pro Leu Gly Gln
1719 TGG CTT GTT GAA AGC GCC GGA CAC GCT GAA
134▶Trp Leu Val Glu Ser Ala Gly His Ala Glu
1749 TCA TCA ATT TAC TGG GAA GAT CCT GAA ACA
144▶Ser Ser Ile Tyr Trp Glu Asp Pro Glu Thr
1779 GGA ATT TTG TGT CGG TGC CGT CCG GAC AAA
154▶Gly Ile Leu Cys Arg Cys Arg Pro Asp Lys
1809 ATT ATC CCT GAA TTT CAC TGG ATC ATG GAC
164▶Ile Ile Pro Glu Phe His Trp Ile Met Asp
1839 GTG AAA ACT ACG GCG GAT ATT CAA CGA TTC
174▶Val Lys Thr Thr Ala Asp Ile Gln Arg Phe
1869 AAA ACC GCT TAT TAC GAC TAC CGC TAT CAC
184▶Lys Thr Ala Tyr Tyr Asp Tyr Arg Tyr His
1899 GTT CAG GAT GCA TTC TAC AGT GAC GGT TAT
194▶Val Gln Asp Ala Phe Tyr Ser Asp Gly Tyr
1929 GAA GCA CAG TTT GGA GTG CAG CCA ACT TTC
204▶Glu Ala Gln Phe Gly Val Gln Pro Thr Phe
1959 GTT TTT CTG GTT GCC AGC ACA ACT ATT GAA
214▶Val Phe Leu Val Ala Ser Thr Thr Ile Glu
1989 TGC GGA CGT TAT CCG GTT GAA ATT TTC ATG
224▶Cys Gly Arg Tyr Pro Val Glu Ile Phe Met
2019 ATG GGC GAA GAA GCA AAA CTG GCA GGT CAA
234▶Met Gly Glu Glu Ala Lys Leu Ala Gly Gln
```

Fig.13g

```
2049 CAG GAA TAT CAC CGC AAT CTG CGA ACC CTG
 244▶Gln Glu Tyr His Arg Asn Leu Arg Thr Leu

2079 TCT GAC TGC CTG AAT ACC GAT GAA TGG CCA
 254▶Ser Asp Cys Leu Asn Thr Asp Glu Trp Pro

2109 GCT ATT AAG ACA TTA TCA CTG CCC CGC TGG
 264▶Ala Ile Lys Thr Leu Ser Leu Pro Arg Trp
                                    Xhol  Kpnl
2139 GCT AAG GAA TAT GCA AAT GAC TAGATCTCGAG
 274▶Ala Lys Glu Tyr Ala Asn Asp

2171 GTACCCGAGCACGTGTTGACAATTAATCATCGGCATAGT

2210 ATATCGGCATAGTATAATACGACAAGGTGAGGAACTAAA
     Ncol
2249 CC ATG GCT AAG CAA CCA CCA ATC GCA AAA
      1▶Met Ala Lys Gln Pro Pro Ile Ala Lys 2278 GCC GAT CTG CAA AAA ACT CAG GGA AAC CGT
  10▶Ala Asp Leu Gln Lys Thr Gln Gly Asn Arg 2308 GCA CCA GCA GCA GTT AAA AAT AGC GAC GTG
  20▶Ala Pro Ala Ala Val Lys Asn Ser Asp Val 2338 ATT AGT TTT ATT AAC CAG CCA TCA ATG AAA
  30▶Ile Ser Phe Ile Asn Gln Pro Ser Met Lys 2368 GAG CAA CTG GCA GCA GCT CTT CCA CGC CAT
  40▶Glu Gln Leu Ala Ala Ala Leu Pro Arg His 2398 ATG ACG GCT GAA CGT ATG ATC CGT ATC GCC
  50▶Met Thr Ala Glu Arg Met Ile Arg Ile Ala 2428 ACC ACA GAA ATT CGT AAA GTT CCG GCG TTA
  60▶Thr Thr Glu Ile Arg Lys Val Pro Ala Leu
```

Fig.13h

```
2458  GGA  AAC  TGT  GAC  ACT  ATG  AGT  TTT  GTC  AGT
  70▶ Gly  Asn  Cys  Asp  Thr  Met  Ser  Phe  Val  Ser
2488  GCG  ATC  GTA  CAG  TGT  TCA  CAG  CTC  GGA  CTT
  80▶ Ala  Ile  Val  Gln  Cys  Ser  Gln  Leu  Gly  Leu
2518  GAG  CCA  GGT  AGC  GCC  CTC  GGT  CAT  GCA  TAT
  90▶ Glu  Pro  Gly  Ser  Ala  Leu  Gly  His  Ala  Tyr
2548  TTA  CTG  CCT  TTT  GGT  AAT  AAA  AAC  GAA  AAG
 100▶ Leu  Leu  Pro  Phe  Gly  Asn  Lys  Asn  Glu  Lys
2578  AGC  GGT  AAA  AAG  AAC  GTT  CAG  CTA  ATC  ATT
 110▶ Ser  Gly  Lys  Lys  Asn  Val  Gln  Leu  Ile  Ile
2608  GGC  TAT  CGC  GGC  ATG  ATT  GAT  CTG  GCT  CGC
 120▶ Gly  Tyr  Arg  Gly  Met  Ile  Asp  Leu  Ala  Arg
2638  CGT  TCT  GGT  CAA  ATC  GCC  AGC  CTG  TCA  GCC
 130▶ Arg  Ser  Gly  Gln  Ile  Ala  Ser  Leu  Ser  Ala
2668  CGT  GTT  GTC  CGT  GAA  GGT  GAC  GAG  TTT  AGC
 140▶ Arg  Val  Val  Arg  Glu  Gly  Asp  Glu  Phe  Ser
2698  TTC  GAA  TTT  GGC  CTT  GAT  GAA  AAG  TTA  ATA
 150▶ Phe  Glu  Phe  Gly  Leu  Asp  Glu  Lys  Leu  Ile
2728  CAC  CGC  CCG  GGA  GAA  AAC  GAA  GAT  GCC  CCG
 160▶ His  Arg  Pro  Gly  Glu  Asn  Glu  Asp  Ala  Pro
2758  GTT  ACC  CAC  GTC  TAT  GCT  GTC  GCA  AGA  CTG
 170▶ Val  Thr  His  Val  Tyr  Ala  Val  Ala  Arg  Leu
2788  AAA  GAC  GGA  GGT  ACT  CAG  TTT  GAA  GTT  ATG
 180▶ Lys  Asp  Gly  Gly  Thr  Gln  Phe  Glu  Val  Met
2818  ACG  CGC  AAA  CAG  ATT  GAG  CTG  GTG  CGC  AGC
 190▶ Thr  Arg  Lys  Gln  Ile  Glu  Leu  Val  Arg  Ser
```

Fig.13i

```
2848 CTG AGT AAA GCT GGT AAT AAC GGG CCG TGG
200▶Leu Ser Lys Ala Gly Asn Asn Gly Pro Trp

2878 GTA ACT CAC TGG GAA GAA ATG GCA AAG AAA
210▶Val Thr His Trp Glu Glu Met Ala Lys Lys

2908 ACG GCT ATT CGT CGC CTG TTC AAA TAT TTG
220▶Thr Ala Ile Arg Arg Leu Phe Lys Tyr Leu

2938 CCC GTA TCA ATT GAG ATC CAG CGT GCA GTA
230▶Pro Val Ser Ile Glu Ile Gln Arg Ala Val

2968 TCA ATG GAT GAA AAG GAA CCA CTG ACA ATC
240▶Ser Met Asp Glu Lys Glu Pro Leu Thr Ile

2998 GAT CCT GCA GAT TCC TCT GTA TTA ACC GGG
250▶Asp Pro Ala Asp Ser Ser Val Leu Thr Gly

3028 GAA TAC AGT GTA ATC GAT AAT TCA GAG GAA
260▶Glu Tyr Ser Val Ile Asp Asn Ser Glu Glu
         BglII    HindIII
3058 TAG ATCTAAGCTTCCTGCTGAACATCAAAGGCAAGAAA
270▶•••

3096 ACATCTGTTGTCAAAGACAGCATCCTTGAACAAGGACAA

3135 TTAACAGTTAACAAATAAAAACGCAAAAGAAAATGCCGA

3174 TATCCTATTGGCATTTTCTTTTATTTCTTATCAACATAA
                         XhoI
3213 AGGTGAATCCCATACCTCGAGCTTCACGCTGCCGCAAGC

3252 ACTCAGGGCGCAAGGGCTGCTAAAAGGAAGCGGAACACG

3291 TAGAAAGCCAGTCCGCAGAAACGGTGCTGACCCCGGATG

3330 AATGTCAGCTACTGGGCTATCTGGACAAGGGAAAACGCA

3369 AGCGCAAAGAGAAAGCAGGTAGCTTGCAGTGGGCTTACA
```

Fig.13j

```
3408 TGGCGATAGCTAGACTGGGCGGTTTTATGGACAGCAAGC
3447 GAACCGGAATTGCCAGCTGGGGCGCCCTCTGGTAAGGTT
3486 GGGAAGCCCTGCAAAGTAAACTGGATGGCTTTCTTGCCG
                                       BglII
3525 CCAAGGATCTGATGGCGCAGGGGATCAAGATCTGATCAA
3564 GAGACAGGATGAGGATCGTTTCGC ATG GAT ATT
                                   1▶Met Asp Ile

3597  AAT ACT GAA ACT GAG ATC AAG CAA AAG CAT
  4▶ Asn Thr Glu Thr Glu Ile Lys Gln Lys His

3627  TCA CTA ACC CCC TTT CCT GTT TTC CTA ATC
 14▶ Ser Leu Thr Pro Phe Pro Val Phe Leu Ile

3657  AGC CCG GCA TTT CGC GGG CGA TAT TTT CAC
 24▶ Ser Pro Ala Phe Arg Gly Arg Tyr Phe His

3687  AGC TAT TTC AGG AGT TCA GCC ATG AAC GCT
 34▶ Ser Tyr Phe Arg Ser Ser Ala Met Asn Ala

3717  TAT TAC ATT CAG GAT CGT CTT GAG GCT CAG
 44▶ Tyr Tyr Ile Gln Asp Arg Leu Glu Ala Gln

3747  AGC TGG GCG CGT CAC TAC CAG CAG CTC GCC
 54▶ Ser Trp Ala Arg His Tyr Gln Gln Leu Ala

3777  CGT GAA GAG AAA GAG GCA GAA CTG GCA GAC
 64▶ Arg Glu Glu Lys Glu Ala Glu Leu Ala Asp

3807  GAC ATG GAA AAA GGC CTG CCC CAG CAC CTG
 74▶ Asp Met Glu Lys Gly Leu Pro Gln His Leu

3837  TTT GAA TCG CTA TGC ATC GAT CAT TTG CAA
 84▶ Phe Glu Ser Leu Cys Ile Asp His Leu Gln

3867  CGC CAC GGG GCC AGC AAA AAA TCC ATT ACC
 94▶ Arg His Gly Ala Ser Lys Lys Ser Ile Thr
```

Fig.13k

```
3897 CGT GCG TTT GAT GAC GAT GTT GAG TTT CAG
 104▶Arg Ala Phe Asp Asp Asp Val Glu Phe Gln
3927 GAG CGC ATG GCA GAA CAC ATC CGG TAC ATG
 114▶Glu Arg Met Ala Glu His Ile Arg Tyr Met
3957 GTT GAA ACC ATT GCT CAC CAC CAG GTT GAT
 124▶Val Glu Thr Ile Ala His His Gln Val Asp
                                        HindIII
3987 ATT GAT TCA GAG GTA TAA AACGAGTAGA AGCT
 134▶Ile Asp Ser Glu Val ...
4019 TGGCTGTTTTGGCGGATGAGAGAAGATTTTCAGCCTGAT
4058 ACAGATTAAATCAGAACGCAGAAGCGGTCTGATAAAACA
4097 GAATTTGCCTGGCGGCAGTAGCGCGGTGGTCCCACCTGA
4136 CCCCATGCCGAACTCAGAAGTGAAACGCCGTAGCGCCGA
4175 TGGTAGTGTGGGGTCTCCCCATGCGAGAGTAGGGAACTG
4214 CCAGGCATCAAATAAAACGAAAGGCTCAGTCGAAAGACT
4253 GGGCCTTTCGTTTTATCTGTTGTTTGTCGGTGAACGCTC
4292 TCCTGAGTAGGACAAATCCGCCGGGAGCGGATTTGAACG
4331 TTGCGAAGCAACGGCCCGGAGGGTGGCGGGCAGGACGCC
4370 CGCCATAAACTGCCAGGCATCAAATTAAGCAGAAGGCCA
4409 TCCTGACGGATGGCCTTTTTGCGTTTCTACAAACTCTTT
4448 TGTTTATTTTTCTAAATACATTCAAATATGTATCCGCTC
4487 ATGAGACAATAACCCTGATAAATGCTTCAATAATATTGA
4526 AAAAGGAAGAGT ATG AGT ATT CAA CAT TTC
                1▶Met Ser Ile Gln His Phe
```

Fig.13I

```
4556 CGT GTC GCC CTT ATT CCC TTT TTT GCG GCA
   7▶Arg Val Ala Leu Ile Pro Phe Phe Ala Ala
4586 TTT TGC CTT CCT GTT TTT GCT CAC CCA GAA
  17▶Phe Cys Leu Pro Val Phe Ala His Pro Glu
4616 ACG CTG GTG AAA GTA AAA GAT GCT GAA GAT
  27▶Thr Leu Val Lys Val Lys Asp Ala Glu Asp
4646 CAG TTG GGT GCA CGA GTG GGT TAC ATC GAA
  37▶Gln Leu Gly Ala Arg Val Gly Tyr Ile Glu
4676 CTG GAT CTC AAC AGC GGT AAG ATC CTT GAG
  47▶Leu Asp Leu Asn Ser Gly Lys Ile Leu Glu
4706 AGT TTT CGC CCC GAA GAA CGT TTT CCA ATG
  57▶Ser Phe Arg Pro Glu Glu Arg Phe Pro Met
4736 ATG AGC ACT TTT AAA GTT CTG CTA TGT GGC
  67▶Met Ser Thr Phe Lys Val Leu Leu Cys Gly
4766 GCG GTA TTA TCC CGT GTT GAC GCC GGG CAA
  77▶Ala Val Leu Ser Arg Val Asp Ala Gly Gln
4796 GAG CAA CTC GGT CGC CGC ATA CAC TAT TCT
  87▶Glu Gln Leu Gly Arg Arg Ile His Tyr Ser
                                  ScaI
4826 CAG AAT GAC TTG GTT GAG TAC TCA CCA GTC
  97▶Gln Asn Asp Leu Val Glu Tyr Ser Pro Val
4856 ACA GAA AAG CAT CTT ACG GAT GGC ATG ACA
 107▶Thr Glu Lys His Leu Thr Asp Gly Met Thr
4886 GTA AGA GAA TTA TGC AGT GCT GCC ATA ACC
 117▶Val Arg Glu Leu Cys Ser Ala Ala Ile Thr
4916 ATG AGT GAT AAC ACT GCG GCC AAC TTA CTT
 127▶Met Ser Asp Asn Thr Ala Ala Asn Leu Leu
```

Fig.13m

```
4946  CTG ACA ACG ATC GGA GGA CCG AAG GAG CTA
 137▶ Leu Thr Thr Ile Gly Gly Pro Lys Glu Leu
4976  ACC GCT TTT TTG CAC AAC ATG GGG GAT CAT
 147▶ Thr Ala Phe Leu His Asn Met Gly Asp His
5006  GTA ACT CGC CTT GAT CGT TGG GAA CCG GAG
 157▶ Val Thr Arg Leu Asp Arg Trp Glu Pro Glu
5036  CTG AAT GAA GCC ATA CCA AAC GAC GAG CGT
 167▶ Leu Asn Glu Ala Ile Pro Asn Asp Glu Arg
5066  GAC ACC ACG ATG CCT GTA GCA ATG GCA ACA
 177▶ Asp Thr Thr Met Pro Val Ala Met Ala Thr
5096  ACG TTG CGC AAA CTA TTA ACT GGC GAA CTA
 187▶ Thr Leu Arg Lys Leu Leu Thr Gly Glu Leu
5126  CTT ACT CTA GCT TCC CGG CAA CAA TTA ATA
 197▶ Leu Thr Leu Ala Ser Arg Gln Gln Leu Ile
5156  GAC TGG ATG GAG GCG GAT AAA GTT GCA GGA
 207▶ Asp Trp Met Glu Ala Asp Lys Val Ala Gly
5186  CCA CTT CTG CGC TCG GCC CTT CCG GCT GGC
 217▶ Pro Leu Leu Arg Ser Ala Leu Pro Ala Gly
5216  TGG TTT ATT GCT GAT AAA TCT GGA GCC GGT
 227▶ Trp Phe Ile Ala Asp Lys Ser Gly Ala Gly
5246  GAG CGT GGG TCT CGC GGT ATC ATT GCA GCA
 237▶ Glu Arg Gly Ser Arg Gly Ile Ile Ala Ala
5276  CTG GGG CCA GAT GGT AAG CCC TCC CGT ATC
 247▶ Leu Gly Pro Asp Gly Lys Pro Ser Arg Ile
5306  GTA GTT ATC TAC ACG ACG GGG AGT CAG GCA
 257▶ Val Val Ile Tyr Thr Thr Gly Ser Gln Ala
```

Fig.13n

```
5336 ACT ATG GAT GAA CGA AAT AGA CAG ATC GCT
 267▶Thr Met Asp Glu Arg Asn Arg Gln Ile Ala
5366 GAG ATA GGT GCC TCA CTG ATT AAG CAT TGG
 277▶Glu Ile Gly Ala Ser Leu Ile Lys His Trp
5396 TAA CTGTCAGACCAAGTTTACTCATATATACTTTAGAT
 287▶...
5434 TGATTTACGCGCCCTGTAGCGGCGCATTAAGCGCGGCGG
5473 GTGTGGTGGTTACGCGCAGCGTGACCGCTACACTTGCCA
5512 GCGCCCTAGCGCCCGCTCCTTTCGCTTTCTTCCCTTCCT
5551 TTCTCGCCACGTTCGCCGGCTTTCCCCGTCAAGCTCTAA
5590 ATCGGGGGCTCCCTTTAGGGTTCCGATTTAGTGCTTTAC
5629 GGCACCTCGACCCCAAAAAACTTGATTTGGGTGATGGTT
5668 CACGTAGTGGGCCATCGCCCTGATAGACGGTTTTTCGCC
5707 CTTTGACGTTGGAGTCCACGTTCTTTAATAGTGGACTCT
5746 TGTTCCAAACTTGAACAACACTCAACCCTATCTCGGGCT
5785 ATTCTTTTGATTTATAAGGGATTTTGCCGATTTCGGCCT
5824 ATTGGTTAAAAAATGAGCTGATTTAACAAAAATTTAACG
5863 CGAATTTTAACAAAATATTAACGTTTACAATTTAAAAGG
5902 ATCTAGGTGAAGATCCTTTTTGATAATCTCATGACCAAA
5941 ATCCCTTAACGTGAGTTTTCGTTCCACTGAGCGTCAGAC
5980 CCCGTAGAAAGATCAAAGGATCTTCTTGAGATCCTTTT
6019 TTTCTGCGCGTAATCTGCTGCTTGCAAACAAAAAAACCA
6058 CCGCTACCAGCGGTGGTTTGTTTGCCGGATCAAGAGCTA
6097 CCAACTCTTTTTCCGAAGGTAACTGGCTTCAGCAGAGCG
```

Fig.13o

```
6136  CAGATACCAAATACTGTCCTTCTAGTGTAGCCGTAGTTA
6175  GGCCACCACTTCAAGAACTCTGTAGCACCGCCTACATAC
6214  CTCGCTCTGCTAATCCTGTTACCAGTGGCTGCTGCCAGT
6253  GGCGATAAGTCGTGTCTTACCGGGTTGGACTCAAGACGA
6292  TAGTTACCGGATAAGGCGCAGCGGTCGGGCTGAACGGGG
6331  GGTTCGTGCACACAGCCCAGCTTGGAGCGAACGACCTAC
6370  ACCGAACTGAGATACCTACAGCGTGAGCTATGAGAAAGC
6409  GCCACGCTTCCCGAAGGGAGAAAGGCGGACAGGTATCCG
6448  GTAAGCGGCAGGGTCGGAACAGGAGAGCGCACGAGGGAG
6487  CTTCCAGGGGGAAACGCCTGGTATCTTTATAGTCCTGTC
6526  GGGTTTCGCCACCTCTGACTTGAGCGTCGATTTTTGTGA
6565  TGCTCGTCAGGGGGGCGGAGCCTATGGAAAAACGCCAGC
6604  AACGCGGCCTTTTTACGGTTCCTGGCCTTTTGCTGGCCT
6643  TTTGCTCACATGTTCTTTCCTGCGTTATCCCCTGATTCT
6682  GTGGATAACCGTATTACCGCCTTTGAGTGAGCTGATACC
6721  GCTCGCCGCAGCCGAACGACCGAGCGCAGCGAGTCAGTG
6760  AGCGAGGAAGCGGAAGAGCGCCTGATGCGGTATTTTCTC
6799  CTTACGCATCTGTGCGGTATTTCACACCGCATAGGGTCA
6838  TGGCTGCGCCCCGACACCCGCCAACACCCGCTGACGCGC
6877  CCTGACGGGCTTGTCTGCTCCCGGCATCCGCTTACAGAC
6916  AAGCTGTGACCGTCTCCGGGAGCTGCATGTGTCAGAGGT
6955  TTTCACCGTCATCACCGAAACGCGCGAGGCAGCAAGGAG
```

Fig.13p

```
6994  ATGGCGCCCAACAGTCCCCCGGCCACGGGGCCTGCCACC
7033  ATACCCACGCCGAAACAAGCGCTCATGAGCCCGAAGTGG
7072  CGAGCCCGATCTTCCCCATCGGTGATGTCGGCGATATAG
7111  GCGCCAGCAACCGCACCTGTGGCGCCGGTGATGCCGGCC
7150  ACGATGCGTCCGGCGTAGAGGATCTGCTCATGTTTGACA
7189  GCTTATC
```

Fig.14b

```
         NsiI
  1  ATCGATGCATAATGTGCCTGTCAAATGGACGAAGCAGGG

40  ATTCTGCAAACCCTATGCTACTCCGTCAAGCCGTCAATT

79  GTCTGATTCGTTACCAA TTA TGA CAA CTT GAC
                  293◄• • • Ser Leu Lys Val

111  GGC TAC ATC ATT CAC TTT TTC TTC ACA ACC
288◄Ala Val Asp Asn Val Lys Glu Glu Cys Gly

141  GGC ACG GAA CTC GCT CGG GCT GGC CCC GGT
278◄Ala Arg Phe Glu Ser Pro Ser Ala Gly Thr

171  GCA TTT TTT AAA TAC CCG CGA GAA ATA GAG
268◄Cys Lys Lys Phe Val Arg Ser Phe Tyr Leu

201  TTG ATC GTC AAA ACC AAC ATT GCG ACC GAC
258◄Gln Asp Asp Phe Gly Val Asn Arg Gly Val

231  GGT GGC GAT AGG CAT CCG GGT GGT GCT CAA
248◄Thr Ala Ile Pro Met Arg Thr Thr Ser Leu

261  AAG CAG CTT CGC CTG GCT GAT ACG TTG GTC
238◄Leu Leu Lys Ala Gln Ser Ile Arg Gln Asp

291  CTC GCG CCA GCT TAA GAC GCT AAT CCC TAA
228◄Glu Arg Trp Ser Leu Val Ser Ile Gly Leu

321  CTG CTG GCG GAA AAG ATG TGA CAG ACG CGA
218◄Gln Gln Arg Phe Leu His Ser Leu Arg Ser

351  CGG CGA CAA GCA AAC ATG CTG TGC GAC GCT
208◄Pro Ser Leu Cys Val His Gln Ala Val Ser
         EcoRV
381  GGC GAT ATC AAA ATT GCT GTC TGC CAG GTG
198◄Ala Ile Asp Phe Asn Ser Asp Ala Leu His
```

Fig.14c

```
411 ATC GCT GAT GTA CTG ACA AGC CTC GCG TAC
188◄Asp Ser Ile Tyr Gln Cys Ala Glu Arg Val
441 CCG ATT ATC CAT CGG TGG ATG GAG CGA CTC
178◄Arg Asn Asp Met Pro Pro His Leu Ser Glu
471 GTT AAT CGC TTC CAT GCG CCG CAG TAA CAA
168◄Asn Ile Ala Glu Met Arg Arg Leu Leu Leu
501 TTG CTC AAG CAG ATT TAT CGC CAG CAG CTC
158◄Gln Glu Leu Leu Asn Ile Ala Leu Leu Glu
531 CGA ATA GCG CCC TTC CCC TTG CCC GGC GTT
148◄Ser Tyr Arg Gly Glu Gly Gln Gly Ala Asn
561 AAT GAT TTG CCC AAA CAG GTC GCT GAA ATG
138◄Ile Ile Gln Gly Phe Leu Asp Ser Phe His
591 CGG CTG GTG CGC TTC ATC CGG GCG AAA GAA
128◄Pro Gln His Ala Glu Asp Pro Arg Phe Phe
621 CCC CGT ATT GGC AAA TAT TGA CGG CCA GTT
118◄Gly Thr Asn Ala Phe Ile Ser Pro Trp Asn
651 AAG CCA TTC ATG CCA GTA GGC GCG CGG ACG
108◄Leu Trp Glu His Trp Tyr Ala Arg Pro Arg
681 AAA GTA AAC CCA CTG GTG ATA CCA TTC GCG
 98◄Phe Tyr Val Trp Gln His Tyr Trp Glu Arg
711 AGC CTC CGG ATG ACG ACC GTA GTG ATG AAT
 88◄Ala Glu Pro His Arg Gly Tyr His His Ile
741 CTC TCC TGG CGG GAA CAG CAA AAT ATC ACC
 78◄Glu Gly Pro Pro Phe Leu Leu Ile Asp Gly
771 CGG TCG GCA AAC AAA TTC TCG TCC CTG ATT
 68◄Pro Arg Cys Val Phe Glu Arg Gly Gln Asn
```

Fig.14d

```
 801 TTT CAC CAC CCC CTG ACC GCG AAT GGT GAG
  58◀Lys Val Val Gly Gln Gly Arg Ile Thr Leu

831 ATT GAG AAT ATA ACC TTT CAT TCC CAG CGG
  48◀Asn Leu Ile Tyr Gly Lys Met Gly Leu Pro

861 TCG GTC GAT AAA AAA ATC GAG ATA ACC GTT
  38◀Arg Asp Ile Phe Phe Asp Leu Tyr Gly Asn

891 GGC CTC AAT CGG CGT TAA ACC CGC CAC CAG
  28◀Ala Glu Ile Pro Thr Leu Gly Ala Val Leu

921 ATG GGC ATT AAA CGA GTA TCC CGG CAG CAG
  18◀His Ala Asn Phe Ser Tyr Gly Pro Leu Leu

951 GGG ATC ATT TTG CGC TTC AGC CAT ACTTTTC
   8◀Pro Asp Asn Gln Ala Glu Ala Met

982 ATACTCCCGCCATTCAGAGAAGAAACCAATTGTCCATAT
1021 TGCATCAGACATTGCCGTCACTGCGTCTTTTACTGGCTC
1060 TTCTCGCTAACCAAACCGGTAACCCCGCTTATTAAAAGC
1099 ATTCTGTAACAAAGCGGGACCAAAGCCATGACAAAAACG
1138 CGTAACAAAAGTGTCTATAATCACGGCAGAAAAGTCCAC
1177 ATTGATTATTTGCACGGCGTCACACTTTGCTATGCCATA
                                    BamHI
1216 GCATTTTTATCCATAAGATTAGCGGATCCTACCTGACGC
1255 TTTTTATCGCAACTCTCTACTGTTTCTCCATACCCGTTT
           NheI          EcoRI
1294 TTTTGGGCTAGCAGGAGGAATTCACC ATG ACA CCG
                                 1▶Met Thr Pro
                 PstI
1329 GAC ATT ATC CTG CAG CGT ACC GGG ATC GAT
```

Fig.14e

```
       4▶Asp Ile Ile Leu Gln Arg Thr Gly Ile Asp
    1359 GTG AGA GCT GTC GAA CAG GGG GAT GAT GCG
      14▶Val Arg Ala Val Glu Gln Gly Asp Asp Ala
    1389 TGG CAC AAA TTA CGG CTC GGC GTC ATC ACC
      24▶Trp His Lys Leu Arg Leu Gly Val Ile Thr
    1419 GCT TCA GAA GTT CAC AAC GTG ATA GCA AAA
      34▶Ala Ser Glu Val His Asn Val Ile Ala Lys
    1449 CCC CGC TCC GGA AAG AAG TGG CCT GAC ATG
      44▶Pro Arg Ser Gly Lys Lys Trp Pro Asp Met
    1479 AAA ATG TCC TAC TTC CAC ACC CTG CTT GCT
      54▶Lys Met Ser Tyr Phe His Thr Leu Leu Ala
    1509 GAG GTT TGC ACC GGT GTG GCT CCG GAA GTT
      64▶Glu Val Cys Thr Gly Val Ala Pro Glu Val
    1539 AAC GCT AAA GCA CTG GCC TGG GGA AAA CAG
      74▶Asn Ala Lys Ala Leu Ala Trp Gly Lys Gln
                                             EcoRI
    1569 TAC GAG AAC GAC GCC AGA ACC CTG TTT GAA
      84▶Tyr Glu Asn Asp Ala Arg Thr Leu Phe Glu
    1599 TTC ACT TCC GGC GTG AAT GTT ACT GAA TCC
      94▶Phe Thr Ser Gly Val Asn Val Thr Glu Ser
    1629 CCG ATC ATC TAT CGC GAC GAA AGT ATG CGT
     104▶Pro Ile Ile Tyr Arg Asp Glu Ser Met Arg
    1659 ACC GCC TGC TCT CCC GAT GGT TTA TGC AGT
     114▶Thr Ala Cys Ser Pro Asp Gly Leu Cys Ser
    1689 GAC GGC AAC GGC CTT GAA CTG AAA TGC CCG
     124▶Asp Gly Asn Gly Leu Glu Leu Lys Cys Pro
```

Fig.14f

```
1719 TTT ACC TCC CGG GAT TTC ATG AAG TTC CGG
134▶Phe Thr Ser Arg Asp Phe Met Lys Phe Arg

1749 CTC GGT GGT TTC GAG GCC ATA AAG TCA GCT
144▶Leu Gly Gly Phe Glu Ala Ile Lys Ser Ala

1779 TAC ATG GCC CAG GTG CAG TAC AGC ATG TGG
154▶Tyr Met Ala Gln Val Gln Tyr Ser Met Trp

1809 GTG ACG CGA AAA AAT GCC TGG TAC TTT GCC
164▶Val Thr Arg Lys Asn Ala Trp Tyr Phe Ala

1839 AAC TAT GAC CCG CGT ATG AAG CGT GAA GGC
174▶Asn Tyr Asp Pro Arg Met Lys Arg Glu Gly

1869 CTG CAT TAT GTC GTG ATT GAG CGG GAT GAA
184▶Leu His Tyr Val Val Ile Glu Arg Asp Glu

1899 AAG TAC ATG GCG AGT TTT GAC GAG ATC GTG
194▶Lys Tyr Met Ala Ser Phe Asp Glu Ile Val

1929 CCG GAG TTC ATC GAA AAA ATG GAC GAG GCA
204▶Pro Glu Phe Ile Glu Lys Met Asp Glu Ala

1959 CTG GCT GAA ATT GGT TTT GTA TTT GGG GAG
214▶Leu Ala Glu Ile Gly Phe Val Phe Gly Glu
                                    KpnI
1989 CAA TGG CGA TAGATCCGGTACCCGAGCACGTGTTGA
224▶Gln Trp Arg •••

2025 CAATTAATCATCGGCATAGTATATCGGCATAGTATAATA

2064 CGACAAGGTGAGGAACTAAACC ATG AGT ACT GCA
                        1▶Met Ser Thr Ala

2098 CTC GCA ACG CTG GCT GGG AAG CTG GCT GAA
  5▶Leu Ala Thr Leu Ala Gly Lys Leu Ala Glu
```

Fig.14g

```
                                        SalI
2128 CGT GTC GGC ATG GAT TCT GTC GAC CCA CAG
  15▶Arg Val Gly Met Asp Ser Val Asp Pro Gln

2158 GAA CTG ATC ACC ACT CTT CGC CAG ACG GCA
  25▶Glu Leu Ile Thr Thr Leu Arg Gln Thr Ala

2188 TTT AAA GGT GAT GCC AGC GAT GCG CAG TTC
  35▶Phe Lys Gly Asp Ala Ser Asp Ala Gln Phe

2218 ATC GCA TTA CTG ATC GTT GCC AAC CAG TAC
  45▶Ile Ala Leu Leu Ile Val Ala Asn Gln Tyr

2248 GGC CTT AAT CCG TGG ACG AAA GAA ATT TAC
  55▶Gly Leu Asn Pro Trp Thr Lys Glu Ile Tyr

2278 GCC TTT CCT GAT AAG CAG AAT GGC ATC GTT
  65▶Ala Phe Pro Asp Lys Gln Asn Gly Ile Val

2308 CCG GTG GTG GGC GTT GAT GGC TGG TCC CGC
  75▶Pro Val Val Gly Val Asp Gly Trp Ser Arg

2338 ATC ATC AAT GAA AAC CAG CAG TTT GAT GGC
  85▶Ile Ile Asn Glu Asn Gln Gln Phe Asp Gly

2368 ATG GAC TTT GAG CAG GAC AAT GAA TCC TGT
  95▶Met Asp Phe Glu Gln Asp Asn Glu Ser Cys

2398 ACA TGC CGG ATT TAC CGC AAG GAC CGT AAT
 105▶Thr Cys Arg Ile Tyr Arg Lys Asp Arg Asn

2428 CAT CCG ATC TGC GTT ACC GAA TGG ATG GAT
 115▶His Pro Ile Cys Val Thr Glu Trp Met Asp

2458 GAA TGC CGC CGC GAA CCA TTC AAA ACT CGC
 125▶Glu Cys Arg Arg Glu Pro Phe Lys Thr Arg

2488 GAA GGC AGA GAA ATC ACG GGG CCG TGG CAG
 135▶Glu Gly Arg Glu Ile Thr Gly Pro Trp Gln
```

Fig.14h

```
2518  TCG CAT CCC AAA CGG ATG TTA CGT CAT AAA
145▶  Ser His Pro Lys Arg Met Leu Arg His Lys

2548  GCC ATG ATT CAG TGT GCC CGT CTG GCC TTC
155▶  Ala Met Ile Gln Cys Ala Arg Leu Ala Phe

2578  GGA TTT GCT GGT ATC TAT GAC AAG GAT GAA
165▶  Gly Phe Ala Gly Ile Tyr Asp Lys Asp Glu

2608  GCC GAG CGC ATT GTC GAA AAT ACT GCA TAC
175▶  Ala Glu Arg Ile Val Glu Asn Thr Ala Tyr
          PstI
2638  ACT GCA GAA CGT CAG CCG GAA CGC GAC ATC
185▶  Thr Ala Glu Arg Gln Pro Glu Arg Asp Ile

2668  ACT CCG GTT AAC GAT GAA ACC ATG CAG GAG
195▶  Thr Pro Val Asn Asp Glu Thr Met Gln Glu

2698  ATT AAC ACT CTG CTG ATC GCC CTG GAT AAA
205▶  Ile Asn Thr Leu Leu Ile Ala Leu Asp Lys

2728  ACA TGG GAT GAC GAC TTA TTG CCG CTC TGT
215▶  Thr Trp Asp Asp Asp Leu Leu Pro Leu Cys

2758  TCC CAG ATA TTT CGC CGC GAC ATT CGT GCA
225▶  Ser Gln Ile Phe Arg Arg Asp Ile Arg Ala

2788  TCG TCA GAA CTG ACA CAG GCC GAA GCA GTA
235▶  Ser Ser Glu Leu Thr Gln Ala Glu Ala Val

2818  AAA GCT CTT GGA TTC CTG AAA CAG AAA GCC
245▶  Lys Ala Leu Gly Phe Leu Lys Gln Lys Ala
                                    BglII XhoI
2848  GCA GAG CAG AAG GTG GCA GCA TAGATCTCGAG
255▶  Ala Glu Gln Lys Val Ala Ala ···
```

Fig.14i

```
        HindIII
2880  AAGCTTCCTGCTGAACATCAAAGGCAAGAAAACATCTGT
2919  TGTCAAAGACAGCATCCTTGAACAAGGACAATTAACAGT
2958  TAACAAATAAAAACGCAAAAGAAAATGCCGATATCCTAT
2997  TGGCATTTTCTTTTATTTCTTATCAACATAAAGGTGAAT
                Xhol
3036  CCCATACCTCGAGCTTCACGCTGCCGCAAGCACTCAGGG
3075  CGCAAGGGCTGCTAAAAGGAAGCGGAACACGTAGAAAGC
3114  CAGTCCGCAGAAACGGTGCTGACCCCGGATGAATGTCAG
3153  CTACTGGGCTATCTGGACAAGGGAAAACGCAAGCGCAAA
3192  GAGAAAGCAGGTAGCTTGCAGTGGGCTTACATGGCGATA
3231  GCTAGACTGGGCGGTTTTATGGACAGCAAGCGAACCGGA
                PvuII
3270  ATTGCCAGCTGGGGCGCCCTCTGGTAAGGTTGGGAAGCC
3309  CTGCAAAGTAAACTGGATGGCTTTCTTGCCGCCAAGGAT
                       BglII
3348  CTGATGGCGCAGGGGATCAAGATCTGATCAAGAGACAGG
3387  ATGAGGATCGTTTCGC ATG GAT ATT AAT ACT
                    1▶Met Asp Ile Asn Thr 3418  GAA ACT GAG ATC AAG CAA AAG CAT TCA CTA
    6▶Glu Thr Glu Ile Lys Gln Lys His Ser Leu 3448  ACC CCC TTT CCT GTT TTC CTA ATC AGC CCG
   16▶Thr Pro Phe Pro Val Phe Leu Ile Ser Pro 3478  GCA TTT CGC GGG CGA TAT TTT CAC AGC TAT
   26▶Ala Phe Arg Gly Arg Tyr Phe His Ser Tyr 3508  TTC AGG AGT TCA GCC ATG AAC GCT TAT TAC
   36▶Phe Arg Ser Ser Ala Met Asn Ala Tyr Tyr
```

Fig.14j

```
3538 ATT CAG GAT CGT CTT GAG GCT CAG AGC TGG
  46▶Ile Gln Asp Arg Leu Glu Ala Gln Ser Trp

3568 GCG CGT CAC TAC CAG CAG CTC GCC CGT GAA
  56▶Ala Arg His Tyr Gln Gln Leu Ala Arg Glu

3598 GAG AAA GAG GCA GAA CTG GCA GAC GAC ATG
  66▶Glu Lys Glu Ala Glu Leu Ala Asp Asp Met

3628 GAA AAA GGC CTG CCC CAG CAC CTG TTT GAA
  76▶Glu Lys Gly Leu Pro Gln His Leu Phe Glu

3658 TCG CTA TGC ATC GAT CAT TTG CAA CGC CAC
  86▶Ser Leu Cys Ile Asp His Leu Gln Arg His

3688 GGG GCC AGC AAA AAA TCC ATT ACC CGT GCG
  96▶Gly Ala Ser Lys Lys Ser Ile Thr Arg Ala

3718 TTT GAT GAC GAT GTT GAG TTT CAG GAG CGC
 106▶Phe Asp Asp Asp Val Glu Phe Gln Glu Arg

3748 ATG GCA GAA CAC ATC CGG TAC ATG GTT GAA
 116▶Met Ala Glu His Ile Arg Tyr Met Val Glu

3778 ACC ATT GCT CAC CAC CAG GTT GAT ATT GAT
 126▶Thr Ile Ala His His Gln Val Asp Ile Asp
                                    HindIII
3808 TCA GAG GTA TAA AACGAGTAGA AGC TTG GCT
 136▶Ser Glu Val •••

3839 GTT TTG GCG GAT GAG AGA AGA TTT TCA GCC

3869 TGA TACAGATTAAATCAGAACGCAGAAGCGGTCTGATA

3907 AAACAGAATTTGCCTGGCGGCAGTAGCGCGGTGGTCCCA

3946 CCTGACCCCATGCCGAACTCAGAAGTGAAACGCCGTAGC

3985 GCCGATGGTAGTGTGGGGTCTCCCCATGCGAGAGTAGGG
```

Fig.14k

```
4024 AACTGCCAGGCATCAAATAAAACGAAAGGCTCAGTCGAA
4063 AGACTGGGCCTTTCGTTTTATCTGTTGTTTGTCGGTGAA
4102 CGCTCTCCTGAGTAGGACAAATCCGCCGGGAGCGGATTT
4141 GAACGTTGCGAAGCAACGGCCCGGAGGGTGGCGGGCAGG
4180 ACGCCCGCCATAAACTGCCAGGCATCAAATTAAGCAGAA
4219 GGCCATCCTGACGGATGGCCTTTTTGCGTTTCTACAAAC
4258 TCTTTTGTTTATTTTTCTAAATACATTCAAATATGTATC
4297 CGCTCATGAGACAATAACCCTGATAAATGCTTCAATAAT
4336 ATTGAAAAAGGAAGAGT ATG AGT ATT CAA CAT
                         1▶Met Ser Ile Gln His
4368     TTC CGT GTC GCC CTT ATT CCC TTT TTT GCG
     6▶  Phe Arg Val Ala Leu Ile Pro Phe Phe Ala
4398     GCA TTT TGC CTT CCT GTT TTT GCT CAC CCA
    16▶  Ala Phe Cys Leu Pro Val Phe Ala His Pro
4428     GAA ACG CTG GTG AAA GTA AAA GAT GCT GAA
    26▶  Glu Thr Leu Val Lys Val Lys Asp Ala Glu
4458     GAT CAG TTG GGT GCA CGA GTG GGT TAC ATC
    36▶  Asp Gln Leu Gly Ala Arg Val Gly Tyr Ile
4488     GAA CTG GAT CTC AAC AGC GGT AAG ATC CTT
    46▶  Glu Leu Asp Leu Asn Ser Gly Lys Ile Leu
4518     GAG AGT TTT CGC CCC GAA GAA CGT TTT CCA
    56▶  Glu Ser Phe Arg Pro Glu Glu Arg Phe Pro
4548     ATG ATG AGC ACT TTT AAA GTT CTG CTA TGT
    66▶  Met Met Ser Thr Phe Lys Val Leu Leu Cys
```

Fig.14I

```
4578 GGC GCG GTA TTA TCC CGT GTT GAC GCC GGG
  76▶Gly Ala Val Leu Ser Arg Val Asp Ala Gly

4608 CAA GAG CAA CTC GGT CGC CGC ATA CAC TAT
  86▶Gln Glu Gln Leu Gly Arg Arg Ile His Tyr
                                   ScaI
4638 TCT CAG AAT GAC TTG GTT GAG TAC TCA CCA
  96▶Ser Gln Asn Asp Leu Val Glu Tyr Ser Pro

4668 GTC ACA GAA AAG CAT CTT ACG GAT GGC ATG
 106▶Val Thr Glu Lys His Leu Thr Asp Gly Met

4698 ACA GTA AGA GAA TTA TGC AGT GCT GCC ATA
 116▶Thr Val Arg Glu Leu Cys Ser Ala Ala Ile

4728 ACC ATG AGT GAT AAC ACT GCG GCC AAC TTA
 126▶Thr Met Ser Asp Asn Thr Ala Ala Asn Leu

4758 CTT CTG ACA ACG ATC GGA GGA CCG AAG GAG
 136▶Leu Leu Thr Thr Ile Gly Gly Pro Lys Glu

4788 CTA ACC GCT TTT TTG CAC AAC ATG GGG GAT
 146▶Leu Thr Ala Phe Leu His Asn Met Gly Asp

4818 CAT GTA ACT CGC CTT GAT CGT TGG GAA CCG
 156▶His Val Thr Arg Leu Asp Arg Trp Glu Pro

4848 GAG CTG AAT GAA GCC ATA CCA AAC GAC GAG
 166▶Glu Leu Asn Glu Ala Ile Pro Asn Asp Glu

4878 CGT GAC ACC ACG ATG CCT GTA GCA ATG GCA
 176▶Arg Asp Thr Thr Met Pro Val Ala Met Ala

4908 ACA ACG TTG CGC AAA CTA TTA ACT GGC GAA
 186▶Thr Thr Leu Arg Lys Leu Leu Thr Gly Glu

4938 CTA CTT ACT CTA GCT TCC CGG CAA CAA TTA
 196▶Leu Leu Thr Leu Ala Ser Arg Gln Gln Leu
```

Fig.14m

```
4968 ATA GAC TGG ATG GAG GCG GAT AAA GTT GCA
 206▶Ile Asp Trp Met Glu Ala Asp Lys Val Ala

4998 GGA CCA CTT CTG CGC TCG GCC CTT CCG GCT
 216▶Gly Pro Leu Leu Arg Ser Ala Leu Pro Ala

5028 GGC TGG TTT ATT GCT GAT AAA TCT GGA GCC
 226▶Gly Trp Phe Ile Ala Asp Lys Ser Gly Ala

5058 GGT GAG CGT GGG TCT CGC GGT ATC ATT GCA
 236▶Gly Glu Arg Gly Ser Arg Gly Ile Ile Ala

5088 GCA CTG GGG CCA GAT GGT AAG CCC TCC CGT
 246▶Ala Leu Gly Pro Asp Gly Lys Pro Ser Arg

5118 ATC GTA GTT ATC TAC ACG ACG GGG AGT CAG
 256▶Ile Val Val Ile Tyr Thr Thr Gly Ser Gln

5148 GCA ACT ATG GAT GAA CGA AAT AGA CAG ATC
 266▶Ala Thr Met Asp Glu Arg Asn Arg Gln Ile

5178 GCT GAG ATA GGT GCC TCA CTG ATT AAG CAT
 276▶Ala Glu Ile Gly Ala Ser Leu Ile Lys His

5208 TGG TAA CTGTCAGACCAAGTTTACTCATATATACTTT
 286▶Trp •••

5245 AGATTGATTTACGCGCCCTGTAGCGGCGCATTAAGCGCG
5284 GCGGGTGTGGTGGTTACGCGCAGCGTGACCGCTACACTT
5323 GCCAGCGCCCTAGCGCCCGCTCCTTTCGCTTTCTTCCCT
5362 TCCTTTCTCGCCACGTTCGCCGGCTTTCCCCGTCAAGCT
5401 CTAAATCGGGGGCTCCCTTTAGGGTTCCGATTTAGTGCT
5440 TTACGGCACCTCGACCCCAAAAAACTTGATTTGGGTGAT
5479 GGTTCACGTAGTGGGCCATCGCCCTGATAGACGGTTTTT
```

Fig.14n

```
5518  CGCCCTTTGACGTTGGAGTCCACGTTCTTTAATAGTGGA
5557  CTCTTGTTCCAAACTTGAACAACACTCAACCCTATCTCG
5596  GGCTATTCTTTTGATTTATAAGGGATTTTGCCGATTTCG
5635  GCCTATTGGTTAAAAAATGAGCTGATTTAACAAAAATTT
5674  AACGCGAATTTTAACAAAATATTAACGTTTACAATTTAA
5713  AAGGATCTAGGTGAAGATCCTTTTTGATAATCTCATGAC
5752  CAAAATCCCTTAACGTGAGTTTTCGTTCCACTGAGCGTC
5791  AGACCCCGTAGAAAAGATCAAAGGATCTTCTTGAGATCC
5830  TTTTTTTCTGCGCGTAATCTGCTGCTTGCAAACAAAAAA
5869  ACCACCGCTACCAGCGGTGGTTTGTTTGCCGGATCAAGA
5908  GCTACCAACTCTTTTTCCGAAGGTAACTGGCTTCAGCAG
5947  AGCGCAGATACCAAATACTGTCCTTCTAGTGTAGCCGTA
5986  GTTAGGCCACCACTTCAAGAACTCTGTAGCACCGCCTAC
6025  ATACCTCGCTCTGCTAATCCTGTTACCAGTGGCTGCTGC
6064  CAGTGGCGATAAGTCGTGTCTTACCGGGTTGGACTCAAG
6103  ACGATAGTTACCGGATAAGGCGCAGCGGTCGGGCTGAAC
6142  GGGGGGTTCGTGCACACAGCCCAGCTTGGAGCGAACGAC
6181  CTACACCGAACTGAGATACCTACAGCGTGAGCTATGAGA
6220  AAGCGCCACGCTTCCCGAAGGGAGAAAGGCGGACAGGTA
6259  TCCGGTAAGCGGCAGGGTCGGAACAGGAGAGCGCACGAG
6298  GGAGCTTCCAGGGGGAAACGCCTGGTATCTTTATAGTCC
6337  TGTCGGGTTTCGCCACCTCTGACTTGAGCGTCGATTTTT
```

Fig.14o

```
6376  GTGATGCTCGTCAGGGGGGCGGAGCCTATGGAAAAACGC
6415  CAGCAACGCGGCCTTTTTACGGTTCCTGGCCTTTTGCTG
6454  GCCTTTTGCTCACATGTTCTTTCCTGCGTTATCCCCTGA
6493  TTCTGTGGATAACCGTATTACCGCCTTTGAGTGAGCTGA
6532  TACCGCTCGCCGCAGCCGAACGACCGAGCGCAGCGAGTC
6571  AGTGAGCGAGGAAGCGGAAGAGCGCCTGATGCGGTATTT
6610  TCTCCTTACGCATCTGTGCGGTATTTCACACCGCATAGG
6649  GTCATGGCTGCGCCCCGACACCCGCCAACACCCGCTGAC
6688  GCGCCCTGACGGGCTTGTCTGCTCCCGGCATCCGCTTAC
6727  AGACAAGCTGTGACCGTCTCCGGGAGCTGCATGTGTCAG
6766  AGGTTTTCACCGTCATCACCGAAACGCGCGAGGCAGCAA
6805  GGAGATGGCGCCCAACAGTCCCCCGGCCACGGGGCCTGC
6844  CACCATACCCACGCCGAAACAAGCGCTCATGAGCCCGAA
6883  GTGGCGAGCCCGATCTTCCCCATCGGTGATGTCGGCGAT
6922  ATAGGCGCCAGCAACCGCACCTGTGGCGCCGGTGATGCC
6961  GGCCACGATGCGTCCGGCGTAGAGGATCTGCTCATGTTT
7000  GACAGCTTATC
```

DNA CLONING METHOD

This is a divisional application of U.S. application Ser. No. 09/555,510, filed Jun. 5, 2002 now U.S. Pat. No. 6,509,156, which is a 371 of PCT/EP98/07945, filed on Dec. 7, 1998. The disclosure of the prior application(s) is hereby incorporated by reference herein in its entirety.

DESCRIPTION

The invention refers to a novel method for cloning DNA molecules using a homologous recombination mechanism between at least two DNA molecules. Further, novel reagent kits suitable for DNA cloning are provided.

Current methods for cloning foreign DNA in bacterial cells usually comprise the steps of providing a suitable bacterial vector, cleaving said vector with a restriction enzyme and in vitro-inserting a foreign DNA fragment in said vector. The resulting recombinant vectors are then used to transform bacteria. Although such cloning methods have been used successfully for about 20 years they suffer from several drawbacks. These drawbacks are, in particular, that the in vitro steps required for inserting foreign DNA in a vector are often very complicated and time-consuming, if no suitable restriction sites are available on the foreign DNA or the vector.

Furthermore, current methods usually rely on the presence of suitable restriction enzyme cleavage sites in the vector into which the foreign DNA fragment is placed. This imposes two limitations on the final cloning product. First, the foreign DNA fragment can usually only be inserted into the vector at the position of such a restriction site or sites. Thus, the cloning product is limited by the disposition of suitable restriction sites and cloning into regions of the vector where there is no suitable restriction site, is difficult and often imprecise. Second, since restriction sites are typically 4 to 8 base pairs in length, they occur a multiple number of times as the size of the DNA molecules being used increases. This represents a practical limitation to the size of the DNA molecules that can be manipulated by most current cloning techniques. In particular, the larger sizes of DNA cloned into vectors such as cosmids, BACs, PACs and P1s are such that it is usually impractical to manipulate them directly by restriction enzyme based techniques. Therefore, there is a need for providing a new cloning method, from which the drawbacks of the prior art have at least partly been eliminated.

According to the present invention it was found that an efficient homologous recombination mechanism between two DNA molecules occurs at usable frequencies in a bacterial host cell which is capable of expressing the products of the recE and recT genes or functionally related genes such as the redα and redβ genes, or the phage P22 recombination system (Kolodner et al., Mol. Microbiol. 11 (1994) 23–30; Fenton, A. C. and Poteete, A. R., Virology 134 (1984) 148–160; Poteete, A. R. and Fenton, A. C., Virology 134 (1984) 161–167). This novel method of cloning DNA fragments is termed "ET cloning".

The identification and characterization of the E. coli RecE and RecT proteins is described Gillen et al. (J. Bacteriol. 145 (1981), 521–532) and Hall et al. (J. Bacteriol. 175 (1993), 277–287). Hall and Kolodner (Proc. Natl. Acad. Sci. USA 91 (1994), 3205–3209) disclose in vitro homologous pairing and strand exchange of linear double-stranded DNA and homologous circular single-stranded DNA promoted by the RecT protein. Any references to the use of this method for the cloning of DNA molecules in cells cannot be found therein.

The recET pathway of genetic recombination in E. coli is known (Hall and Kolodner (1994), supra; Gillen et al. (1981), supra). This pathway requires the expression of two genes, recE and recT. The DNA sequence of these genes has been published (Hall et al., supra). The RecE protein is similar to bacteriophage proteins, such as λ exo or λ Redα (Gillen et al., J. Mol. Biol. 113 (1977), 27–41; Little, J. Biol. Chem. 242 (1967), 679–686; Radding and Carter, J. Biol. Chem. 246 (1971), 2513–2518; Joseph and Kolodner, J. Biol. Chem. 258 (1983), 10418–10424). The RecT protein is similar to bacteriophage proteins, such as λ β-protein or λ Redβ (Hall et al. (1993), supra; Muniyappa and Radding, J. Biol. Chem. 261 (1986), 7472–7478; Kmiec and Hollomon, J. Biol. Chem. 256 (1981), 12636–12639). The content of the above-cited documents is incorporated herein by reference.

Oliner et al. (Nucl. Acids Res. 21 (1993), 5192–5197) describe in vivo cloning of PCR products in E. coli by intermolecular homologous recombination between a linear PCR product and a linearized plasmid vector. Other previous attempts to develop new cloning methods based on homologous recombination in prokaryotes, too, relied on the use of restriction enzymes to linearise the vector (Bubeck et al., Nucleic Acids Res. 21 (1993), 3601–3602; Oliner et al., Nucleic Acids Res. 21 (1993), 5192–5197; Degryse, Gene 170 (1996), 45–50) or on the host-specific recA-dependent recombination system (Hamilton et al., J. Bacteriol. 171 (1989), 4617–4622; Yang et al., Nature Biotech. 15 (1997), 859–865; Dabert and Smith, Genetics 145 (1997), 877–889). These methods are of very limited applicability and are hardly used in practice.

The novel method of cloning DNA according to the present invention does not require in vitro treatments with restriction enzymes or DNA ligases and is therefore fundamentally distinct from the standard methodologies of DNA cloning. The method relies on a pathway of homologous recombination in E. coli involving the recE and recT gene products, or the redα and redβ gene products, or functionally equivalent gene products. The method covalently combines one preferably linear and preferably extrachromosomal DNA fragment, the DNA fragment to be cloned, with one second preferably circular DNA vector molecule, either an episome or the endogenous host chromosome or chromosomes. It is therefore distinct from previous descriptions of cloning in E. coli by homologous recombination which either rely on the use of two linear DNA fragments or different recombination pathways.

The present invention provides a flexible way to use homologous recombination to engineer large DNA molecules including an intact>76 kb plasmid and the E. coli chromosome. Thus, there is practically no limitation of target choice either according to size or site. Therefore, any recipient DNA in a host cell, from high copy plasmid to the genome, is amenable to precise alteration. In addition to engineering large DNA molecules, the invention outlines new, restriction enzyme-independent approaches to DNA design. For example, deletions between any two chosen base pairs in a target episome can be made by choice of oligonucleotide homology arms. Similarly, chosen DNA sequences can be inserted at a chosen base pair to create, for example, altered protein reading frames. Concerted combinations of insertions and deletions, as well as point mutations, are also possible. The application of these strategies is particularly relevant to complex or difficult DNA constructions, for example, those intended for homologous recombinations in eukaryotic cells, e.g. mouse embryonic stem cells. Further, the present invention provides a simple way to position site specific recombination target sites exactly where desired. This will simplify applications of site specific recombination in other living systems, such as plants and mice.

A subject matter of the present invention is a method for cloning DNA molecules in cells comprising the steps:
a) providing a host cell capable of performing homologous recombination,
b) contacting in said host cell a first DNA molecule which is capable of being replicated in said host cell with a second DNA molecule comprising at least two regions of sequence homology to regions on the first DNA molecule, under conditions which favour homologous recombination between said first and second DNA molecules and
c) selecting a host cell in which homologous recombination between said first and second DNA molecules has occurred.

In the method of the present invention the homologous recombination preferably occurs via the recET mechanism, i.e. the homologous recombination is mediated by the gene products of the recE and the recT genes which are preferably selected from the *E. coli* genes recE and recT or functionally related genes such as the phage λ redα and redβ genes.

The host cell suitable for the method of the present invention preferably is a bacterial cell, e.g. a gram-negative bacterial cell. More preferably, the host cell is an enterobacterial cell, such as Salmonella, Klebsiella or Escherichia. Most preferably the host cell is an *Escherichia coli* cell. It should be noted, however, that the cloning method of the present invention is also suitable for eukaryotic cells, such as fungi, plant or animal cells.

Preferably, the host cell used for homologous recombination and propagation of the cloned DNA can be any cell, e.g. a bacterial strain in which the products of the recE and recT, or redα and redβ, genes are expressed. The host cell may comprise the recE and recT genes located on the host cell chromosome or on non-chromosomal DNA, preferably on a vector, e.g. a plasmid. In a preferred case, the RecE and RecT, or Redα and Redβ, gene products are expressed from two different regulatable promoters, such as the arabinose-inducible BAD promoter or the lac promoter or from non-regulatable promoters. Alternatively, the recE and recT, or redα and redβ, genes are expressed on a polycistronic mRNA from a single regulatable or non-regulatable promoter. Preferably the expression is controlled by regulatable promoters.

Especially preferred is also an embodiment, wherein the recE or redα gene is expressed by a regulatable promoter. Thus, the recombinogenic potential of the system is only elicited when required and, at other times, possible undesired recombination reactions are limited. The recT or redβ gene, on the other hand, is preferably overexpressed with respect to recE or redo. This may be accomplished by using a strong constitutive promoter, e.g. the EM7 promoter and/or by using a higher copy number of recT, or redβ, versus recE, or redα, genes.

For the purpose of the present invention any recE and recT genes are suitable insofar as they allow a homologous recombination of first and second DNA molecules with sufficient efficiency to give rise to recombination products in more than 1 in $10^9$ cells transfected with DNA. The recE and recT genes may be derived from any bacterial strain or from bacteriophages or may be mutants and variants thereof. Preferred are recE and recT genes which are derived from *E. coli* or from *E. coli* bacteriophages, such as the redα and redβ genes from lambdoid phages, e.g. bacteriophage λ.

Figure 7A:
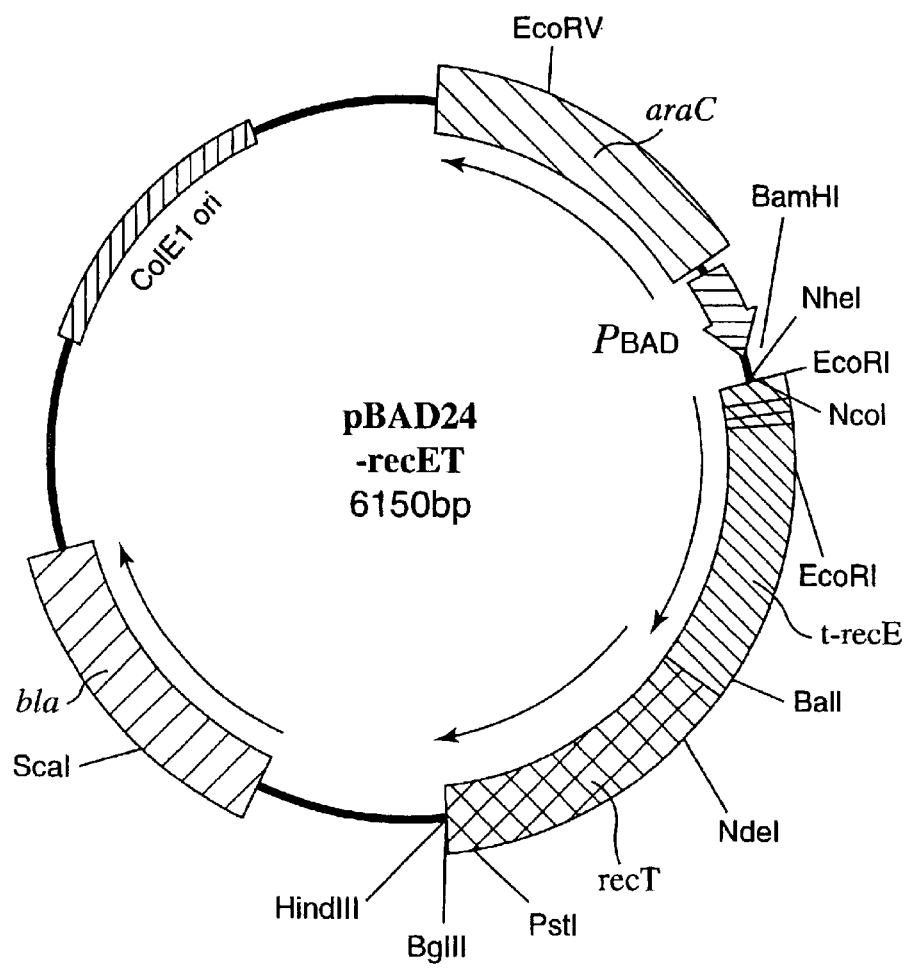
Figure 14A:
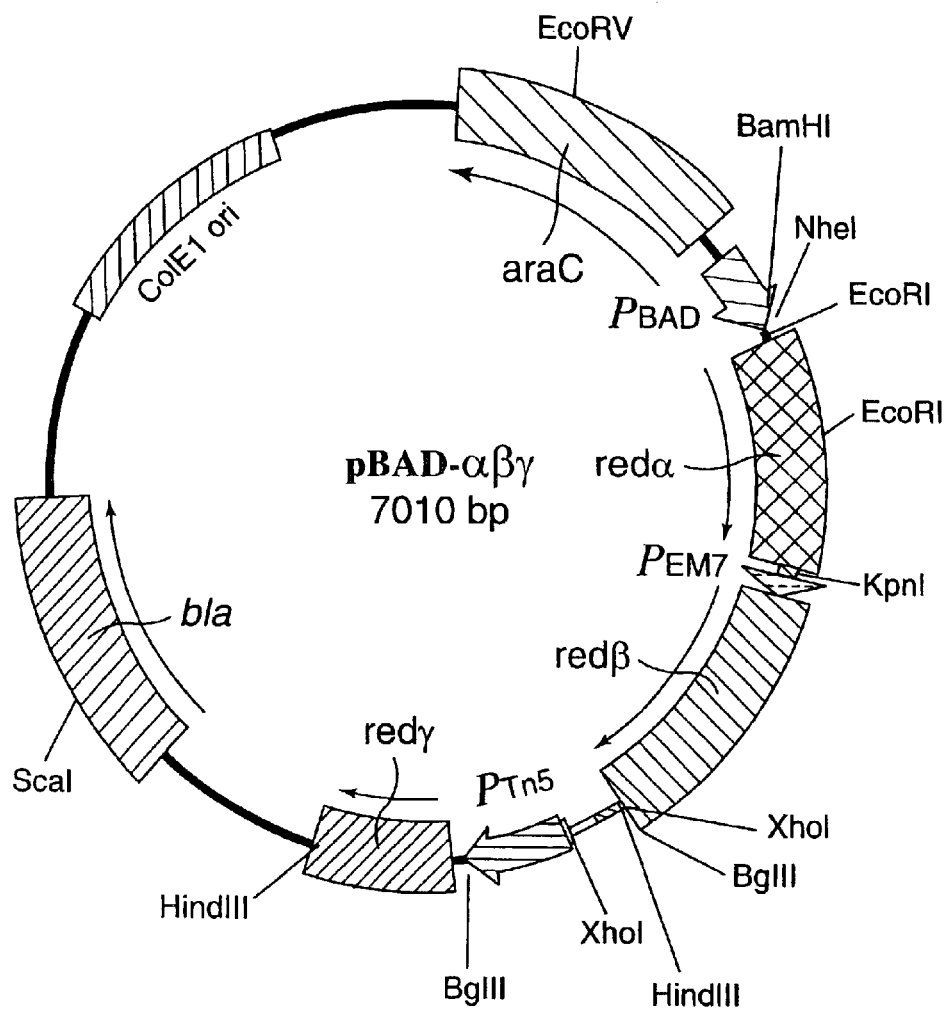

More preferably, the recE or redα gene is selected from a nucleic acid molecule comprising
(a) the nucleic acid sequence from position 1320 (ATG) to 2159 (GAC) as depicted in FIG. 7B or SEQ ID No. 2,
(b) the nucleic acid sequence from position 1320 (ATG) to 1998 (CGA) as depicted in FIG. 14B or SEQ ID No. 11,
(c) a nucleic acid encoding the same polypeptide within the degeneracy of the genetic code and/or
(d) a nucleic acid sequence which hybridizes under stringent conditions with the nucleic acid sequence from (a), (b) and/or (c).

More preferably, the recT or redβ gene is selected from a nucleic acid molecule comprising
(a) the nucleic acid sequence from position 2155 (ATG) to 2961 (GAA) as depicted in FIG. 7B or SEQ ID No. 4,
(b) the nucleic acid sequence from position 2086 (ATG) to 2868 (GCA) as depicted in FIG. 14B or SEQ ID No. 11,
(c) a nucleic acid encoding the same polypeptide within the degeneracy of the genetic code and/or
(d) a nucleic acid sequence which hybridizes under stringent conditions with the nucleic acid sequences from (a), (b) and/or (c).

It should be noted that the present invention also encompasses mutants and variants of the given sequences, e.g. naturally occurring mutants and variants or mutants and variants obtained by genetic engineering. Further it should be noted that the recE gene depicted in FIG. 7B is an already truncated gene encoding amino acids 588–866 of the native protein. Mutants and variants preferably have a nucleotide sequence identity of at least 60%, preferably of at least 70% and more preferably of at least 80% of the recE and recT sequences depicted in FIGS. 7B and 13B, and of the redα and redβ sequences depicted in FIG. 14B.

According to the present invention hybridization under stringent conditions preferably is defined according to Sambrook et al. (1989), infra, and comprises a detectable hybridization signal after washing for 30 min in 0.1×SSC, 0.5% SDS at 55° C., preferably at 62° C. and more preferably at 68° C.

In a preferred case the recE and recT genes are derived from the corresponding endogenous genes present in the *E. coli* K12 strain and its derivatives or from bacteriophages. In particular, strains that carry the sbcA mutation are suitable. Examples of such strains are JC 8679 and JC 9604 (Gillen et al. (1981), supra). Alternatively, the corresponding genes may also be obtained from other coliphages such as lambdoid phages or phage P22.

The genotype of JC 8679 and JC 9604 is Sex (Hfr, F+, F–, or F'): F– .JC 8679 comprises the mutations: recBC 21, recC 22, sbcA 23, thr-1, ara-14, leu B 6, DE (gpt-proA) 62, lacY1, tsx-33, gluV44 (AS), galK2 (Oc), LAM-, his-60, relA 1, rps L31 (strR), xyl A5, mtl-1, argE3 (Oc) and thi-1. JC 9604 comprises the same mutations and further the mutation recA 56.

Further, it should be noted that the recE and recT, or redα and redβ, genes can be isolated from a first donor source, e.g. a donor bacterial cell and transformed into a second receptor source, e.g. a receptor bacterial or eukaryotic cell in which they are expressed by recombinant DNA means.

In one embodiment of the invention, the host cell used is a bacterial strain having an sbcA mutation, e.g. one of *E. coli* strains JC 8679 and JC 9604 mentioned above. However, the method of the invention is not limited to host cells having an sbcA mutation or analogous cells. Surprisingly, it has been found that the cloning method of the invention also works in cells without sbcA mutation, whether recBC+ or recBC−, e.g. also in prokaryotic recBC+ host cells, e.g. in *E. coli* recBC+ cells. In that case preferably those host cells are used in which the product of a recBC type exonuclease inhibitor gene is expressed. Preferably, the exonuclease inhibitor is capable of inhibiting the host recBC system or an equivalent thereof. A suitable example of such exonuclease inhibitor gene is the λ redγ gene (Murphy, J. Bacteriol. 173 (1991), 5808–5821) and functional equivalents thereof, respectively, which, for example, can be obtained from other coliphages such as from phage P22 (Murphy, J. Biol. Chem. 269 (1994), 22507–22516).

Figure 13A:
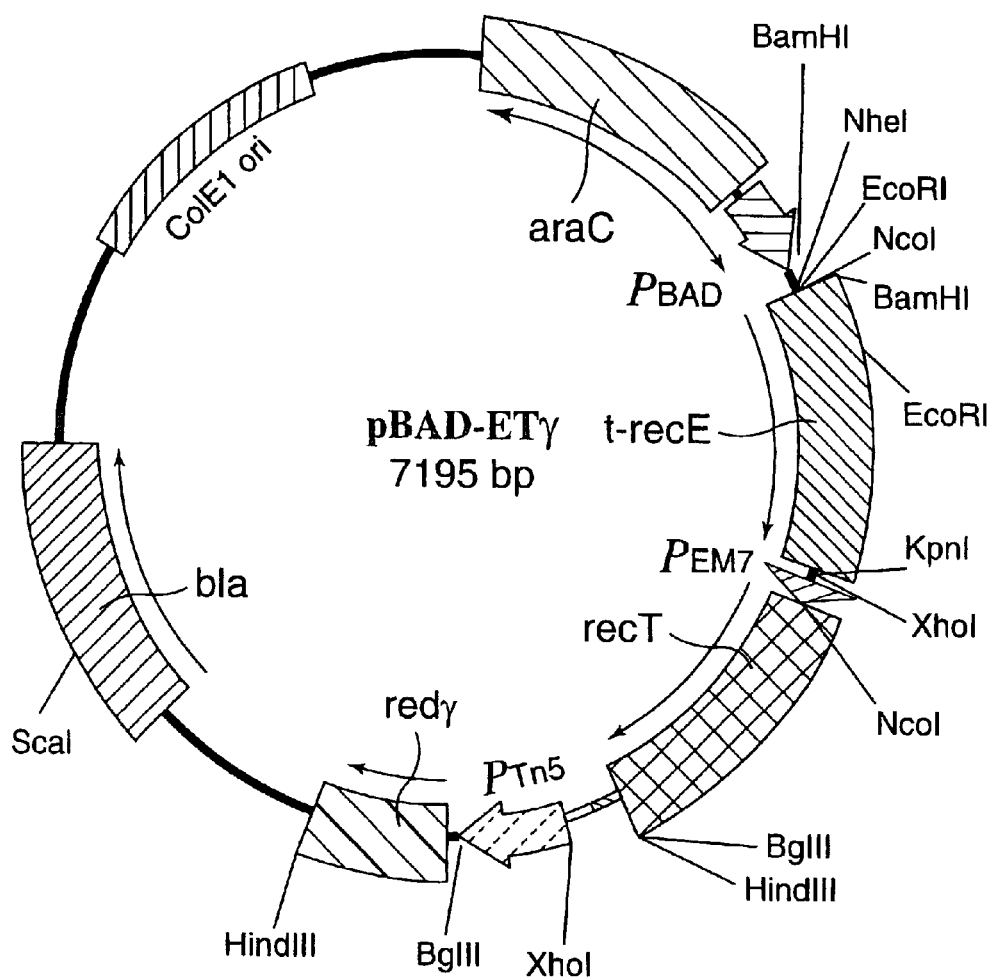

More preferably, the exonuclease inhibitor gene is selected from a nucleic acid molecule comprising
(a) the nucleic acid sequence from position 3588 (ATG) to 4002 (GTA) as depicted in FIG. 13B or SEQ ID No. 10 or 11,
(b) a nucleic acid encoding the same polypeptide within the degeneracy of the genetic code and/or
(c) a nucleic acid sequence which hybridizes under stringent conditions as defined above with the nucleic acid sequence from (a) and/or (b).

Surprisingly, it has been found that the expression of an exonuclease inhibitor gene in both recBC+ and recBC− strains leads to significant improvement of cloning efficiency.

The cloning method according to the present invention employs a homologous recombination between a first DNA molecule and a second DNA molecule. The first DNA molecule can be any DNA molecule that carries an origin of replication which is operative in the host cell, e.g. an *E. coli* replication origin. Further, the first DNA molecule is present in a form which is capable of being replicated in the host cell. The first DNA molecule, i.e. the vector, can be any extrachromosomal DNA molecule containing an origin of replication which is operative in said host cell, e.g. a plasmid including single, low, medium or high copy plasmids or other extrachromosomal circular DNA molecules based on cosmid, P1, BAC or PAC vector technology. Examples of such vectors are described, for example, by Sambrook et al. (Molecular Cloning, Laboratory Manual, 2nd Edition (1989), Cold Spring Harbor Laboratory Press) and Ioannou et al. (Nature Genet. 6 (1994), 84–89) or references cited therein. The first DNA molecule can also be a host cell chromosome, particularly the *E. coli* chromosome. Preferably, the first DNA molecule is a double-stranded DNA molecule.

The second DNA molecule is preferably a linear DNA molecule and comprises at least two regions of sequence homology, preferably of sequence identity to regions on the first DNA molecule. These homology or identity regions are preferably at least 15 nucleotides each, more preferably at least 20 nucleotides and, most preferably, at least 30 nucleotides each.

Especially good results were obtained when using sequence homology regions having a length of about 40 or more nucleotides, e.g. 60 or more nucleotides. The two sequence homology regions can be located on the linear DNA fragment so that one is at one end and the other is at the other end, however they may also be located internally. Preferably, also the second DNA molecule is a double-stranded DNA molecule.

The two sequence homology regions are chosen according to the experimental design. There are no limitations on which regions of the first DNA molecule can be chosen for the two sequence homology regions located on the second DNA molecule, except that the homologous recombination event cannot delete the origin of replication of the first DNA molecule. The sequence homology regions can be interrupted by non-identical sequence regions as long as sufficient sequence homology is retained for the homologous recombination reaction. By using sequence homology arms having non-identical sequence regions compared to the target site mutations such as substitutions, e.g. point mutations, insertions and/or deletions may be introduced into the target site by ET cloning.

The second foreign DNA molecule which is to be cloned in the bacterial cell may be derived from any source. For example, the second DNA molecule may be synthesized by a nucleic acid amplification reaction such as a PCR where both of the DNA oligonucleotides used to prime the amplification contain in addition to sequences at the 3'-ends that serve as a primer for the amplification, one or the other of the two homology regions. Using oligonucleotides of this design, the DNA product of the amplification can be any DNA sequence suitable for amplification and will additionally have a sequence homology region at each end.

A specific example of the generation of the second DNA molecule is the amplification of a gene that serves to convey a phenotypic difference to the bacterial host cells, in particular, antibiotic resistance. A simple variation of this procedure involves the use of oligonucleotides that include other sequences in addition to the PCR primer sequence and the sequence homology region. A further simple variation is the use of more than two amplification primers to generate the amplification product. A further simple variation is the use of more than one amplification reaction to generate the amplification product. A further variation is the use of DNA fragments obtained by methods other than PCR, for example, by endonuclease or restriction enzyme cleavage to linearize fragments from any source of DNA.

It should be noted that the second DNA molecule is not necessarily a single species of DNA molecule. It is of course possible to use a heterogenous population of second DNA molecules, e.g. to generate a DNA library, such as a genomic or cDNA library.

The method of the present invention may comprise the contacting of the first and second DNA molecules in vivo. In one embodiment of the present invention the second DNA fragment is transformed into a bacterial strain that already harbors the first vector DNA molecule. In a different embodiment, the second DNA molecule and the first DNA molecule are mixed together in vitro before co-transformation in the bacterial host cell. These two embodiments of the present invention are schematically depicted in FIG. 1. The method of transformation can be any method known in the art (e.g. Sambrook et al. supra). The preferred method of transformation or co-transformation, however, is electroporation.

Figure 2:
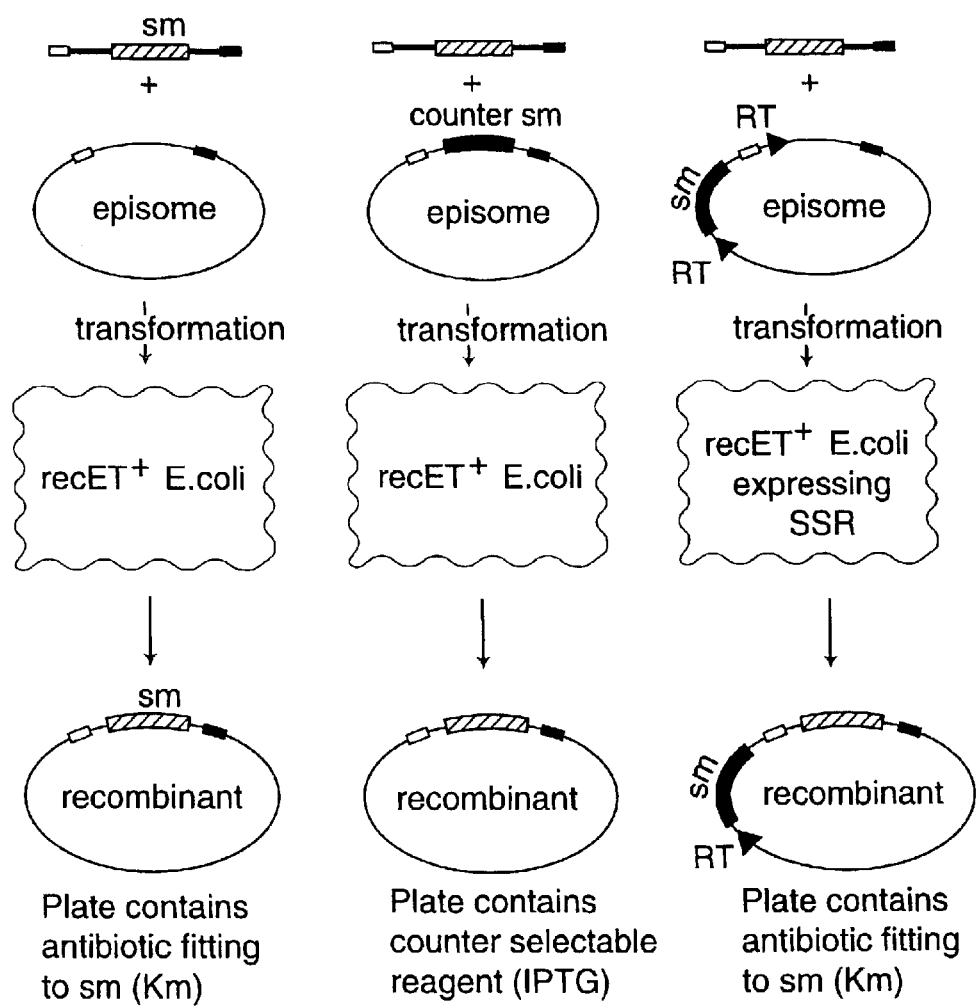

After contacting the first and second DNA molecules under conditions which favour homologous recombination between first and second DNA molecules via the ET cloning mechanism a host cell is selected, in which homologous recombination between said first and second DNA molecules has occurred. This selection procedure can be carried out by several different methods. In the following three preferred selection methods are depicted in FIG. 2 and described in detail below.

In a first selection method a second DNA fragment is employed which carries a gene for a marker placed between the two regions of sequence homology wherein homologous recombination is detectable by expression of the marker gene. The marker gene may be a gene for a phenotypic marker which is not expressed in the host or from the first DNA molecule. Upon recombination by ET cloning, the change in phenotype of the host strain conveyed by the stable acquisition of the second DNA fragment identifies the ET cloning product.

In a preferred case, the phenotypic marker is a gene that conveys resistance to an antibiotic, in particular, genes that convey resistance to kanamycin, ampillicin, chloramphenicol, tetracyclin or any other substance that shows bacteriocidal or bacteriostatic effects on the bacterial strain employed.

A simple variation is the use of a gene that complements a deficiency present within the bacterial host strain employed. For example, the host strain may be mutated so that it is incapable of growth without a metabolic supplement. In the absence of this supplement, a gene on the second DNA fragment can complement the mutational defect thus permitting growth. Only those cells which contain the episome carrying the intended DNA rearrangement caused by the ET cloning step will grow.

In another example, the host strain carries a phenotypic marker gene which is mutated so that one of its codons is a stop codon that truncates the open reading frame. Expression of the full length protein from this phenotypic marker gene requires the introduction of a suppressor tRNA gene which, once expressed, recognizes the stop codon and permits translation of the full open reading frame. The suppressor tRNA gene is introduced by the ET cloning step and successful recombinants identified by selection for, or identification of, the expression of the phenotypic marker gene. In these cases, only those cells which contain the intended DNA rearrangement caused by the ET cloning step will grow.

A further simple variation is the use of a reporter gene that conveys a readily detectable change in colony colour or morphology. In a preferred case, the green fluorescence protein (GFP) can be used and colonies carrying the ET cloning product identified by the fluorescence emissions of GFP. In another preferred case, the lacZ gene can be used and colonies carrying the ET cloning product identified by a blue colony colour when X-gal is added to the culture medium.

In a second selection method the insertion of the second DNA fragment into the first DNA molecule by ET cloning alters the expression of a marker present on the first DNA molecule. In this embodiment the first DNA molecule contains at least one marker gene between the two regions of sequence homology and homologous recombination may be detected by an altered expression, e.g. lack of expression of the marker gene.

In a preferred application, the marker present on the first DNA molecule is a counter-selectable gene product, such as the sacB, ccdB or tetracycline-resistance genes. In these cases, bacterial cells that carry the first DNA molecule unmodified by the ET cloning step after transformation with the second DNA fragment, or co-transformation with the second DNA fragment and the first DNA molecule, are plated onto a medium so the expression of the counter-selectable marker conveys a toxic or bacteriostatic effect on the host. Only those bacterial cells which contain the first DNA molecule carrying the intended DNA rearrangement caused by the ET cloning step will grow.

In another preferred application, the first DNA molecule carries a reporter gene that conveys a readily detectable change in colony colour or morphology. In a preferred case, the green fluorescence protein (GFP) can be present on the first DNA molecule and colonies carrying the first DNA molecule with or without the ET cloning product can be distinguished by differences in the fluorescence emissions of GFP. In another preferred case, the lacZ gene can be present on the first DNA molecule and colonies carrying the first DNA molecule with or without the ET cloning product identified by a blue or white colony colour when X-gal is added to the culture medium.

In a third selection method the integration of the second DNA fragment into the first DNA molecule by ET cloning removes a target site for a site specific recombinase, termed here an RT (for recombinase target) present on the first DNA molecule between the two regions of sequence homology. A homologous recombination event may be detected by removal of the target site.

In the absence of the ET cloning product, the RT is available for use by the corresponding site specific recombinase. The difference between the presence or not of this RT is the basis for selection of the ET cloning product. In the presence of this RT and the corresponding site specific recombinase, the site specific recombinase mediates recombination at this RT and changes the phenotype of the host so that it is either not able to grow or presents a readily observable phenotype. In the absence of this RT, the corresponding site specific recombinase is not able to mediate recombination.

In a preferred case, the first DNA molecule to which the second DNA fragment is directed, contains two RTs, one of which is adjacent to, but not part of, an antibiotic resistance gene. The second DNA fragment is directed, by design, to remove this RT. Upon exposure to the corresponding site specific recombinase, those first DNA molecules that do not carry the ET cloning product will be subject to a site specific recombination reaction between the RTs that remove the antibiotic resistance gene and therefore the first DNA molecule fails to convey resistance to the corresponding antibiotic. Only those first DNA molecules that contain the ET cloning product, or have failed to be site specifically recombined for some other reason, will convey resistance to the antibiotic.

In another preferred case, the RT to be removed by ET cloning of the second DNA fragment is adjacent to a gene that complements a deficiency present within the host strain employed. In another preferred case, the RT to be removed by ET cloning of the second DNA fragment is adjacent to a reporter gene that conveys a readily detectable change in colony colour or morphology.

In another preferred case, the RT to be removed by ET cloning of the second DNA fragment is anywhere on a first episomal DNA molecule and the episome carries an origin of replication incompatible with survival of the bacterial host cell if it is integrated into the host genome. In this case the host genome carries a second RT, which may or may not be a mutated RT so that the corresponding site specific recombinase can integrate the episome, via its RT, into the RT sited in the host genome. Other preferred RTs include RTs for site specific recombinases of the resolvase/transposase class. RTs include those described from existing examples of site specific recombination as well as natural or mutated variations thereof.

The preferred site specific recombinases include Cre, FLP, Kw or any site specific recombinase of the integrase class. Other preferred site specific recombinases include site specific recombinases of the resolvase/transposase class.

There are no limitations on the method of expression of the site specific recombinase in the host cell. In a preferred method, the expression of the site specific recombinase is regulated so that expression can be induced and quenched according to the optimisation of the ET cloning efficiency. In this case, the site specific recombinase gene can be either integrated into the host genome or carried on an episome. In another preferred case, the site specific recombinase is expressed from an episome that carries a conditional origin of replication so that it can be eliminated from the host cell.

In another preferred case, at least two of the above three selection methods are combined. A particularly preferred case involves a two-step use of the first selection method above, followed by use of the second selection method. This combined use requires, most simply, that the DNA fragment to be cloned includes a gene, or genes that permits the identification, in the first step, of correct ET cloning products by the acquisition of a phenotypic change. In a second step, expression of the gene or genes introduced in the first step is altered so that a second round of ET cloning products can be identified. In a preferred example, the gene employed is the tetracycline resistance gene and the first step ET cloning products are identified by the acquisition of tetracycline resistance. In the second step, loss of expression of the tetracycline gene is identified by loss of sensitivity to nickel chloride, fusaric acid or any other agent that is toxic to the host cell when the tetracycline gene is expressed. This two-step procedure permits the identification of ET cloning products by first the integration of a gene that conveys a phenotypic change on the host, and second by the loss of a related phenotypic change, most simply by removal of some of the DNA sequences integrated in the first step. Thereby the genes used to identify ET cloning products can be inserted and then removed to leave ET cloning products that are free of these genes.

In a further embodiment of the present invention the ET cloning may also be used for a recombination method comprising the steps of a) providing a source of RecE and RecT, or Redα and Redβ, proteins, b) contacting a first DNA molecule which is capable of being replicated in a suitable host cell with a second DNA molecule comprising at least two regions of sequence homology to regions on the first DNA molecule, under conditions which favour homologous recombination between said first and second DNA molecules and c) selecting DNA molecules in which a homologous recombination between said first and second DNA molecules has occurred.

The source of RecE and RecT, or Redα and Redβ, proteins may be either purified or partially purified RecE and RecT, or Redα and Redβ, proteins or cell extracts comprising RecE and RecT, or Redα and Redβ, proteins.

The homologous recombination event in this embodiment may occur in vitro, e.g. when providing a cell extract containing further components required for homologous recombination. The homologous recombination event, however, may also occur in vivo, e.g. by introducing RecE and RecT, or Redα and Redβ, proteins or the extract in a host cell (which may be recET positive or not, or redαβ positive or not) and contacting the DNA molecules in the host cell. When the recombination occurs in vitro the selection of DNA molecules may be accomplished by transforming the recombination mixture in a suitable host cell and selecting for positive clones as described above. When the recombination occurs in vivo the selection methods as described above may directly be applied.

A further subject matter of the invention is the use of cells, preferably bacterial cells, most preferably, E. coli cells capable of expressing the recE and recT, or redα and redβ, genes as a host cell for a cloning method involving homologous recombination.

Still a further subject matter of the invention is a vector system capable of expressing recE and recT, or redα and redβ, genes in a host cell and its use for a cloning method involving homologous recombination. Preferably, the vector system is also capable of expressing an exonuclease inhibitor gene as defined above, e.g. the λ redγ gene. The vector system may comprise at least one vector. The recE and recT, or redα and redβ, genes are preferably located on a single vector and more preferably under control of a regulatable promoter which may be the same for both genes or a single promoter for each gene. Especially preferred is a vector system which is capable of overexpressing the recT, or redβ, gene versus the recE, or redα, gene.

Still a further subject matter of the invention is the use of a source of RecE and RecT, or Redα and Redβ, proteins for a cloning method involving homologous recombination.

A still further subject matter of the invention is a reagent kit for cloning comprising (a) a host cell, preferably a bacterial host cell, (b) means of expressing recE and recT, or redα and redβ, genes in said host cell, e.g. comprising a vector system, and (c) a recipient cloning vehicle, e.g. a vector, capable of being replicated in said cell.

On the one hand, the recipient cloning vehicle which corresponds to the first DNA molecule of the process of the invention can already be present in the bacterial cell. On the other hand, it can be present separated from the bacterial cell.

In a further embodiment the reagent kit comprises (a) a source for RecE and RecT, or Redα and Redβ, proteins and (b) a recipient cloning vehicle capable of being propagated in a host cell and (c) optionally a host cell suitable for propagating said recipient cloning vehicle.

The reagent kit furthermore contains, preferably, means for expressing a site specific recombinase in said host cell, in particular, when the recipient ET cloning product contains at least one site specific recombinase target site. Moreover, the reagent kit can also contain DNA molecules suitable for use as a source of linear DNA fragments used for ET cloning, preferably by serving as templates for PCR generation of the linear fragment, also as specifically designed DNA vectors from which the linear DNA fragment is released by restriction enzyme cleavage, or as prepared linear fragments included in the kit for use as positive controls or other tasks. Moreover, the reagent kit can also contain nucleic acid amplification primers comprising a region of homology to said vector. Preferably, this region of homology is located at the 5'-end of the nucleic acid amplification primer.

The invention is further illustrated by the following Sequence listings, Figures and Examples.

SEQ ID NO. 1: shows the nucleic acid sequence of the plasmid pBAD24-rec ET (FIG. 7).

SEQ ID NOs 2/3: show the nucleic acid and amino acid sequences of the truncated recE gene (t-recE) present on pBAD24-recET at positions 1320–2162.

SEQ ID NOs 4/5: show the nucleic acid and amino acid sequences of the recT gene present on pBAD24-recET at position 2155–2972.

SEQ ID NOs 6/7: show the nucleic acid and amino acid sequences of the araC gene present on the complementary stand to the one shown of pBAD24-recET at positions 974–996.

SEQ ID NOs 8/9: show the nucleic acid an amino acid sequences of the bla gene present on pBAD24-recET at positions 3493–4353.

Figure 13D:
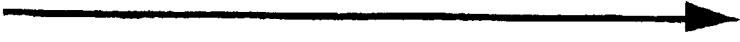

SEQ ID NO 10: shows the nucleic acid sequence of the plasmid pBAD-ETγ (FIG. 13).

SEQ ID No 11: shows the nucleic acid sequence of the plasmid pBAD-αβγ (FIG. 14) as well as the coding regions for the genes redα (1320–200), redβ (2086–2871) and redγ (3403–3819).

SEQ ID NOs 12–14: show the amino acid sequences of the Redα, Redβ and Redγ proteins, respectively. The redγ sequence is present on each of pBAD-ETγ (FIG. 13) and pBAD-αβγ (FIG. 14).

FIG. 1

A preferred method for ET cloning is shown by diagram. The linear DNA fragment to be cloned is synthesized by PCR using oligonucleotide primers that contain a left homology arm chosen to match sequences in the recipient episome and a sequence for priming in the PCR reaction, and a right homology arm chosen to match another sequence in the recipient episome and a sequence for priming in the PCR reaction. The product of the PCR reaction, here a selectable marker gene (sm1), is consequently flanked by the left and right homology arms and can be mixed together in vitro with the episome before co-transformation, or transformed into a host cell harboring the target episome. The host cell contains the products of the recE and recT genes. ET cloning products are identified by the combination of two selectable markers, sm1 and sm2 on the recipient episome.

FIG. 2

Three ways to identify ET cloning products are depicted. The first, (on the left of the figure), shows the acquisition, by ET cloning, of a gene that conveys a phenotypic difference to the host, here a selectable marker gene (sm). The second (in the centre of the figure) shows the loss, by ET cloning, of a gene that conveys a phenotypic difference to the host, here a counter selectable marker gene (counter-sm). The third shows the loss of a target site (RT, shown as triangles on the circular episome) for a site specific recombinase (SSR), by ET cloning. In this case, the correct ET cloning product deletes one of the target sites required by the SSR to delete a selectable marker gene (sm). The failure of the SSR to delete the sm gene identifies the correct ET cloning product.

FIG. 3

A simple example of ET cloning is presented.

(a) Top panel—PCR products (left lane) synthesized from oligonucleotides designed as described in FIG. 1 to amplify by PCR a kanamycin resistance gene and to be flanked by homology arms present in the recipient vector, were mixed in vitro with the recipient vector (2nd lane) and cotransformed into a recET+ E. coli host. The recipient vector carried an ampillicin resistance gene. (b) Transformation of the sbcA E. coli strain JC9604 with either the PCR product alone (0.2 μg) or the vector alone (0.3 μg) did not convey resistance to double selection with ampicillin and kanamycin (amp+kan), however cotransformation of both the PCR product and the vector produced double resistant colonies. More than 95% of these colonies contained the correct ET cloning product where the kanamycin gene had precisely integrated into the recipient vector according to the choice of homology arms. The two lanes on the right of (a) show Pvu II restriction enzyme digestion of the recipient vector before and after ET cloning. (c) As for b, except that six PCR products (0.2 μg each) were cotransformed with pSVpaZ11 (0.3 μg each) into JC9604 and plated onto Amp+Kan plates or Amp plates. Results are plotted as Amp+ Kan-resistant colonies, representing recombination products, divided by Amp-resistant colonies, representing the plasmid transformation efficiency of the competent cell preparation, ×10$^6$. The PCR products were equivalent to the a-b PCR product except that homology arm lengths were varied. Results are from five experiments that used the same batches of competent cells and DNAs. Error bars represent standard deviation. (d) Eight products flanked by 50 bp homology arms were cotransformed with pSVpaZ11 into JC9604. All eight PCR products contained the same left homology arm and amplified neo gene. The right homology arms were chosen from the pSVpaZ11 sequence to be adjacent to (0), or at increasing distances (7–3100 bp), from the left. Results are from four experiments.

Figure 4A:
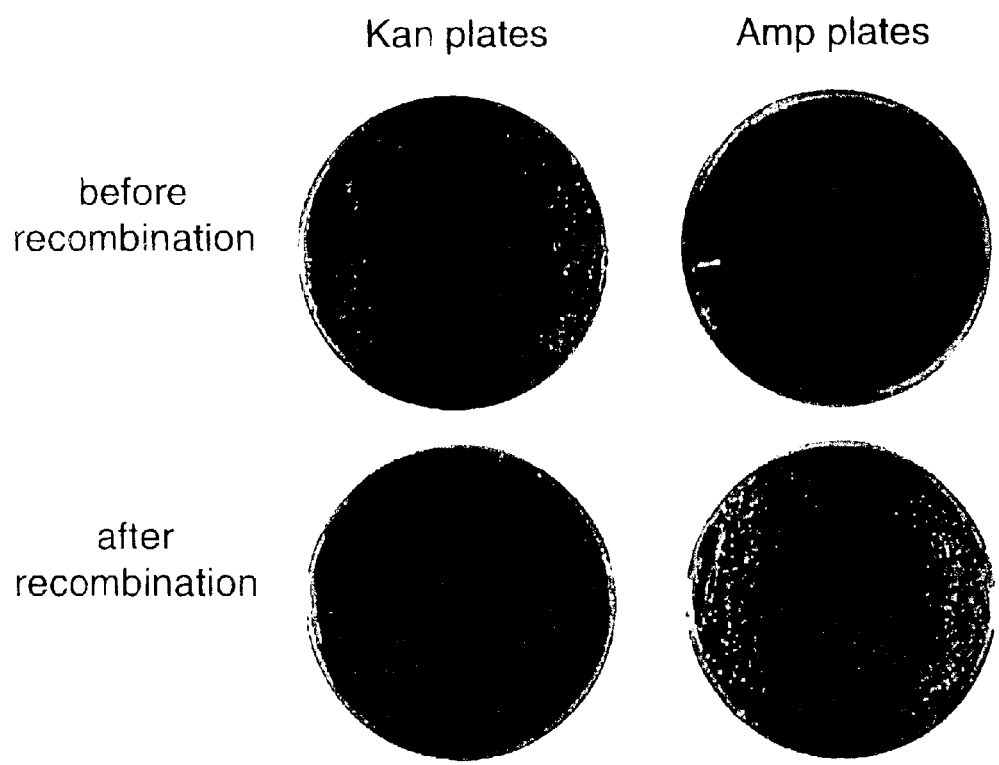

FIGS. 4(a) and (b)

ET cloning in an approximately 100 kb P1 vector to exchange the selectable marker.

A P1 clone which uses a kanamycin resistance gene as selectable marker and which contains at least 70 kb of the mouse Hox a gene cluster was used. Before ET cloning, this episome conveys kanamycin resistance (top panel, upper left) to its host E. coli which are ampillicin sensitive (top panel, upper right). A linear DNA fragment designed to replace the kanamycin resistance gene with an ampillicin resistance gene was made by PCR as outlined in FIG. 1 and transformed into E. coli host cells in which the recipient Hox a/P1 vector was resident. ET cloning resulted in the deletion of the kanamycin resistance gene, and restoration of kanamycin sensitivity (top panel, lower left) and the acquisition of ampillicin resistance (top panel, lower right). Precise DNA recombination was verified by restriction digestion and Southern blotting analyses of isolated DNA before and after ET cloning (lower panel).

Figure 5A:
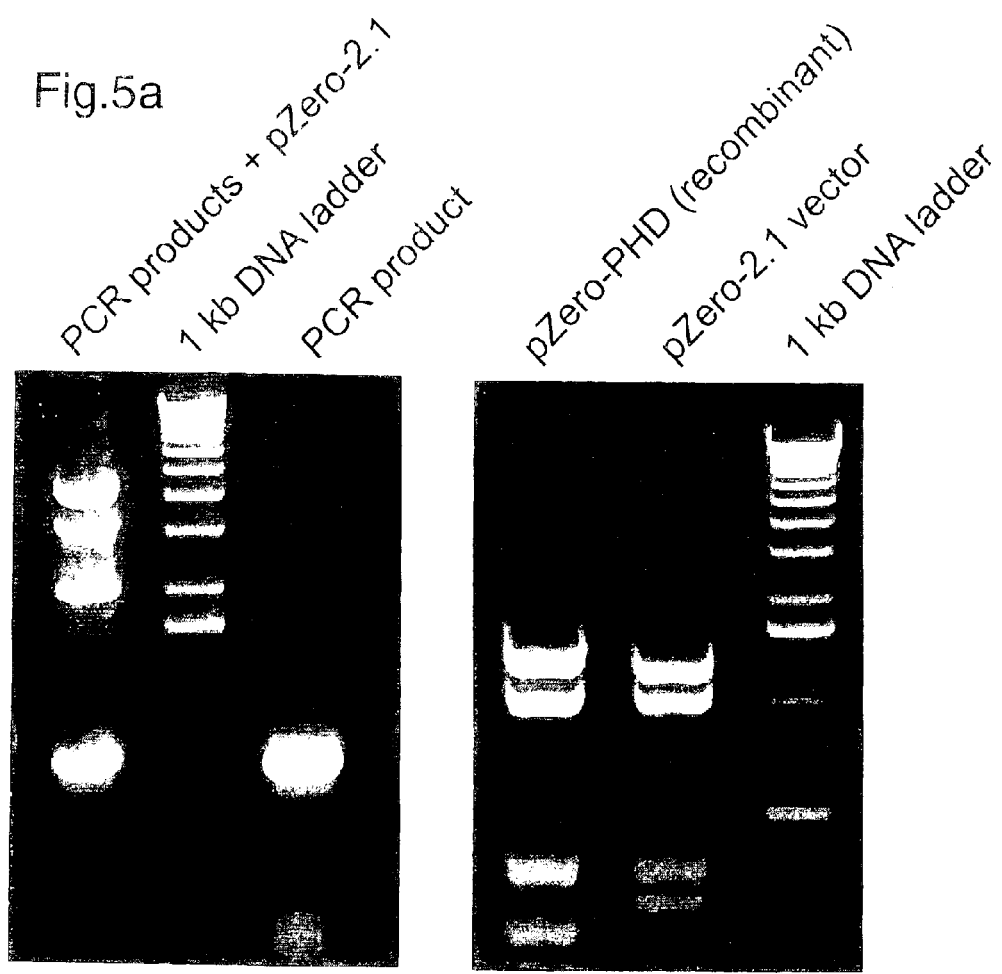

FIGS. 5(a) and (b)

ET cloning to remove a counter selectable marker

A PCR fragment (upper panel, left, third lane) made as outlined in FIGS. 1 and 2 to contain the kanamycin resistance gene was directed by its chosen homology arms to delete the counter selectable ccdB gene present in the vector, pZero-2.1. The PCR product and the pZero vector were mixed in vitro (upper panel, left, 1st lane) before cotransformation into a recE/recT+ E. coli host. Transformation of pZero-2.1 alone and plating onto kanamycin selection medium resulted in little colony growth (lower panel, left). Cotransformation of pZero-2.1 and the PCR product presented ET cloning products (lower panel, right) which showed the intended molecular event as visualized by Pvu II digestion (upper panel, right).

FIG. 6

ET cloning mediated by inducible expression of recE and recT from an episome.

RecE/RecT mediate homologous recombination between linear and circular DNA molecules. (a) The plasmid pBAD24-recET was transformed into E. coli JC5547, and then batches of competent cells were prepared after induction of RecE/RecT expression by addition of L-arabinose for the times indicated before harvesting. A PCR product, made using oligonucleotides e and f to contain the chloramphenicol resistance gene (cm) of pMAK705 and 50 bp homology arms chosen to flank the ampicillin resistance gene (bla) of pBAD24-recET, was then transformed and recombinants identified on chloramphenicol plates. (b) Arabinose was added to cultures of pBAD24-recET transformed JC5547 for different times immediately before harvesting for competent cell preparation. Total protein expression was analyzed by SDS-PAGE and Coomassie blue staining. (c) The number of chloramphenicol resistant colonies per μg of PCR product was normalized against a control for transformation efficiency, determined by including 5 pg pZero2.1, conveying kanamycin resistance, in the transformation and plating an aliquot onto Kan plates.

FIG. 7A

The plasmid pBAD24-recET is shown by diagram. The plasmid contains the genes recE (in a truncated form) and recT under control of the inducible BAD promoter ($P_{BAD}$) The plasmid further contains an ampillicin resistance gene ($Amp^r$) and an araC gene.

FIGS. 7B through 7N

The nucleic acid sequence and the protein coding portions of pBAD24-recET are depicted.

FIG. 8

Figure 8A:
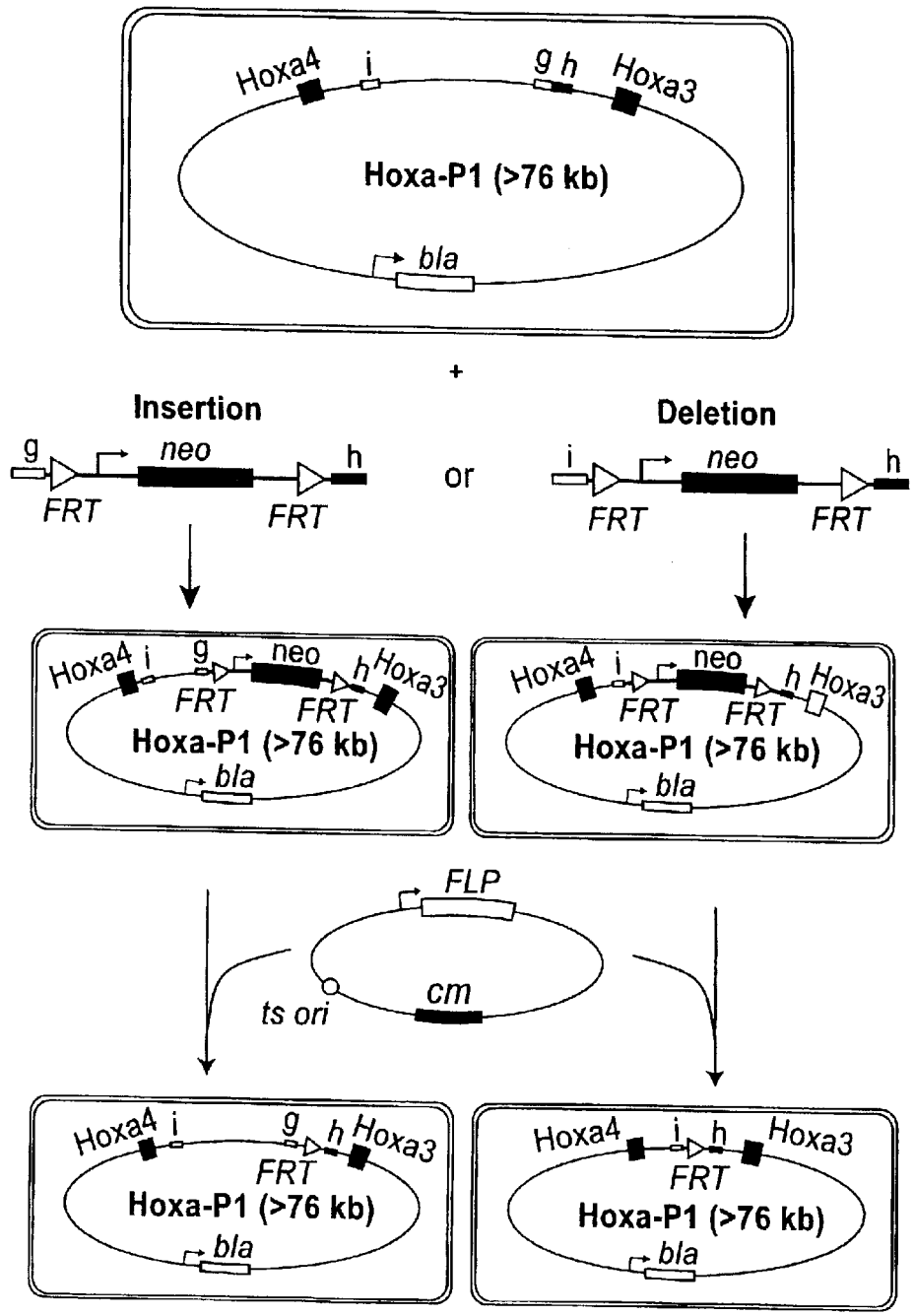
Figure 8B:
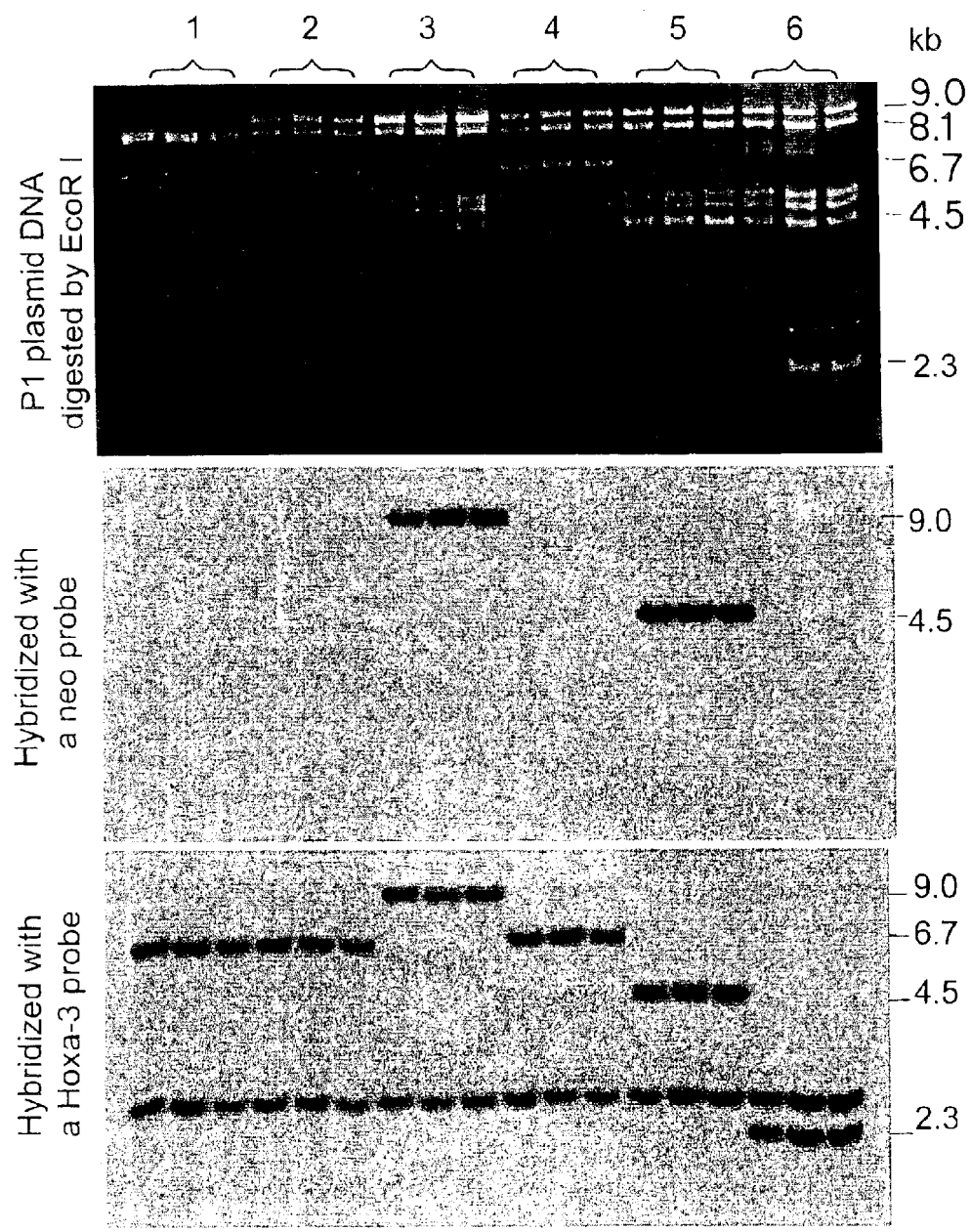

Manipulation of a large E. coli episome by multiple recombination steps. FIG. 8a depicts the scheme of the recombination reactions. A P1 clone of the Mouse Hoxa complex, resident in JC9604, was modified by recombination with PCR products that contained the neo gene and two Flp recombination targets (FRTs). The two PCR products were identical except that one was flanked by g and h homology arms (insertion), and the other was flanked by i and h homology arms (deletion). In a second step, the neo gene was removed by Flp recombination between the FRTs by transient transformation of a Flp expression plasmid based on the pSC101 temperature-sensitive origin (ts ori). FIG. 8b (upper panel): ethidium bromide stained agarose gel showing EcoR1 digestions of P1 DNA preparations from three independent colonies for each step. FIG. 8b (middle panel): a Southern blot of the upper panel hybridized with a neo gene probe. FIG. 8b (lower panel): a Southern blot of the upper panel hybridized with a Hoxa3 probe to visualize the site of recombination. Lane 1 in each of the panels shows the original Hoxa3 P1 clone grown in E. coli strain NS3145. Lane 2 in each of the panels shows that replacement of the Tn903 kanamycin resistance gene in the P1 vector with an ampicillin resistance gene, increased the 8.1 kb band (lane 1) to 9.0 kb. Lane 3 in each of the panels shows that insertion of the Tn5-neo gene with g-h homology arms upstream of Hoxa3, increased the 6.7 kb band (lanes 1,2) to 9.0 kb. Lane 4 in each of the panels shows that Flp recombinase deleted the g-h neo gene reducing the 9.0 kb band (lane 3) back to 6.7 kb. Lane 5 in each of the panels shows that deletion of 6 kb of Hoxa3–4 intergenic DNA by replacement with the i-h neo gene, decreased the 6.7 kb band (lane 2) to 4.5 kb. Lane 6 in each of the panels shows that Flp recombinase deleted the i-h neo gene reducing the 4.5 kb band to 2.3 kb.

FIG. 9

Figure 9A:
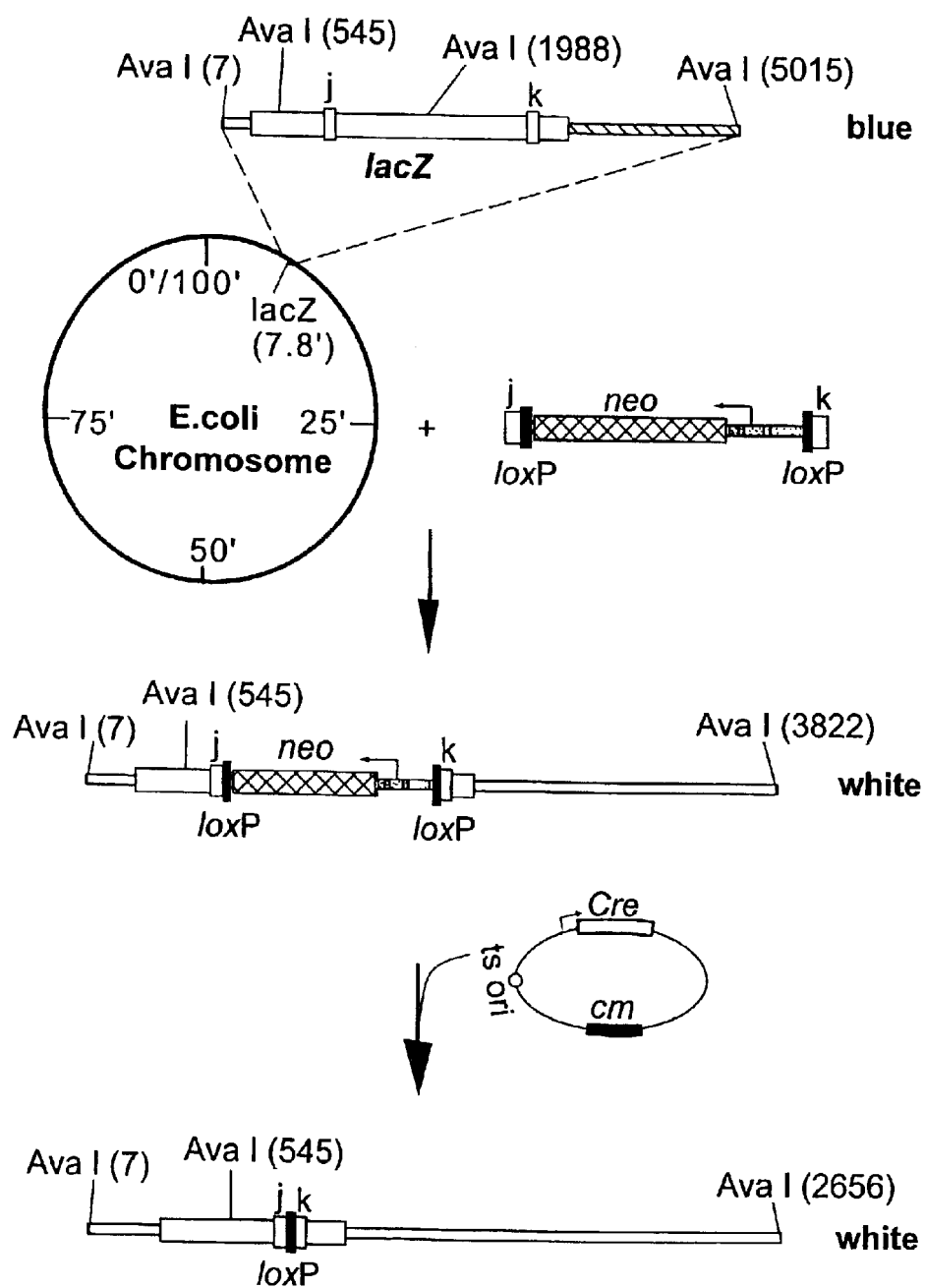
Figure 9B:
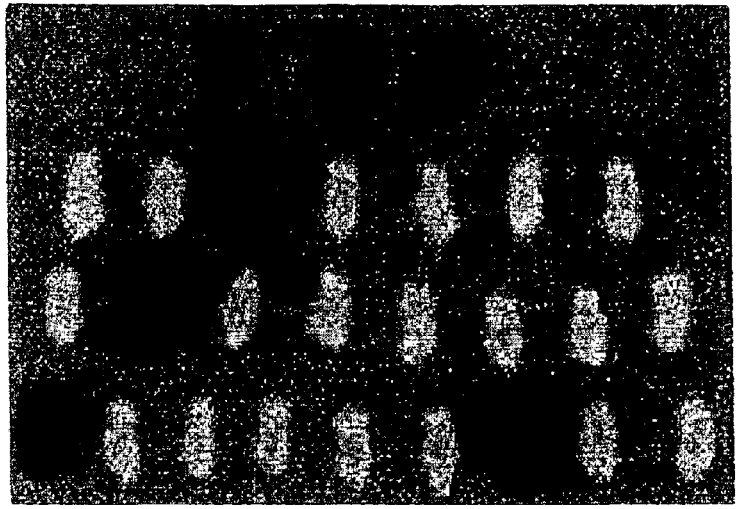
Figure 9C:
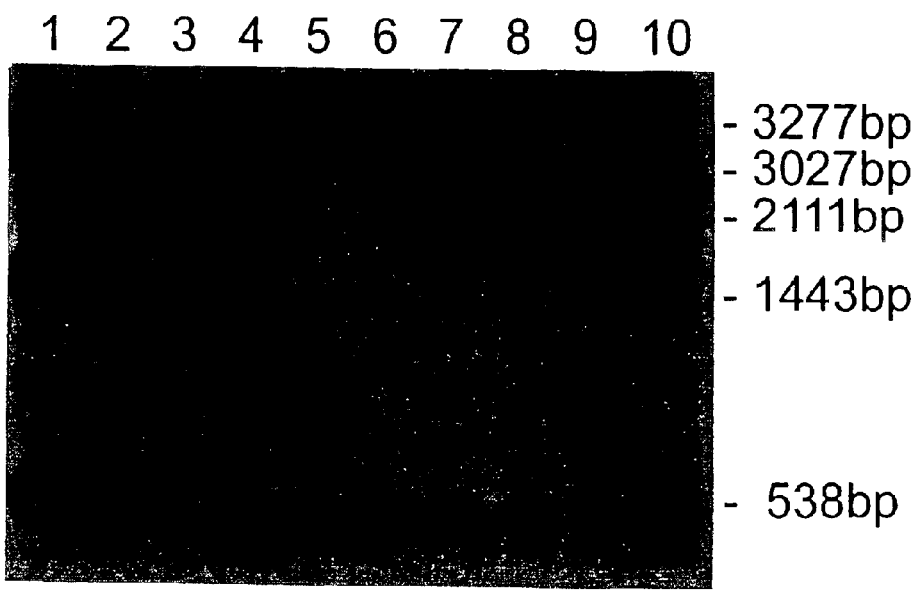

Manipulation of the E. coli chromosome. FIG. 9a depicts the scheme of the recombination reactions. The endogenous lacZ gene of JC9604 at 7.8' of the E. coli chromosome, shown in expanded form with relevant Ava I sites and coordinates, was targeted by a PCR fragment that contained the neo gene flanked by homology arms j and k, and loxP sites, as depicted. Integration of the neo gene removed most of the lacZ gene including an Ava I site to alter the 1443 and 3027 bp bands into a 3277 bp band. In a second step, the neo gene was removed by Cre recombination between the loxPs by transient transformation of a Cre expression plasmid based on the pSC101 temperature-sensitive origin (ts ori). Removal of the neo gene by Cre recombinase reduces the 3277 band to 2111 bp. FIG. 9b shows β-galactosidase expression evaluated by streaking colonies on X-Gal plates. The top row of three streaks show β-galactosidase expression in the host JC9604 strain (w.t.), the lower three rows (Km) show 24 independent primary colonies, 20 of which display a loss of β-galactosidase expression indicactive of the intended recombination event. FIG. 9c shows the results from Southern analysis of E. coli chromosomal DNA digested with Ava I using a random primed probe made from the entire lacZ coding region; lanes 1,2, w.t.; lanes 3–6, four independent white colonies after integration of the j-k neo gene; lanes 7–10; the same four colonies after transient transformation with the Cre expression plasmid.

FIG. 10

Figure 10B:
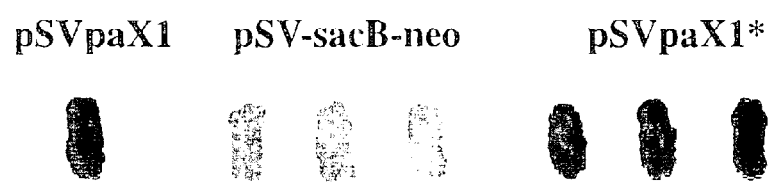
Figure 10C:
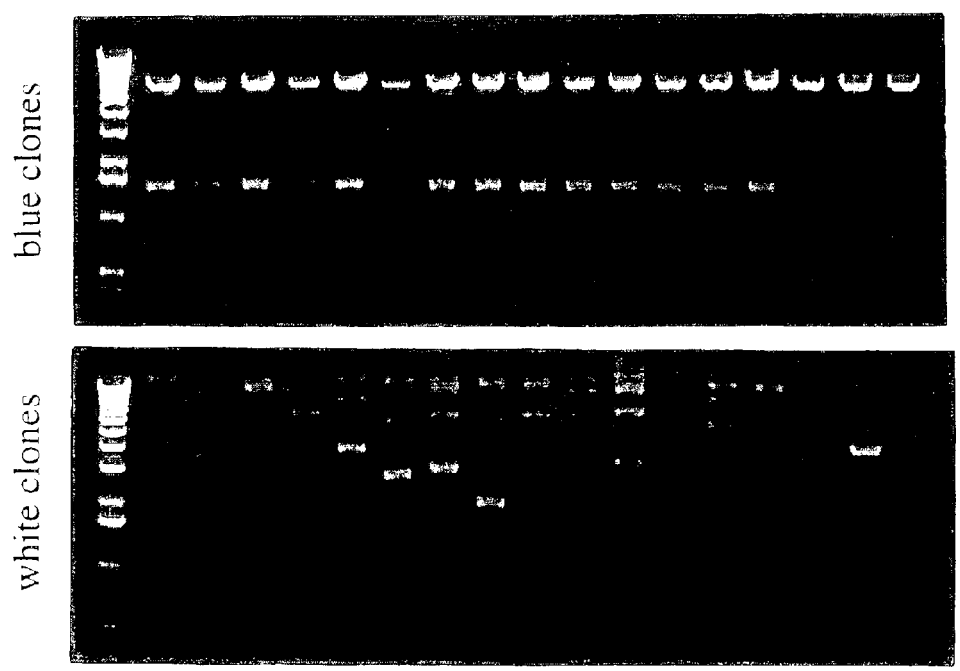

Two rounds of ET cloning to introduce a point mutation. FIG. 10a depicts the scheme of the recombination reactions. The lacZ gene of pSVpaX1 was disrupted in JC9604lacZ, a strain made by the experiment of FIG. 9 to ablate endogenous lacZ expression and remove competitive sequences, by a sacB-neo gene cassette, synthesized by PCR to plB279 and flanked by l and m homology arms. The recombinants, termed pSV-sacB-neo, were selected on Amp+Kan plates. The lacZ gene of pSV-sacB-neo was then repaired by a PCR fragment made from the intact lacZ gene using l and m homology arms. The m homology arm included a silent C to G change that created a BamH1 site. The recombinants, termed pSVpaX1, were identified by counter selection against the sacB gene using 7% sucrose. FIG. 10b shows that β-galactosidase expression from pSVpaX1 was disrupted in pSV-sacB-neo and restored in pSVpaX1*. Expression was analyzed on X-gal plates. Three independent colonies of each pSV-sacB-neo and pSVpaX1* are shown. FIG. 10c shows Ethidium bromide stained agarose gels of BamH1 digested DNA prepared from independent colonies taken after counter selection with sucrose. All β-galactosidase expressing colonies (blue) contained the introduced BamH1 restriction site (upper panel). All white colonies displayed large rearrangements and no product carried the diagnostic 1.5 kb BamH1 restriction fragment (lower panel).

FIG. 11

Figure 11A:
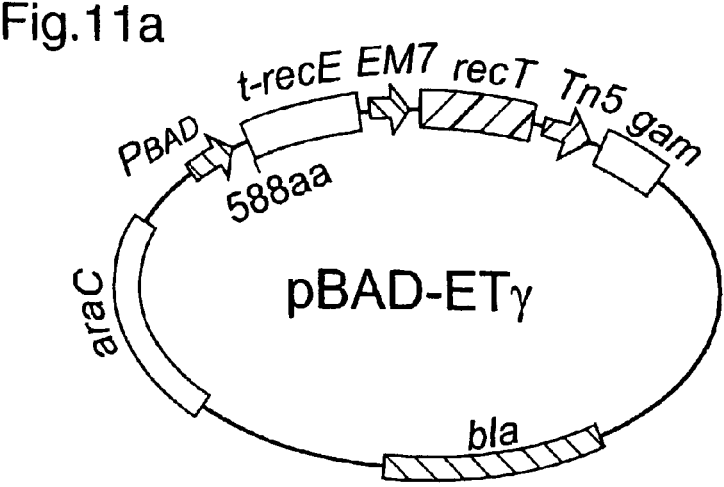
Figure 11A:
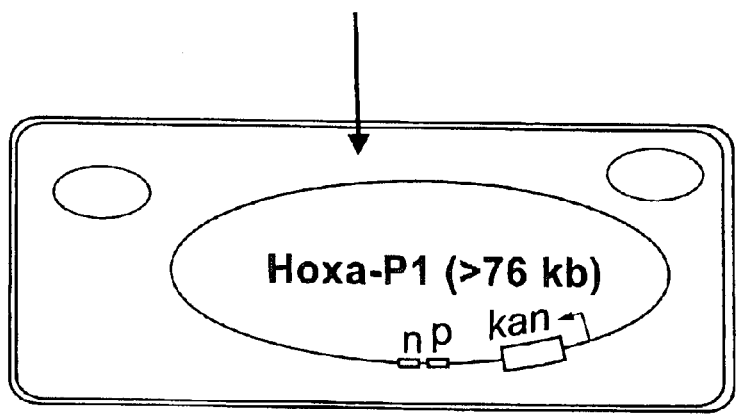
Figure 11A:
Figure 11A:
Figure 11A:
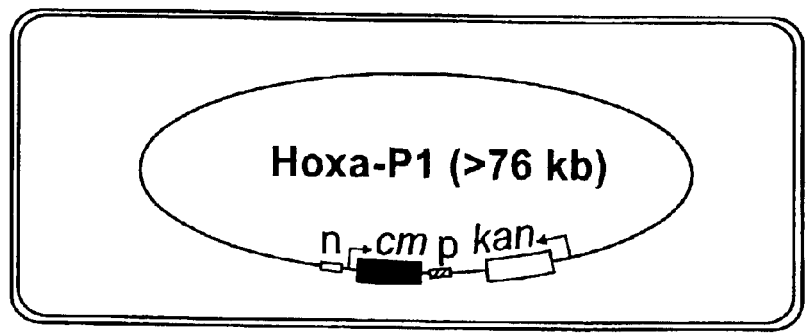
Figure 11B:
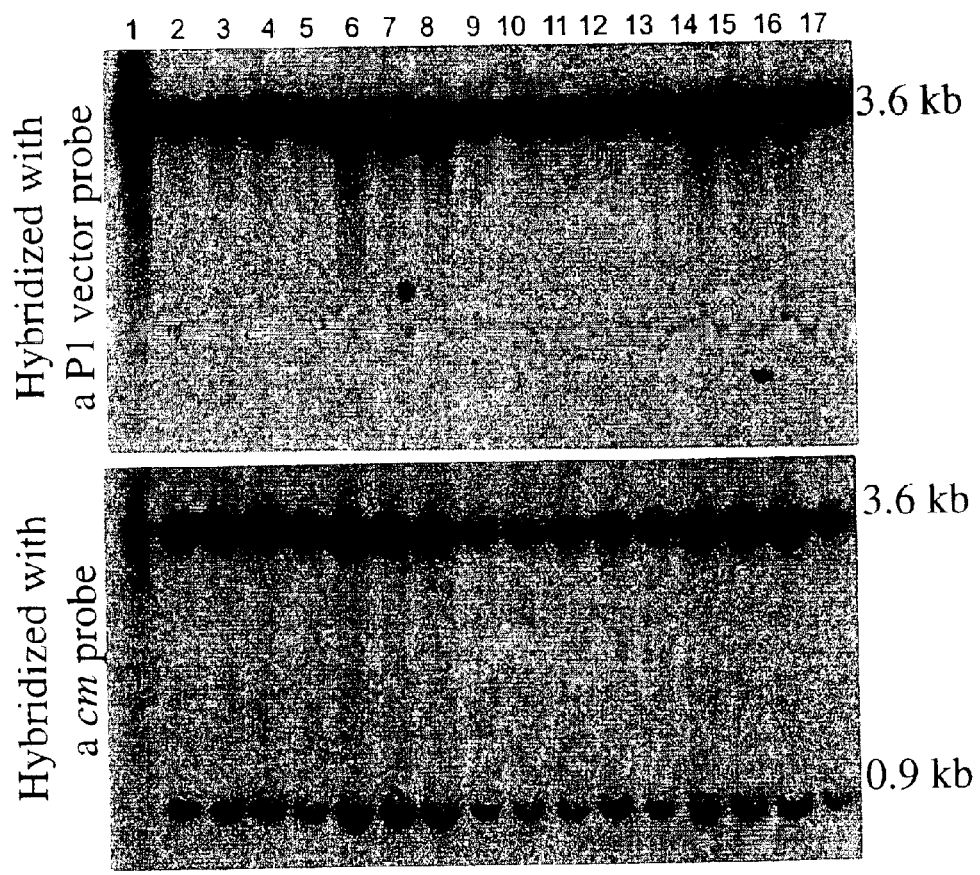

Transference of ET cloning into a recBC+ host to modify a large episome. FIG. 11a depicts the plasmid, pBAD-ETγ, which carries the mobile ET system, and the strategy employed to target the Hoxa P1 episome. pBAD-ETγ is based on pBAD24 and includes (i) the truncated recE gene (t-recE) under the arabinose-inducible $P_{BAD}$ promoter; (ii) the recT gene under the EM7 promoter; and (iii) the redγ gene under the Tn5 promoter. It was transformed into NS3145, a recA E. coli strain which contained the Hoxa P1 episome. After arabinose induction, competent cells were prepared and transformed with a PCR product carrying the chloramphenicol resistance gene (cm) flanked by n and p homology arms. n and p were chosen to recombine with a segment of the P1 vector. FIG. 11b shows the results from Southern blots of Pvu II digested DNAs hybridized with a probe made from the P1 vector to visualize the recombination target site (upper panel) and a probe made from the chloramphenicol resistance gene (lower panel). Lane 1, DNA prepared from cells harboring the Hoxa P1 episome before ET cloning. Lanes 2–17, DNA prepared from 16 independent chloramphenicol resistant colonies.

FIG. 12

Comparison of ET cloning using the recE/recT genes in pBAD-ETγ with redα/redβ genes in pBAD-αβγ.

The plasmids pBAD-ETγ or pBAD-αβγ, depicted, were transformed into the E. coli recA−, recBC+ strain, DK1 and targeted by a chloramphenicol gene as described in FIG. 6 to evaluate ET cloning efficiencies. Arabinose induction of protein expression was for 1 hour.

FIG. 13A

The plasmid pBAD-ETγ is shown by diagram.

FIGS. 13B through 13P

The nucleic acid sequence and the protein coding portions of pBAD-ETγ are depicted.

FIG. 14A

The plasmid pBAD-αβγ is shown by diagram. This plasmid substantially corresponds to the plasmid shown in FIG. 13 except that the recE and recT genes are substituted by the redα and redβ genes.

FIGS. 14B through 14O

The nucleic acid sequence and the protein coding portions of pBAD-αβγ are depicted.

1. Methods 1.1 Preparation of Linear Fragments

Standard PCR reaction condition were used to amplify linear DNA fragments.

The Tn5-neo gene from pJP5603 (Penfold and Pemberton, Gene 118 (1992), 145–146) was amplified by using oligo pairs a/b and c/d. The chloramphenicol (cm) resistant gene from pMAK705 (Hashimoto-Gotoh and Sekiguchi, J. Bacteriol. 131 (1977), 405–412) was amplified by using primer pairs e/f and n/p. The Tn5-neo gene flanked by FRT or loxP sites was amplified from pKaZ or pKaX (http://www.embl-heidelberg.de/Externalnfo/stewart) using oligo pairs i/h, g/h and j/k. The sacB-neo cassette from plB279 (Blomfield et al., Mol. Microbiol. 5 (1991), 1447–1457) was amplified by using oligo pair l/m. The lacZ gene fragment from pSVpaZ11 (Buchholz et al., Nucleic Acids Res. 24 (1996), 4256–4262) was amplified using oligo pair l®/m®. PCR products were purified using the QIAGEN PCR Purification Kit and eluted with $H_2O_2$, followed by digestion of any residual template DNA with Dpn 1. After digestion, PCR products were extracted once with Phenol:CHCl$_3$, ethanol precipitated and resuspended in $H_2O$ at approximately 0.5 μg/μl.

1.2 Preparation of Competent Cells and Electroporation

Saturated overnight cultures were diluted 50 fold into LB medium, grown to an OD600 of 0.5, following by chilling on ice for 15 min. Bacterial cells were centrifuged at 7,000 rpm for 10 min at 0° C. The pellet was resuspended in ice-cold 10% glycerol and centrifuged again (7,000 rpm, −5° C., 10 min). This was repeated twice more and the cell pellet was suspended in an equal volume of ice-cold 10% glycerol. Aliquots of 50 μl were frozen in liquid nitrogen and stored at −80° C. Cells were thawed on ice and 1 μl DNA solution (containing, for co-transformation, 0.3 μg plasmid and 0.2 μg PCR products; or, for transformation, 0.2 μg PCR products) was added. Electroporation was performed using ice-cold cuvettes and a Bio-Rad Gene Pulser set to 25 μFD, 2.3 kV with Pulse Controller set at 200 ohms. LB medium (1 ml) was added after electroporation. The cells were incubated at 37° C. for 1 hour with shaking and then spread on antibiotic plates.

1.3 Induction of RecE and RecT Expression

E. coli JC5547 carrying pBAD24-recET was cultured overnight in LB medium plus 0.2% glucose, 100 μg/ml ampicillin. Five parallel LB cultures, one of which (0) included 0.2% glucose, were started by a 1/100 inoculation. The cultures were incubated at 37° C. with shaking for 4 hours and 0.1% L-arabinose was added 3, 2, 1 or ½ hour before harvesting and processing as above. Immediately before harvesting, 100 μl was removed for analysis on a 10% SDS-polyacrylamide gel. E. coli NS3145 carrying Hoxa-P1 and pBAD-ETγ was induced by 0.1% L-arabinose for 90 min before harvesting.

1.4 Transient Transformation of FLP and Cre Expression Plasmids

The FLP and Cre expression plasmids, 705-Cre and 705-FLP (Buchholz et al., Nucleic Acids Res. 24 (1996), 3118–3119), based on the pSC101 temperature sensitive origin, were transformed into rubidium chloride competent bacterial cells. Cells were spread on 25 μg/ml chloramphenicol plates, and grown for 2 days at 30° C., whereupon colonies were picked, replated on L-agar plates without any antibiotics and incubated at 40° C. overnight. Single colonies were analyzed on various antibiotic plates and all showed the expected loss of chloramphenicol and kanamycin resistance.

1.5 Sucrose Counter Selection of sacB Expression

The E. coli JC9604lacZ strain, generated as described in FIG. 11, was cotransformed with a sacB-neo PCR fragment and pSVpaX1 (Buchholz et al, Nucleic Acids Res. 24 (1996), 4256–4262). After selection on 100 μg/ml ampicillin, 50 μg/ml kanamycin plates, pSVpaX-sacB-neo plasmids were isolated and cotransformed into fresh JC9604lacZ cells with a PCR fragment amplified from pSVpaX1 using primers l$^{i*}$/m$^{i*}$. Oligo m$^{i*}$ carried a silent point mutation which generated a BamHI site. Cells were plated on 7% sucrose, 100 μg/ml ampicillin, 40 μg/ml X-gal plates and incubated at 28° C. for 2 days. The blue and white colonies grown on sucrose plates were counted and further checked by restriction analysis.

1.6 Other Methods

DNA preparation and Southern analysis were performed according to standard procedures. Hybridization probes were generated by random priming of fragments isolated from the Tn5 neo gene (Pvull), Hoxa3 gene (both HindIII fragments), lacZ genes (EcoR1 and BamH1 fragments from pSVpaX1), cm gene (BstB1 fragments from pMAK705) and P1 vector fragments (2.2 kb EcoR1 fragments from P1 vector).

2. Results 2.1 Identification of Recombination Events in E. coli

To identify a flexible homologous recombination reaction in E. coli, an assay based on recombination between linear and circular DNAs was designed (FIG. 1, FIG. 3). Linear DNA carrying the Tn5 kanamycin resistance gene (neo) was made by PCR (FIG. 3a). Initially, the oligonucleotides used for PCR amplification of neo were 60 mers consisting of 42 nucleotides at their 5' ends identical to chosen regions in the plasmid and, at the 3' ends, 18 nucleotides to serve as PCR primers. Linear and circular DNAs were mixed in equimolar proportions and co-transformed into a variety of E. coli hosts. Homologous recombination was only detected in sbcA E. coli hosts. More than 95% of double ampicillin/kanamycin resistant colonies (FIG. 3b) contained the expected homologously recombined plasmid as determined by restriction digestion and sequencing. Only a low background of kanamycin resistance, due to genomic integration of the neo gene, was apparent (not shown).

Figure 3A:
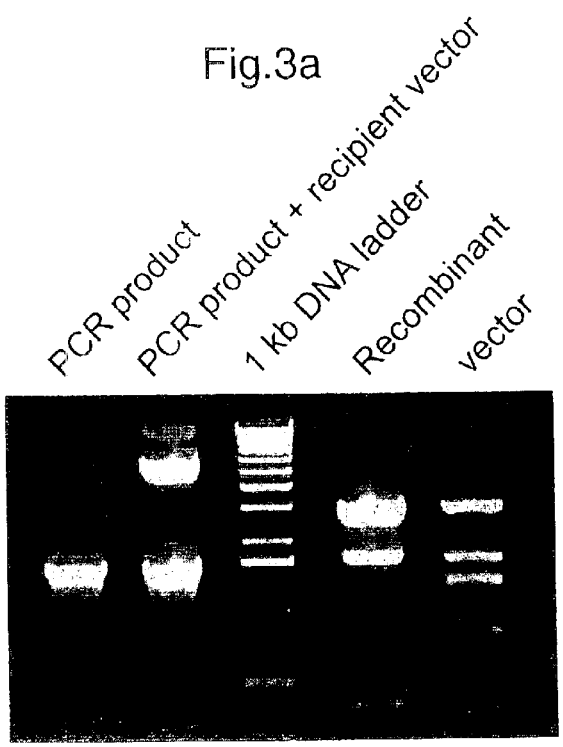
Figure 3B:
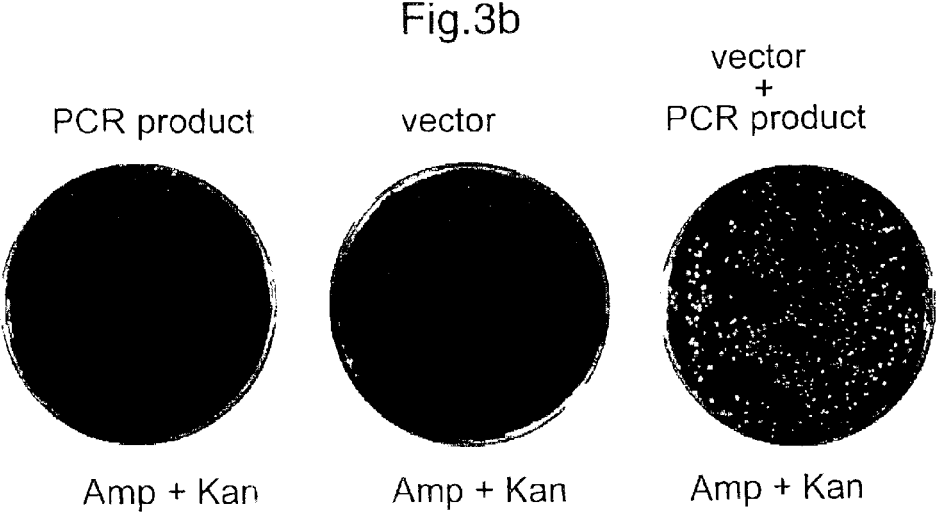
Figure 3C:
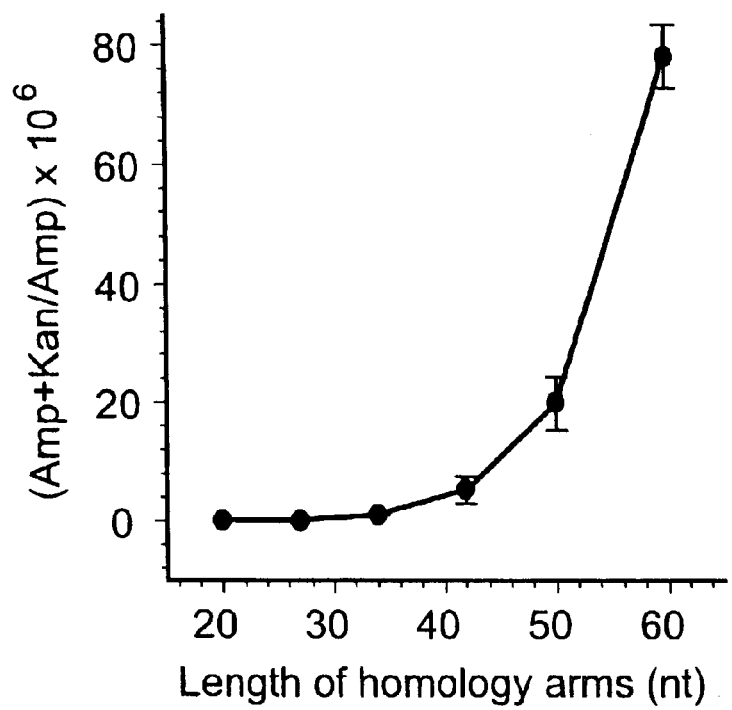
Figure 3D:
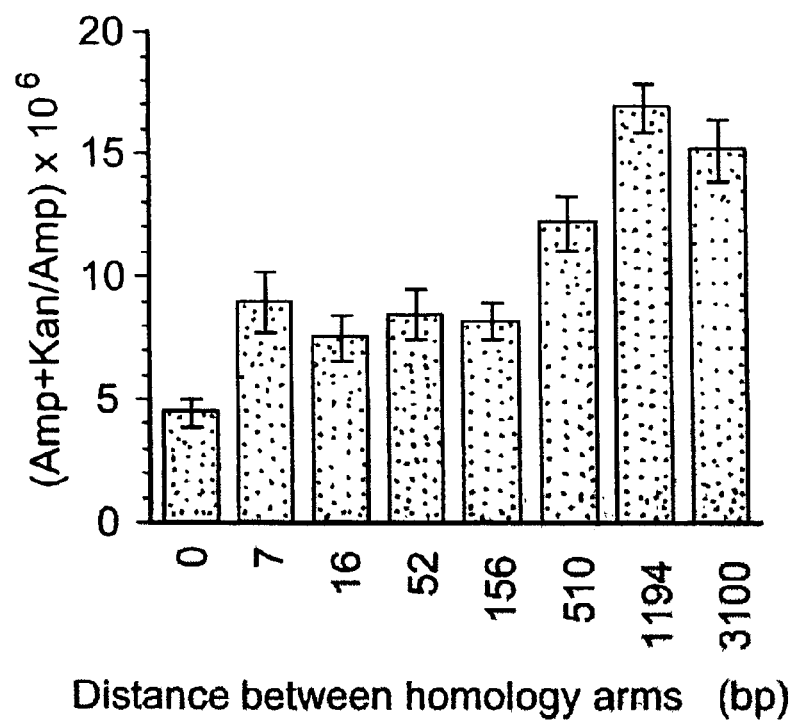

The linear plus circular recombination reaction was characterized in two ways. The relationship between homology arm length and recombination efficiency was simple, with longer arms recombining more efficiently (FIG. 3c). Efficiency increased within the range tested, up to 60 bp. The effect of distance between the two chosen homology sites in the recipient plasmid was examined (FIG. 3d). A set of eight PCR fragments was generated by use of a constant left homology arm with differing right homology arms. The right homology arms were chosen from the plasmid sequence to be 0–3100 bp from the left. Correct products were readily obtained from all, with less than 4 fold difference between them, although the insertional product (0) was least efficient. Correct products also depended on the presence of both homology arms, since PCR fragments containing only one arm failed to work.

2.2 Involvement of RecE and RecT

The relationship between host genotype and this homologous recombination reaction was more systemically examined using a panel of E. coli strains deficient in various recombination components (Table 1).

Only the two sbcA strains, JC8679 and JC9604 presented the intended recombination products and RecA was not required. In sbcA strains, expression of RecE and RecT is activated. Dependence on recE can be inferred from comparison of JC8679 with JC8691. Notably no recombination products were observed in JC9387 suggesting that the sbcBC background is not capable of supporting homologous recombination based on 50 nucleotide homology arms.

Figure 6A:
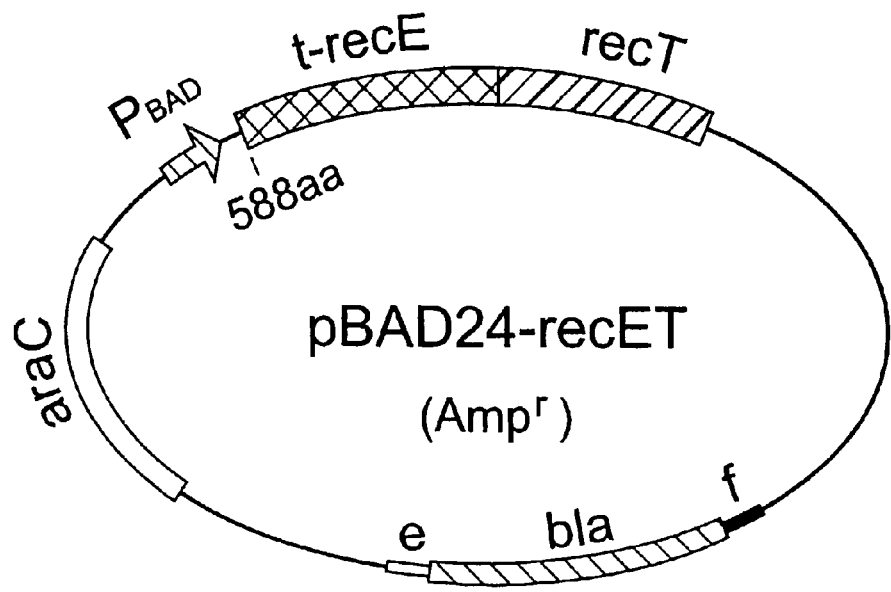
Figure 6A:
Figure 6B:
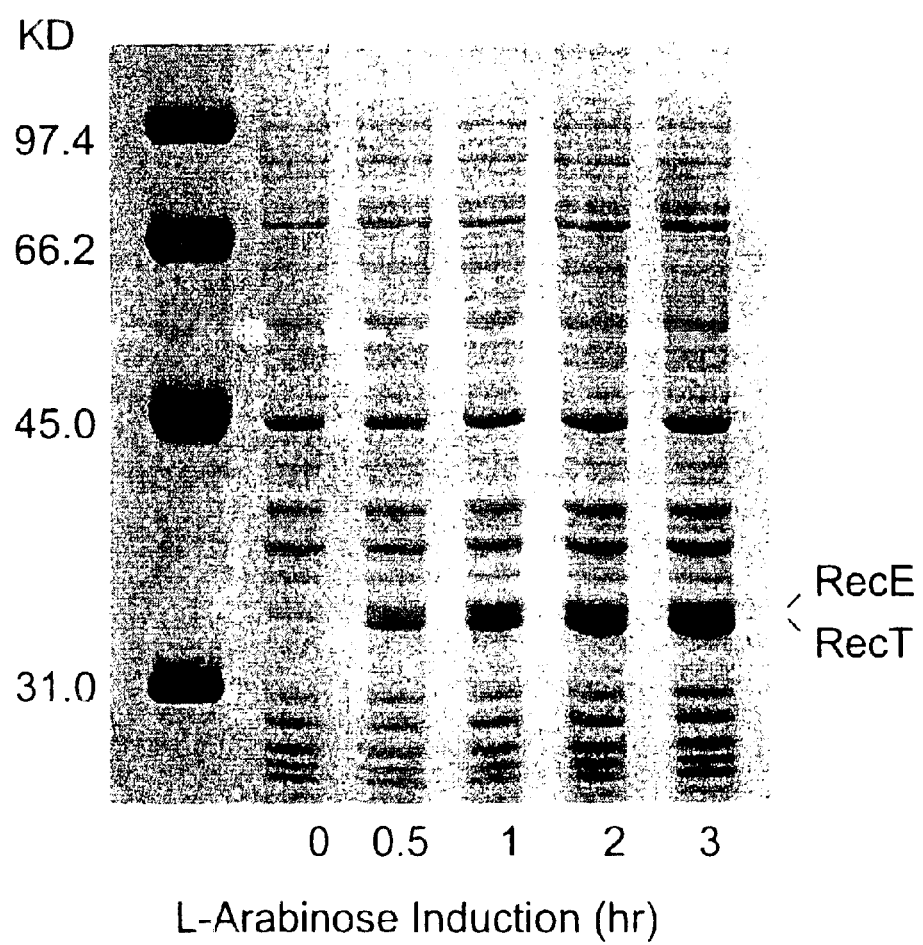
Figure 6C:
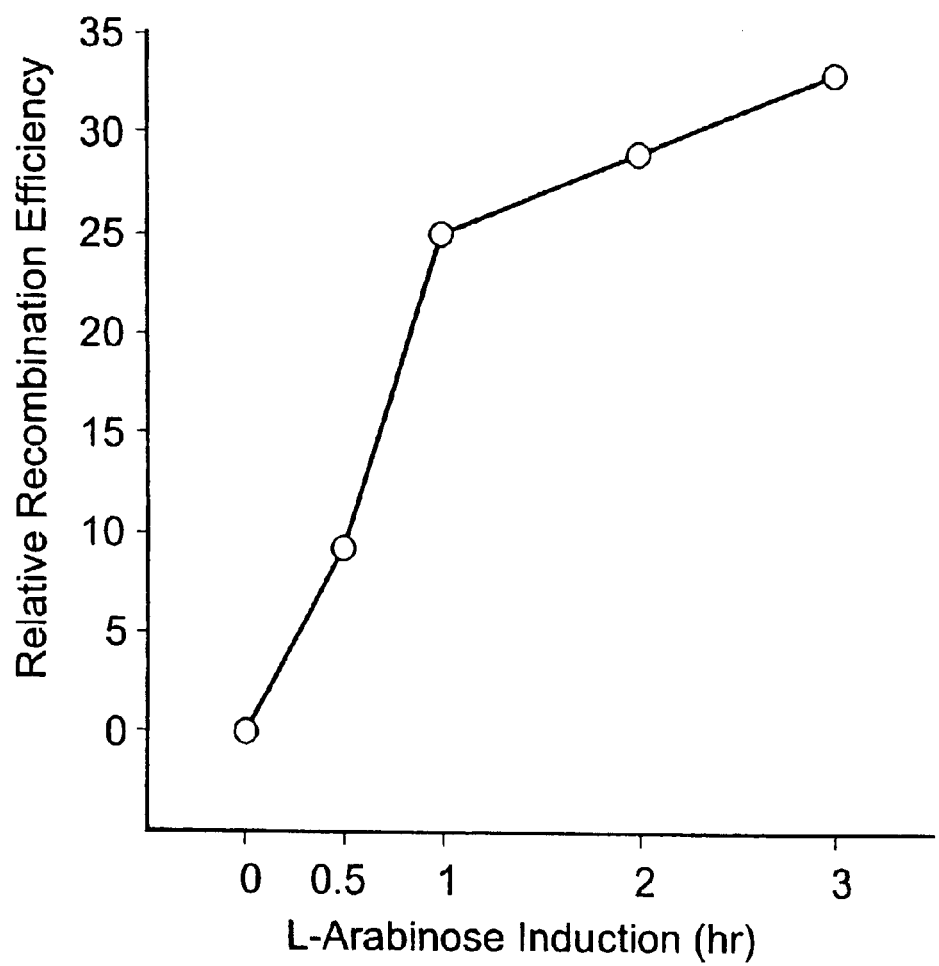

To demonstrate that RecE and RecT are involved, part of the recET operon was cloned into an inducible expression vector to create pBAD24-recET (FIG. 6a). the recE gene was truncated at its N-terminal end, as the first 588 a.a.s of RecE are dispensable. The recBC strain, JC5547, was transformed with pBAD24-recET and a time course of RecE/RecT induction performed by adding arabinose to the culture media at various times before harvesting for competent cells. The batches of harvested competent cells were evaluated for protein expression by gel electrophoresis (FIG. 6b) and for recombination between a linear DNA fragment and the endogenous pBAD24-recET plasmid (FIG. 6c). Without induction of RecE/RecT, no recombinant products were found, whereas recombination increased in approximate concordance with increased RecE/RecT expression. This experiment also shows that co-transformation of linear and circular DNAs is not essential and the circular recipient can be endogenous in the host. From the results shown in FIGS. 3, 6 and Table 2, we conclude that RecE and RecT mediate a very useful homologous recombination reaction in recBC E. coli at workable frequencies. Since RecE and RecT are involved, we refer to this way of recombining linear and circular DNA fragments as "ET cloning".

2.3 Application of ET Cloning to Large Target DNAs

Figure 4B:
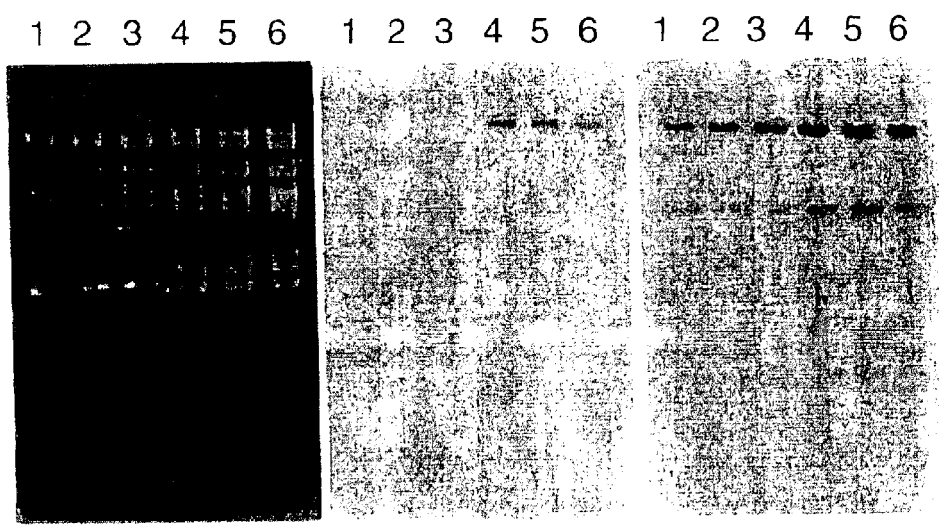

To show that large DNA episomes could be manipulated in E. coli, a>76 kb P1 clone that contains at least 59 kb of the intact mouse Hoxa complex, (confirmed by DNA sequencing and Southern blotting), was transferred to an E. coli strain having an sbcA background (JC9604) and subjected to two rounds of ET cloning. In the first round, the Tn903 kanamycin resistance gene resident in the P1 vector was replaced by an ampicillin resistance gene (FIG. 4). In the second round, the interval between the Hoxa3 and a4 genes was targeted either by inserting the neo gene between two base pairs upstream of the Hoxa3 proximal promoter, or by deleting 6203 bp between the Hoxa3 and a4 genes (FIG. 8a). Both insertional and deletional ET cloning products were readily obtained (FIG. 8b, lanes 2, 3 and 5) showing that the two rounds of ET cloning took place in this large E. coli episome with precision and no apparent unintended recombination.

The general applicability of ET cloning was further examined by targeting a gene in the E. coli chromosome (FIG. 9a). The β-galactosidase (lacZ) gene of JC9604 was chosen so that the ratio between correct and incorrect recombinants could be determined by evaluating β-galactosidase expression. Standard conditions (0.2 µg PCR fragment; 50 µl competent cells), produced 24 primary colonies, 20 of which were correct as determined by β-galactosidase expression (FIG. 9b), and DNA analysis (FIG. 9c, lanes 3–6).

2.4 Secondary Recombination Reactions to Remove Operational Sequences

The products of ET cloning as described above are limited by the necessary inclusion of selectable marker genes. Two different ways to use a further recombination step to remove this limitation were developed. In the first way, site specific recombination mediated by either Flp or Cre recombinase was employed. In the experiments of FIGS. 8 and 9, either Flp recombination target sites (FRTs) or Cre recombination target sites (loxPs) were included to flank the neo gene in the linear substrates. Recombination between the FRTs or loxPs was accomplished by Flp or Cre, respectively, expressed from plasmids with the pSC101 temperature sensitive replication origin (Hashimoto-Gotoh and Sekiguchi, J. Bacteriol. 131 (1977), 405–412) to permit simple elimination of these plasmids after site specific recombination by temperature shift. The precisely recombined Hoxa P1 vector was recovered after both ET and Flp recombination with no other recombination products apparent (FIG. 8, lanes 4 and 6). Similarly, Cre recombinase precisely recombined the targeted lacZ allele (FIG. 9, lanes 7–10). Thus site specific recombination can be readily coupled with ET cloning to remove operational sequences and leave a 34 bp site specific recombination target site at the point of DNA manipulation.

In the second way to remove the selectable marker gene, two rounds of ET cloning, combining positive and counter selection steps, were used to leave the DNA product free of any operational sequences (FIG. 10a).

Figure 5B:
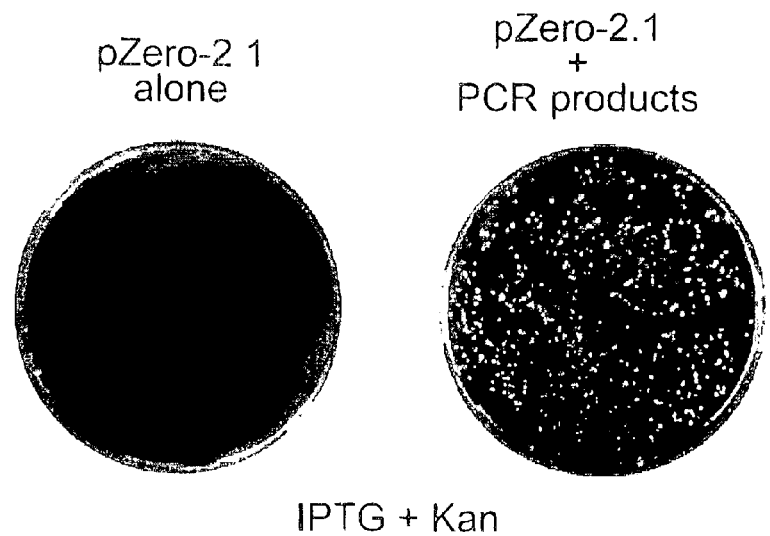

Additionally this experiment was designed to evaluate, by a functional test based on β-galactosidase activity, whether ET cloning promoted small mutations such as frame shift or point mutations within the region being manipulated. In the first round, the lacZ gene of pSVpaX1 was disrupted with a 3.3 kb PCR fragment carrying the neo and B. subtilis sacB (Blomfield et al., Mol. Microbiol. 5 (1991), 1447–1457) genes, by selection for kanamycin resistance (FIG. 10a). As shown above for other positively selected recombination products, virtually all selected colonies were white (FIG. 10b), indicative of successful lacZ disruption, and 17 of 17 were confirmed as correct recombinants by DNA analysis. In the second round, a 1.5 kb PCR fragment designed to repair lacZ was introduced by counter selection against the sacB gene. Repair of lacZ included a silent point mutation to create a BamH1 restriction site. Approximately one quarter of sucrose resistant colonies expressed β-galactosidase, and all analyzed (17 of 17; FIG. 10c) carried the repaired lacZ gene with the BamH1 point mutation. The remaining three quarters of sucrose resistant colonies did not express β-galactosidase, and all analyzed (17 of 17; FIG. 10c) had undergone a variety of large mutational events, none of which resembled the ET cloning product. Thus, in two rounds of ET cloning directed at the lacZ gene, no disturbances of β-galactosidase activity by small mutations were observed, indicating the RecE/RecT recombination works with high fidelity. The significant presence of incorrect products observed in the counter selection step is an inherent limitation of the use of counter selection, since any mutation that ablates expression of the counter selection gene will be selected. Notably, all incorrect products were large mutations and therefore easily distinguished from the correct ET product by DNA analysis. In a different experiment (FIG. 5), we observed that ET cloning into pZero2.1 (InVitroGen) by counter selection against the ccdB gene gave a lower background of incorrect products (8%), indicating that the counter selection background is variable according to parameters that differ from those that influence ET cloning efficiencies.

2.5 Transference of ET Cloning Between *E. coli* Hosts

The experiments shown above were performed in recBC- *E. coli* hosts since the sbcA mutation had been identified as a suppressor of recBC (Barbour et al., Proc. Natl. Acad. Sci. USA 67 (1970), 128–135; Clark, Genetics 78 (1974), 259–271). However, many useful *E. coli* strains are recBC+, including strains commonly used for propagation of P1, BAC or PAC episomes. To transfer ET cloning into recBC+ strains, we developed pBAD-ETγ and pBAD-αβγ (FIGS. 13 and 14). These plasmids incorporate three features important to the mobility of ET cloning. First, RecBC is the major *E. coli* exonuclease and degrades introduced linear fragments. Therefore the RecBC inhibitor, Redγ (Murphy, J. Bacteriol. 173 (1991), 5808–5821), was included. Second, the recombinogenic potential of RecE/RecT, or Redα/Redβ, was regulated by placing recE or redα under an inducible promoter. Consequently ET cloning can be induced when required and undesired recombination events which are restricted at other times. Third, we observed that ET cloning efficiencies are enhanced when RecT, or Redβ, but not RecE, or Redα, is overexpressed. Therefore we placed recT, or redβ, under the strong, constitutive, EM7 promoter.

pBAD-ETγ was transformed into NS3145 *E. coli* harboring the original Hoxa P1 episome (FIG. 11*a*). A region in the P1 vector backbone was targeted by PCR amplification of the chloramphenicol resistance gene (cm) flanked by n and p homology arms. As described above for positively selected ET cloning reactions, most (>90%) chloramphenicol resistant colonies were correct. Notably, the overall efficiency of ET cloning, in terms of linear DNA transformed, was nearly three times better using pBAD-ETγ than with similar experiments based on targeting the same episome in the sbcA host, JC9604. This is consistent with our observation that overexpression of RecT improves ET cloning efficiencies.

Figure 12:
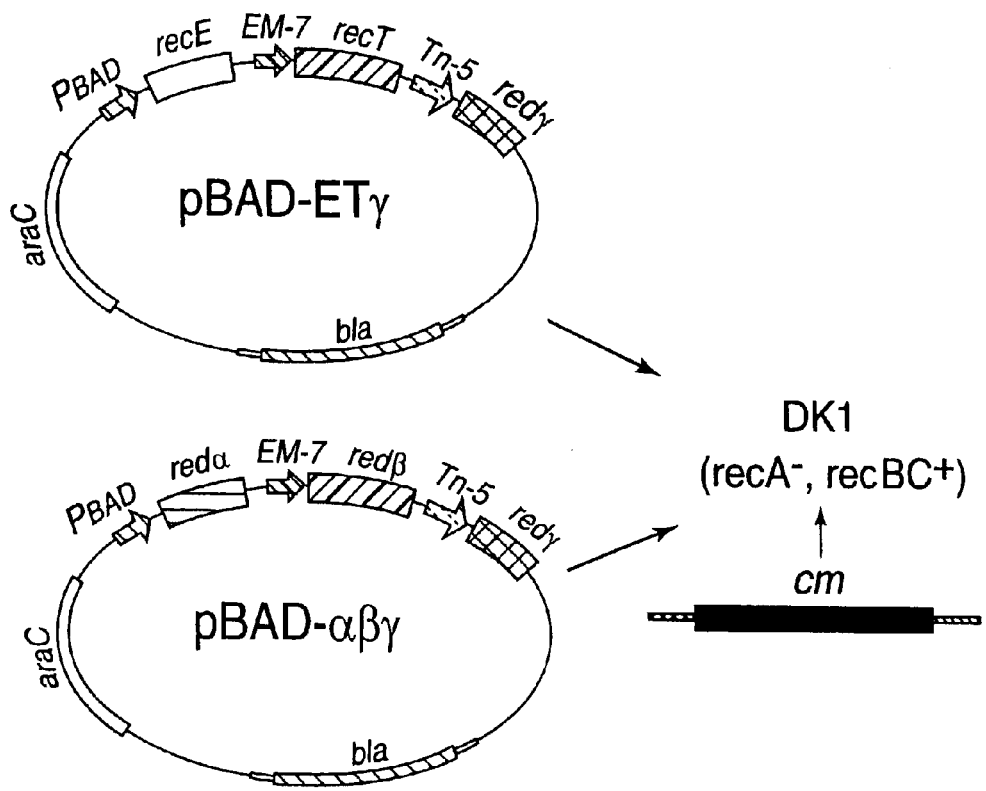
Figure 12:
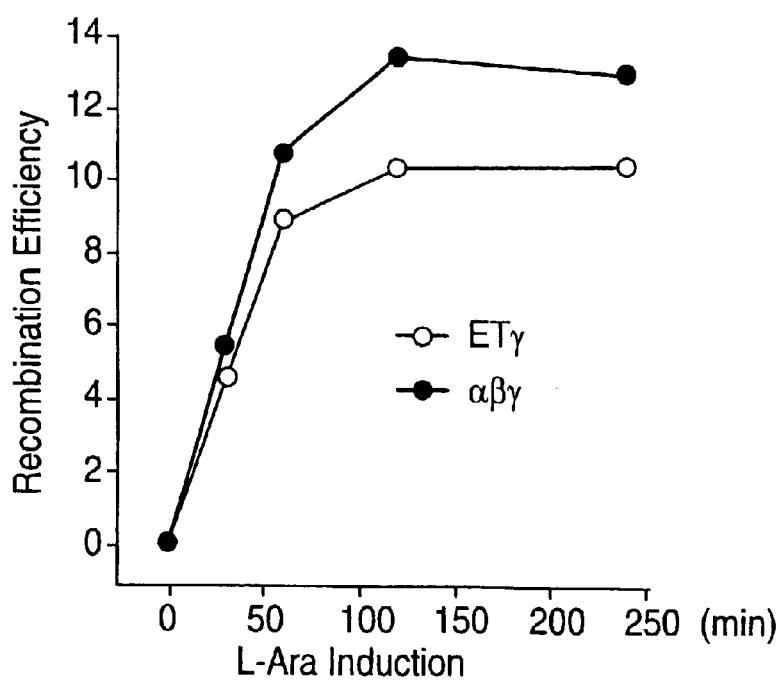

A comparison between ET cloning efficiencies mediated by RecE/RecT, expressed from pBAD-ETγ, and Redα/Redβ, expressed from pBAD-αβγ was made in the recA–, recBC+ *E. coli* strain, DK1 (FIG. 12). After transformation of *E. coli* DK1 with either pBAD-ETγ or pBAD-αβγ, the same experiment as described in FIGS. 6*a,c*, to replace the bla gene of the pBAD vector with a chloramphenicol gene was performed. Both pBAD-ETγ or pBAD-αβγ presented similar ET cloning efficiencies in terms of responsiveness to arabinose induction of RecE and Redα, and number of targeted events.

TABLE 1

| *E. coli* Strains | Genotypes | Amp + Kan | Amp $\times 10^8/\mu g$ |
|---|---|---|---|
| JC8679 | recBC sbcA | 318 | 2.30 |
| JC9604 | recA recBC sbcA | 114 | 0.30 |
| JC8691 | recBC sbcA recE | 0 | 0.37 |
| JC5547 | recA recBC | 0 | 0.37 |
| JC5519 | recBC | 0 | 1.80 |
| JC15329 | recA recBC sbcBC | 0 | 0.03 |
| JC9387 | recBC sbcBC | 0 | 2.20 |
| JC8111 | recBC sbcBC recF | 0 | 2.40 |
| JC9366 | recA | 0 | 0.37 |
| JC13031 | recJ | 0 | 0.45 |

What is claimed is:

1. A method for cloning DNA molecules in prokaryotic cells comprising the steps of:
   a) providing a prokaryotic host cell capable of performing homologous recombination,
   b) contacting in said host cell a circular first DNA molecule which is capable of being replicated in said host cell with a second DNA molecule comprising at least two regions of sequence homology to regions on the first DNA molecule, under conditions for promoting homologous recombination between said first and second DNA molecules, and
   c) selecting a host cell in which homologous recombination between said first and second DNA molecules has occurred,
   wherein a second DNA molecule is introduced into the host cell in a form which allows recombination without further modification, and wherein the homologous recombination occurs by recE and recT mediated gene recombination,
   wherein the recE gene is a nucleic acid molecule selected from the group consisting of:
      (i) the nucleic acid sequence from position 1320 (ATG) to 2159 (GAC) of SEQ ID No. 2,
      (ii) a nucleic acid encoding a recE polypeptide encoded by the nucleic acid sequence of (i) within the degeneracy of the genetic code, and
      (iii) a nucleic acid sequence which hybridizes under stringent conditions with the nucleic acid sequence from (i) and/or (ii).

2. The method according to claim 1, wherein the host cell expresses recE and recT genes.

3. The method according to claim 2, wherein the recE and recT genes are selected from the group of consisting of *E. coli* recE, *E. coli* recT, phage λ redα and phage λ redβ.

4. The method according to claim 1, wherein the host cell is transformed with at least one vector capable of expressing recE and/or recT genes.

5. The method of claim 1, wherein the expression of the recE and/or recT genes is under control of a regulatable promoter.

6. The method of claim 5, wherein the recT gene is over-expressed in comparison to the recE gene.

7. A method for cloning DNA molecules in prokaryotic cells comprising the steps of:
   a) providing a prokaryotic host cell capable of performing homologous recombination,
   b) contacting in said host cell a circular first DNA molecule which is capable of being replicated in said host cell with a second DNA molecule comprising at least two regions of sequence homology to regions on the first DNA molecule, under conditions for promoting homologous recombination between said first and second DNA molecules, and
   c) selecting a host cell in which homologous recombination between said first and second DNA molecules has occurred,
   wherein a second DNA molecule is introduced into the host cell in a form which allows recombination without further modification, and wherein the homologous recombination occurs by recE and recT mediated gene recombination, wherein the recT gene is a nucleic acid molecule selected from the group consisting of:
(i) the nucleic acid sequence from position 2155 (ATG) to 2961 (GM) of SEQ ID No. 4,
(ii) a nucleic acid encoding a recT polypeptide encoded by the nucleic acid sequence of (i) within the degeneracy of the genetic code, and
(iii) a nucleic acid sequence which hybridizes under stringent conditions with the nucleic acid sequences from (i) and/or (ii).

8. A method for cloning DNA molecules in prokaryotic cells comprising the steps of:
a) providing a prokaryotic host cell capable of performing homologous recombination, wherein the host cell expresses a recBC inhibitor gene,
b) contacting in said host cell a circular first DNA molecule which is capable of being replicated in said host cell with a second DNA molecule comprising at least two regions of sequence homology to regions on the first DNA molecule, under conditions for promoting homologous recombination between said first and second DNA molecules, and
c) selecting a host cell in which homologous recombination between said first and second DNA molecules has occurred, wherein a second DNA molecule is introduced into the host cell in a form which allows recombination without further modification, and wherein the homologous recombination occurs by recE and recT mediated gene recombination, wherein the recBC inhibitor gene is a nucleic acid molecule selected from the group consisting of:
(i) the nucleic acid sequence from position 3588 (ATG) to 4002 (GTA) of SEQ ID No. 11,
(ii) a nucleic acid encoding a recBC inhibitor polypeptide encoded by the nucleic acid sequence of (i) within the degeneracy of the genetic code, and
(iii) a nucleic acid sequence which hybridizes under stringent conditions as defined above with the nucleic acid sequence of (i) and/or (ii).

9. The method according to claim 1, wherein the host cell is a gram-negative bacterial cell.

10. The method according to claim 9, wherein the host cell is an *Escherichia coli* cell.

11. The method according to claim 10, wherein the host cell is an *Escherichia coli* K12 strain.

12. The method according to claim 11, wherein the *E. coli* strain is JC 8679 or JC 9604.

13. The method according to claim 8, wherein the host cell is transformed with a vector expressing the recBC inhibitor gene.

14. The method according to claim 13, wherein the host cell is a prokaryotic recBC+ cell.

15. The method according to claim 1, wherein the first DNA molecule is an extrachromosomal DNA molecule containing an origin of replication which is operative in the host cell.

16. The method according to claim 15, wherein the first DNA molecule is selected from the group consisting of plasmids, cosmids, P1 vectors, BAC vectors and PAC vectors.

17. The method according to claim 1, wherein the first DNA molecule is a host cell chromosome.

18. The method according to claim 1, the second DNA molecule is linear.

19. The method according to claim 1, wherein the regions of sequence homology are at least 15 nucleotides each.

20. The method according to claim 1, wherein the second DNA molecule is obtained by an amplification reaction.

21. The method according to claim 1, wherein the first and/or second DNA molecules are introduced into the host cells by transformation.

22. The method according to claim 1, wherein the transformation method is electroporation.

23. The method according to claim 1, wherein the first and second DNA molecules are introduced into the host cell simultaneously by co-transformation.

24. The according to claim 1, wherein the second DNA molecule is introduced into a host cell in which the first DNA molecule is already present.

25. The method according to claim 1, wherein the second DNA molecule contains at least one marker gene placed between the two regions of sequence homology and wherein homologous recombination is detected by expression of said marker gene.

26. The method according to claim 25, wherein the marker gene is selected from the group consisting of antibiotic resistance genes, deficiency complementation genes and reporter genes.

27. The method of claim 1, wherein the first DNA molecule contains at least one marker gene between the two regions of sequence homology and wherein homologous recombination is detected by lack of expression of said marker gene.

28. The method of claim 27, wherein said marker gene is a reporter gene or a gene which conveys a toxic or bacteriostatic effect on the cell.

29. The method according to claim 1, wherein the first DNA molecule contains at least one target site for a site specific recombinase between the two regions of sequence homology and wherein homologous recombination is detected by removal of said target site.

* * * * *

SEQUENCE LISTING

<160> NUMBER OF SEQ ID NOS: 14

<210> SEQ ID NO 1
<211> LENGTH: 6150
<212> TYPE: DNA
<213> ORGANISM: Artificial Sequence
<220> FEATURE:
<221> NAME/KEY: misc_feature
<222> LOCATION: (1)..(6150)
<223> OTHER INFORMATION: plasmid pBAD24-rec ET
<220> FEATURE:
<221> NAME/KEY: misc_feature
<222> LOCATION: (96)..(974)
<223> OTHER INFORMATION: product = "araC"
<220> FEATURE:
<221> NAME/KEY: misc_feature
<222> LOCATION: (1320)..(2162)
<223> OTHER INFORMATION: product = "t-recE"
<220> FEATURE:
<221> NAME/KEY: misc_feature
<222> LOCATION: (2155)..(2972)
<223> OTHER INFORMATION: product = "recT"
<220> FEATURE:
<221> NAME/KEY: misc_feature
<222> LOCATION: (3493)..(4353)
<223> OTHER INFORMATION: product = "bla"

<400> SEQUENCE: 1

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcacttttt cttcacaacc ggcacggaac tcgctcgggc tggccccggt gcatttttta     180
aatacccgcg agaaatagag ttgatcgtca aaaccaacat tgcgaccgac ggtggcgata     240
```

| | |
|---|---|
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaaatcga gataaccgtt ggcctcaatc | 900 |
| ggcgttaaac ccgccaccag atgggcatta acgagtatc ccggcagcag gggatcattt | 960 |
| tgcgcttcag ccatactttt catactcccg ccattcagag aagaaaccaa ttgtccatat | 1020 |
| tgcatcagac attgccgtca ctgcgtcttt tactggctct ctcgctaac caaaccggta | 1080 |
| accccgctta ttaaaagcat tctgtaacaa agcgggacca agccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgctttta | 1260 |
| tcgcaactct ctactgtttc tccatacccg tttttttggg ctagcaggag gaattcacca | 1320 |
| tggatcccgt aatcgtagaa gacatagagc caggtattta ttacggaatt tcgaatgaga | 1380 |
| attaccacgc gggtcccggt atcagtaagt ctcagctcga tgacattgct gatactccgg | 1440 |
| cactatatt gtggcgtaaa aatgcccccg tggacaccac aaagacaaaa acgctcgatt | 1500 |
| taggaactgc tttccactgc cgggtacttg aaccggaaga attcagtaac cgctttatcg | 1560 |
| tagcacctga atttaaccgc cgtacaaacg ccggaaaaga agaagagaaa gcgtttctga | 1620 |
| tggaatgcgc aagcacagga aaaacggtta tcactgcgga agaaggccgg aaaattgaac | 1680 |
| tcatgtatca aagcgttatg gctttgccgc tggggcaatg gcttgttgaa agcgccggac | 1740 |
| acgctgaatc atcaatttac tgggaagatc ctgaaacagg aattttgtgt cggtgccgtc | 1800 |
| cggacaaaat tatccctgaa tttcactgga tcatggacgt gaaaactacg gcggatattc | 1860 |
| aacgattcaa aaccgcttat tacgactacc gctatcacgt tcaggatgca ttctacagtg | 1920 |
| acggttatga agcacagttt ggagtgcagc caactttcgt ttttctggtt gccagcacaa | 1980 |
| ctattgaatg cggacgttat ccggttgaaa ttttcatgat gggcgaagaa gcaaaactgg | 2040 |
| caggtcaaca ggaatatcac cgcaatctgc gaaccctgtc tgactgcctg aataccgatg | 2100 |
| aatggccagc tattaagaca ttatcactgc cccgctgggc taaggaatat gcaaatgact | 2160 |
| aagcaaccac caatcgcaaa agccgatctg caaaaaactc agggaaaccg tgcaccagca | 2220 |
| gcagttaaaa atagcgacgt gattagtttt attaaccagc catcaatgaa agagcaactg | 2280 |
| gcagcagctc ttccacgcca tatgacggct gaacgtatga tccgtatcgc caccacagaa | 2340 |
| attcgtaaag ttccggcgtt aggaaactgt gacactatga gttttgtcag tgcgatcgta | 2400 |
| cagtgttcac agctcggact tgagccaggt agcgccctcg gtcatgcata tttactgcct | 2460 |
| tttggtaata aaaacgaaaa gagcggtaaa aagaacgttc agctaatcat tggctatcgc | 2520 |
| ggcatgattg atcggctcg ccgttctggt caaatcgcca gcctgtcagc ccgtgttgtc | 2580 |
| cgtgaaggtg acgagtttag cttcgaattt ggccttgatg aaaagttaat acaccgcccg | 2640 |

```
ggagaaaacg aagatgcccc ggttacccac gtctatgctg tcgcaagact gaaagacgga    2700
ggtactcagt ttgaagttat gacgcgcaaa cagattgagc tggtgcgcag cctgagtaaa    2760
gctggtaata acgggccgtg ggtaactcac tgggaagaaa tggcaaagaa acggctatt    2820 cgtcgcctgt tcaaatattt gcccgtatca attgagatcc agcgtgcagt atcaatggat    2880
gaaaaggaac cactgacaat cgatcctgca gattcctctg tattaaccgg ggaatacagt    2940
gtaatcgata attcagagga atagatctaa gcttggctgt tttggcggat gagagaagat    3000
tttcagcctg atacagatta aatcagaacg cagaagcggt ctgataaaac agaatttgcc    3060
tggcggcagt agcgcggtgg tcccacctga ccccatgccg aactcagaag tgaaacgccg    3120
tagcgccgat ggtagtgtgg ggtctcccca tgcgagagta gggaactgcc aggcatcaaa    3180
taaaacgaaa ggctcagtcg aaagactggg cctttcgttt tatctgttgt ttgtcggtga    3240
acgctctcct gagtaggaca atccgccgg gagcggattt gaacgttgcg aagcaacggc    3300
ccggagggtg gcgggcagga cgcccgccat aaactgccag gcatcaaatt aagcagaagg    3360
ccatcctgac ggatggcctt tttgcgtttc tacaaactct tttgtttatt tttctaaata    3420
cattcaaata tgtatccgct catgagacaa taaccctgat aaatgcttca ataatattga    3480 aaaggaaga gtatgagtat tcaacatttc cgtgtcgccc ttattccctt ttttgcggca    3540
ttttgccttc ctgttttgc tcacccagaa acgctggtga agtaaaaga tgctgaagat    3600 cagttgggtg cacgagtggg ttacatcgaa ctggatctca acagcggtaa gatccttgag    3660
agttttcgcc ccgaagaacg ttttccaatg atgagcactt taaagttct gctatgtggc    3720 gcggtattat cccgtgttga cgccgggcaa gagcaactcg gtcgccgcat acactattct    3780
cagaatgact tggttgagta ctcaccagtc acagaaaagc atcttacgga tggcatgaca    3840
gtaagagaat tatgcagtgc tgccataacc atgagtgata acactgcggc caacttactt    3900
ctgacaacga tcggaggacc gaaggagcta accgcttttt tgcacaacat ggggatcat    3960 gtaactcgcc ttgatcgttg ggaaccggag ctgaatgaag ccataccaaa cgacgagcgt    4020
gacaccacga tgcctgtagc aatggcaaca acgttgcgca aactattaac tggcgaacta    4080
cttactctag cttcccggca acaattaata gactggatgg aggcggataa agttgcagga    4140
ccacttctgc gctcggccct tccggctggc tggtttattg ctgataaatc tggagccggt    4200
gagcgtgggt ctcgcggtat cattgcagca ctggggccag atggtaagcc ctcccgtatc    4260
gtagttatct acacgacggg gagtcaggca actatggatg aacgaaatag acagatcgct    4320
gagataggtg cctcactgat taagcattgg taactgtcag accaagttta ctcatatata    4380
ctttagattg atttacgcgc cctgtagcgg cgcattaagc gcggcgggtg tggtggttac    4440
gcgcagcgtg accgctacac ttgccagcgc cctagcgccc gctcctttcg ctttcttccc    4500
ttcctttctc gccacgttcg ccggcttcc ccgtcaagct ctaaatcggg gctcccttt    4560 agggttccga tttagtgctt tacggcacct cgaccccaaa aaacttgatt tgggtgatgg    4620
ttcacgtagt gggccatcgc cctgatagac ggtttttcgc cctttgacgt tggagtccac    4680
gttctttaat agtggactct tgttccaaac ttgaacaaca ctcaaccta tctcgggcta    4740 ttcttttgat ttataaggga ttttgccgat ttcggcctat tggttaaaaa atgagctgat    4800
ttaacaaaaa tttaacgcga attttaacaa atattaacg tttacaattt aaaaggatct    4860
aggtgaagat cctttttgat aatctcatga ccaaaatccc ttaacgtgag ttttcgttcc    4920
actgagcgtc agaccccgta gaaaagatca aaggatcttc ttgagatcct ttttttctgc    4980
```

-continued

```
gcgtaatctg ctgcttgcaa acaaaaaaac caccgctacc agcggtggtt tgtttgccgg      5040
atcaagagct accaactctt tttccgaagg taactggctt cagcagagcg cagataccaa      5100
atactgtcct tctagtgtag ccgtagttag gccaccactt caagaactct gtagcaccgc      5160
ctacatacct cgctctgcta atcctgttac cagtggctgc tgccagtggc gataagtcgt      5220
gtcttaccgg gttggactca agacgatagt taccggataa ggcgcagcgg tcgggctgaa      5280
cggggggttc gtgcacacag cccagcttgg agcgaacgac ctacaccgaa ctgagatacc      5340
tacagcgtga gctatgagaa agcgccacgc ttcccgaagg gagaaaggcg gacaggtatc      5400
cggtaagcgg cagggtcgga acaggagagc gcacagggga gcttccaggg ggaaacgcct      5460
ggtatcttta tagtcctgtc gggtttcgcc acctctgact tgagcgtcga ttttgtgat      5520 gctcgtcagg gggcggagc ctatggaaaa acgccagcaa cgcggccttt ttacggttcc       5580 tggcctttg ctggcctttt gctcacatgt tctttcctgc gttatcccct gattctgtgg       5640
ataaccgtat taccgccttt gagtgagctg ataccgctcg ccgcagccga acgaccgagc      5700
gcagcgagtc agtgagcgag gaagcggaag agcgcctgat gcggtatttt ctccttacgc      5760
atctgtgcgg tatttcacac cgcatagggt catggctgcg ccccgacacc cgccaacacc      5820
cgctgacgcg ccctgacggg cttgtctgct cccggcatcc gcttacagac aagctgtgac      5880
cgtctccggg agctgcatgt gtcagaggtt ttcaccgtca tcaccgaaac gcgcgaggca      5940
gcaaggagat ggcgcccaac agtccccgg ccacggggcc tgccaccata cccacgccga       6000
aacaagcgct catgagcccg aagtggcgag cccgatcttc cccatcggtg atgtcggcga     6060
tataggcgcc agcaaccgca cctgtggcgc cggtgatgcc ggccacgatg cgtccggcgt     6120
agaggatctg ctcatgtttg acagcttatc                                      6150
```

<210> SEQ ID NO 2
<211> LENGTH: 843
<212> TYPE: DNA
<213> ORGANISM: Artificial Sequence
<220> FEATURE:
<221> NAME/KEY: misc_feature
<222> LOCATION: (1)..(843)
<223> OTHER INFORMATION: t-recE on plasmid pBAD24-recET at 1320-2162
<220> FEATURE:
<221> NAME/KEY: CDS
<222> LOCATION: (1)..(843)
<223> OTHER INFORMATION: t-recE

<400> SEQUENCE: 2

```
atg gat ccc gta atc gta gaa gac ata gag cca ggt att tat tac gga      48
Met Asp Pro Val Ile Val Glu Asp Ile Glu Pro Gly Ile Tyr Tyr Gly
  1               5                  10                  15 att tcg aat gag aat tac cac gcg ggt ccc ggt atc agt aag tct cag      96
Ile Ser Asn Glu Asn Tyr His Ala Gly Pro Gly Ile Ser Lys Ser Gln
             20                  25                  30 ctc gat gac att gct gat act ccg gca cta tat ttg tgg cgt aaa aat     144
Leu Asp Asp Ile Ala Asp Thr Pro Ala Leu Tyr Leu Trp Arg Lys Asn
         35                  40                  45 gcc ccc gtg gac acc aca aag aca aaa acg ctc gat tta gga act gct     192
Ala Pro Val Asp Thr Thr Lys Thr Lys Thr Leu Asp Leu Gly Thr Ala
     50                  55                  60 ttc cac tgc cgg gta ctt gaa ccg gaa gaa ttc agt aac cgc ttt atc     240
Phe His Cys Arg Val Leu Glu Pro Glu Glu Phe Ser Asn Arg Phe Ile
 65                  70                  75                  80 gta gca cct gaa ttt aac cgc cgt aca aac gcc gga aaa gaa gaa gag     288
Val Ala Pro Glu Phe Asn Arg Arg Thr Asn Ala Gly Lys Glu Glu Glu
                 85                  90                  95
```

```
aaa gcg ttt ctg atg gaa tgc gca agc aca gga aaa acg gtt atc act    336
Lys Ala Phe Leu Met Glu Cys Ala Ser Thr Gly Lys Thr Val Ile Thr
            100                 105                 110 gcg gaa gaa ggc cgg aaa att gaa ctc atg tat caa agc gtt atg gct    384
Ala Glu Glu Gly Arg Lys Ile Glu Leu Met Tyr Gln Ser Val Met Ala
            115                 120                 125 ttg ccg ctg ggg caa tgg ctt gtt gaa agc gcc gga cac gct gaa tca    432
Leu Pro Leu Gly Gln Trp Leu Val Glu Ser Ala Gly His Ala Glu Ser
        130                 135                 140 tca att tac tgg gaa gat cct gaa aca gga att ttg tgt cgg tgc cgt    480
Ser Ile Tyr Trp Glu Asp Pro Glu Thr Gly Ile Leu Cys Arg Cys Arg
145                 150                 155                 160 ccg gac aaa att atc cct gaa ttt cac tgg atc atg gac gtg aaa act    528
Pro Asp Lys Ile Ile Pro Glu Phe His Trp Ile Met Asp Val Lys Thr
                165                 170                 175 acg gcg gat att caa cga ttc aaa acc gct tat tac gac tac cgc tat    576
Thr Ala Asp Ile Gln Arg Phe Lys Thr Ala Tyr Tyr Asp Tyr Arg Tyr
            180                 185                 190 cac gtt cag gat gca ttc tac agt gac ggt tat gaa gca cag ttt gga    624
His Val Gln Asp Ala Phe Tyr Ser Asp Gly Tyr Glu Ala Gln Phe Gly
            195                 200                 205 gtg cag cca act ttc gtt ttt ctg gtt gcc agc aca act att gaa tgc    672
Val Gln Pro Thr Phe Val Phe Leu Val Ala Ser Thr Thr Ile Glu Cys
210                 215                 220 gga cgt tat ccg gtt gaa att ttc atg atg ggc gaa gaa gca aaa ctg    720
Gly Arg Tyr Pro Val Glu Ile Phe Met Met Gly Glu Glu Ala Lys Leu
225                 230                 235                 240 gca ggt caa cag gaa tat cac cgc aat ctg cga acc ctg tct gac tgc    768
Ala Gly Gln Gln Glu Tyr His Arg Asn Leu Arg Thr Leu Ser Asp Cys
                245                 250                 255 ctg aat acc gat gaa tgg cca gct att aag aca tta tca ctg ccc cgc    816
Leu Asn Thr Asp Glu Trp Pro Ala Ile Lys Thr Leu Ser Leu Pro Arg
            260                 265                 270 tgg gct aag gaa tat gca aat gac taa                                843
Trp Ala Lys Glu Tyr Ala Asn Asp  *
            275                 280

<210> SEQ ID NO 3
<211> LENGTH: 280
<212> TYPE: PRT
<213> ORGANISM: Artificial Sequence
<220> FEATURE:
<221> NAME/KEY: misc_feature
<222> LOCATION: (1)..(280)
<223> OTHER INFORMATION: t-recE on plasmid pBAD24-recET at 1320-2162

<400> SEQUENCE: 3

Met Asp Pro Val Ile Val Glu Asp Ile Glu Pro Gly Ile Tyr Tyr Gly
 1               5                  10                  15

Ile Ser Asn Glu Asn Tyr His Ala Gly Pro Gly Ile Ser Lys Ser Gln
            20                  25                  30

Leu Asp Asp Ile Ala Asp Thr Pro Ala Leu Tyr Leu Trp Arg Lys Asn
        35                  40                  45

Ala Pro Val Asp Thr Thr Lys Thr Lys Thr Leu Asp Leu Gly Thr Ala
    50                  55                  60

Phe His Cys Arg Val Leu Glu Pro Glu Glu Phe Ser Asn Arg Phe Ile
65                  70                  75                  80

Val Ala Pro Glu Phe Asn Arg Arg Thr Asn Ala Gly Lys Glu Glu Glu
                85                  90                  95
```

-continued

```
Lys Ala Phe Leu Met Glu Cys Ala Ser Thr Gly Lys Thr Val Ile Thr
                100                 105                 110

Ala Glu Glu Gly Arg Lys Ile Glu Leu Met Tyr Gln Ser Val Met Ala
            115                 120                 125

Leu Pro Leu Gly Gln Trp Leu Val Glu Ser Ala Gly His Ala Glu Ser
        130                 135                 140

Ser Ile Tyr Trp Glu Asp Pro Glu Thr Gly Ile Leu Cys Arg Cys Arg
145                 150                 155                 160

Pro Asp Lys Ile Ile Pro Glu Phe His Trp Ile Met Asp Val Lys Thr
                165                 170                 175

Thr Ala Asp Ile Gln Arg Phe Lys Thr Ala Tyr Tyr Asp Tyr Arg Tyr
            180                 185                 190

His Val Gln Asp Ala Phe Tyr Ser Asp Gly Tyr Glu Ala Gln Phe Gly
        195                 200                 205

Val Gln Pro Thr Phe Val Phe Leu Val Ala Ser Thr Thr Ile Glu Cys
    210                 215                 220

Gly Arg Tyr Pro Val Glu Ile Phe Met Met Gly Glu Ala Lys Leu
225                 230                 235                 240

Ala Gly Gln Gln Glu Tyr His Arg Asn Leu Arg Thr Leu Ser Asp Cys
                245                 250                 255

Leu Asn Thr Asp Glu Trp Pro Ala Ile Lys Thr Leu Ser Leu Pro Arg
            260                 265                 270

Trp Ala Lys Glu Tyr Ala Asn Asp
        275                 280

<210> SEQ ID NO 4
<211> LENGTH: 810
<212> TYPE: DNA
<213> ORGANISM: Artificial Sequence
<220> FEATURE:
<221> NAME/KEY: misc_feature
<222> LOCATION: (1)..(810)
<223> OTHER INFORMATION: recT on plasmid pBAD24-recET at 2155-2972
<220> FEATURE:
<221> NAME/KEY: CDS
<222> LOCATION: (1)..(810)
<223> OTHER INFORMATION: recT

<400> SEQUENCE: 4 atg act aag caa cca cca atc gca aaa gcc gat ctg caa aaa act cag      48
Met Thr Lys Gln Pro Pro Ile Ala Lys Ala Asp Leu Gln Lys Thr Gln
                285                 290                 295 gga aac cgt gca cca gca gca gtt aaa aat agc gac gtg att agt ttt      96
Gly Asn Arg Ala Pro Ala Ala Val Lys Asn Ser Asp Val Ile Ser Phe
            300                 305                 310 att aac cag cca tca atg aaa gag caa ctg gca gca gct ctt cca cgc     144
Ile Asn Gln Pro Ser Met Lys Glu Gln Leu Ala Ala Ala Leu Pro Arg
        315                 320                 325 cat atg acg gct gaa cgt atg atc cgt atc gcc acc aca gaa att cgt     192
His Met Thr Ala Glu Arg Met Ile Arg Ile Ala Thr Thr Glu Ile Arg
330                 335                 340                 345 aaa gtt ccg gcg tta gga aac tgt gac act atg agt ttt gtc agt gcg     240
Lys Val Pro Ala Leu Gly Asn Cys Asp Thr Met Ser Phe Val Ser Ala
                350                 355                 360 atc gta cag tgt tca cag ctc gga ctt gag cca ggt agc gcc ctc ggt     288
Ile Val Gln Cys Ser Gln Leu Gly Leu Glu Pro Gly Ser Ala Leu Gly
            365                 370                 375 cat gca tat tta ctg cct ttt ggt aat aaa aac gaa aag agc ggt aaa     336
His Ala Tyr Leu Leu Pro Phe Gly Asn Lys Asn Glu Lys Ser Gly Lys
        380                 385                 390
```

```
aag aac gtt cag cta atc att ggc tat cgc ggc atg att gat ctg gct    384
Lys Asn Val Gln Leu Ile Ile Gly Tyr Arg Gly Met Ile Asp Leu Ala
            395                 400                 405 cgc cgt tct ggt caa atc gcc agc ctg tca gcc cgt gtt gtc cgt gaa    432
Arg Arg Ser Gly Gln Ile Ala Ser Leu Ser Ala Arg Val Val Arg Glu
410                 415                 420                 425 ggt gac gag ttt agc ttc gaa ttt ggc ctt gat gaa aag tta ata cac    480
Gly Asp Glu Phe Ser Phe Glu Phe Gly Leu Asp Glu Lys Leu Ile His
                430                 435                 440 cgc ccg gga gaa aac gaa gat gcc ccg gtt acc cac gtc tat gct gtc    528
Arg Pro Gly Glu Asn Glu Asp Ala Pro Val Thr His Val Tyr Ala Val
            445                 450                 455 gca aga ctg aaa gac gga ggt act cag ttt gaa gtt atg acg cgc aaa    576
Ala Arg Leu Lys Asp Gly Gly Thr Gln Phe Glu Val Met Thr Arg Lys
460                 465                 470 cag att gag ctg gtg cgc agc ctg agt aaa gct ggt aat aac ggg ccg    624
Gln Ile Glu Leu Val Arg Ser Leu Ser Lys Ala Gly Asn Asn Gly Pro
                475                 480                 485 tgg gta act cac tgg gaa gaa atg gca aag aaa acg gct att cgt cgc    672
Trp Val Thr His Trp Glu Glu Met Ala Lys Lys Thr Ala Ile Arg Arg
490                 495                 500                 505 ctg ttc aaa tat ttg ccc gta tca att gag atc cag cgt gca gta tca    720
Leu Phe Lys Tyr Leu Pro Val Ser Ile Glu Ile Gln Arg Ala Val Ser
                510                 515                 520 atg gat gaa aag gaa cca ctg aca atc gat cct gca gat tcc tct gta    768
Met Asp Glu Lys Glu Pro Leu Thr Ile Asp Pro Ala Asp Ser Ser Val
            525                 530                 535 tta acc ggg gaa tac agt gta atc gat aat tca gag gaa tag            810
Leu Thr Gly Glu Tyr Ser Val Ile Asp Asn Ser Glu Glu *
            540                 545                 550

<210> SEQ ID NO 5
<211> LENGTH: 269
<212> TYPE: PRT
<213> ORGANISM: Artificial Sequence
<220> FEATURE:
<221> NAME/KEY: misc_feature
<222> LOCATION: (1)..(269)
<223> OTHER INFORMATION: recT on plasmid pBAD24-recET at 2155-2972

<400> SEQUENCE: 5

Met Thr Lys Gln Pro Pro Ile Ala Lys Ala Asp Leu Gln Lys Thr Gln
1               5                   10                  15

Gly Asn Arg Ala Pro Ala Ala Val Lys Asn Ser Asp Val Ile Ser Phe
            20                  25                  30

Ile Asn Gln Pro Ser Met Lys Glu Gln Leu Ala Ala Ala Leu Pro Arg
        35                  40                  45

His Met Thr Ala Glu Arg Met Ile Arg Ile Ala Thr Thr Glu Ile Arg
    50                  55                  60

Lys Val Pro Ala Leu Gly Asn Cys Asp Thr Met Ser Phe Val Ser Ala
65                  70                  75                  80

Ile Val Gln Cys Ser Gln Leu Gly Leu Glu Pro Gly Ser Ala Leu Gly
                85                  90                  95

His Ala Tyr Leu Leu Pro Phe Gly Asn Lys Asn Glu Lys Ser Gly Lys
            100                 105                 110

Lys Asn Val Gln Leu Ile Ile Gly Tyr Arg Gly Met Ile Asp Leu Ala
        115                 120                 125

Arg Arg Ser Gly Gln Ile Ala Ser Leu Ser Ala Arg Val Val Arg Glu
    130                 135                 140
```

Gly Asp Glu Phe Ser Phe Glu Phe Gly Leu Asp Glu Lys Leu Ile His
145                 150                 155                 160

Arg Pro Gly Glu Asn Glu Asp Ala Pro Val Thr His Val Tyr Ala Val
                165                 170                 175

Ala Arg Leu Lys Asp Gly Gly Thr Gln Phe Glu Val Met Thr Arg Lys
            180                 185                 190

Gln Ile Glu Leu Val Arg Ser Leu Ser Lys Ala Gly Asn Asn Gly Pro
        195                 200                 205

Trp Val Thr His Trp Glu Glu Met Ala Lys Lys Thr Ala Ile Arg Arg
    210                 215                 220

Leu Phe Lys Tyr Leu Pro Val Ser Ile Glu Ile Gln Arg Ala Val Ser
225                 230                 235                 240

Met Asp Glu Lys Glu Pro Leu Thr Ile Asp Pro Ala Asp Ser Ser Val
                245                 250                 255

Leu Thr Gly Glu Tyr Ser Val Ile Asp Asn Ser Glu Glu
            260                 265

<210> SEQ ID NO 6
<211> LENGTH: 876
<212> TYPE: DNA
<213> ORGANISM: Artificial Sequence
<220> FEATURE:
<221> NAME/KEY: misc_feature
<222> LOCATION: (1)..(876)
<223> OTHER INFORMATION: araC on plasmid pBAD24-recET at 974-996
<220> FEATURE:
<221> NAME/KEY: CDS
<222> LOCATION: (1)..(876)
<223> OTHER INFORMATION: araC

<400> SEQUENCE: 6
tgacaacttg acggctacat cattcacttt ttcttcacaa ccggcacgga actcgctcgg    60
gctggccccg gtgcattttt taaatacccg cgagaaatag agttgatcgt caaaaccaac   120
attgcgaccg acggtggcga taggcatccg ggtggtgctc aaaagcagct tcgcctggct   180
gatacgttgg tcctcgcgcc agcttaagac gctaatccct aactgctggc ggaaaagatg   240
tgacagacgc gacggcgaca agcaaacatg ctgtgcgacg ctggcgatat caaaattgct   300
gtctgccagg tgatcgctga tgtactgaca agcctcgcgt acccgattat ccatcggtgg   360
atggagcgac tcgttaatcg cttccatgcg ccgcagtaac aattgctcaa gcagatttat   420
cgccagcagc tccgaatagc gcccttcccc ttgcccggcg ttaatgattt gcccaaacag   480
gtcgctgaaa tgcggctggt gcgcttcatc cgggcgaaag aaccccgtat tggcaaatat   540
tgacggccag ttaagccatt catgccagta ggcgcgcgga cgaaagtaaa cccactggtg   600
ataccattcg cgagcctccg gatgacgacc gtagtgatga atctctcctg gcgggaacag   660
caaaatatca cccggtcggc aaacaaattc tcgtccctga ttttcacca ccccctgacc   720 gcgaatggtg agattgagaa tataaccttt cattcccagc ggtcggtcga taaaaaaatc   780
gagataaccg ttggcctcaa tcggcgttaa acccgccacc agatgggcat aaacgagta   840 tcccggcagc aggggatcat tttgcgcttc agccat                            876

<210> SEQ ID NO 7
<211> LENGTH: 292
<212> TYPE: PRT
<213> ORGANISM: Artificial Sequence
<220> FEATURE:
<221> NAME/KEY: misc_feature
<222> LOCATION: (1)..(292)
<223> OTHER INFORMATION: araC on plasmid pBAD24-recET at 974-996

<400> SEQUENCE: 7

| | | | | | | | | | | | | | | |
|---|---|---|---|---|---|---|---|---|---|---|---|---|---|---|
| Met | Ala | Glu | Ala | Gln | Asn | Asp | Pro | Leu | Leu | Pro | Gly | Tyr | Ser | Phe | Asn |
| 1 | | | | 5 | | | | | 10 | | | | | 15 | |
| Ala | His | Leu | Val | Ala | Gly | Leu | Thr | Pro | Ile | Glu | Ala | Asn | Gly | Tyr | Leu |
| | | | 20 | | | | | 25 | | | | | 30 | | |
| Asp | Phe | Phe | Ile | Asp | Arg | Pro | Leu | Gly | Met | Lys | Gly | Tyr | Ile | Leu | Asn |
| | | 35 | | | | | 40 | | | | | 45 | | | |
| Leu | Thr | Ile | Arg | Gly | Gln | Gly | Val | Val | Lys | Asn | Gln | Gly | Arg | Glu | Phe |
| 50 | | | | | 55 | | | | | 60 | | | | | |
| Val | Cys | Arg | Pro | Gly | Asp | Ile | Leu | Leu | Phe | Pro | Pro | Gly | Glu | Ile | His |
| 65 | | | | 70 | | | | | 75 | | | | | 80 | |
| His | Tyr | Gly | Arg | His | Pro | Glu | Ala | Arg | Glu | Trp | Tyr | His | Gln | Trp | Val |
| | | | | 85 | | | | | 90 | | | | | 95 | |
| Tyr | Phe | Arg | Pro | Arg | Ala | Tyr | Trp | His | Glu | Trp | Leu | Asn | Trp | Pro | Ser |
| | | | 100 | | | | | 105 | | | | | 110 | | |
| Ile | Phe | Ala | Asn | Thr | Gly | Phe | Phe | Arg | Pro | Asp | Glu | Ala | His | Gln | Pro |
| | | | 115 | | | | | 120 | | | | | 125 | | |
| His | Phe | Ser | Asp | Leu | Phe | Gly | Gln | Ile | Ile | Asn | Ala | Gly | Gln | Gly | Glu |
| | | 130 | | | | | 135 | | | | | 140 | | | |
| Gly | Arg | Tyr | Ser | Glu | Leu | Leu | Ala | Ile | Asn | Leu | Leu | Glu | Gln | Leu | Leu |
| 145 | | | | | 150 | | | | | 155 | | | | | 160 |
| Leu | Arg | Arg | Met | Glu | Ala | Ile | Asn | Glu | Ser | Leu | His | Pro | Pro | Met | Asp |
| | | | | 165 | | | | | 170 | | | | | 175 | |
| Asn | Arg | Val | Arg | Glu | Ala | Cys | Gln | Tyr | Ile | Ser | Asp | His | Leu | Ala | Asp |
| | | | 180 | | | | | 185 | | | | | 190 | | |
| Ser | Asn | Phe | Asp | Ile | Ala | Ser | Val | Ala | Gln | His | Val | Cys | Leu | Ser | Pro |
| | | 195 | | | | | 200 | | | | | 205 | | | |
| Ser | Arg | Leu | Ser | His | Leu | Phe | Arg | Gln | Gln | Leu | Gly | Ile | Ser | Val | Leu |
| | 210 | | | | | 215 | | | | | 220 | | | | |
| Ser | Trp | Arg | Glu | Asp | Gln | Arg | Ile | Ser | Gln | Ala | Lys | Leu | Leu | Leu | Ser |
| 225 | | | | | 230 | | | | | 235 | | | | | 240 |
| Thr | Thr | Arg | Met | Pro | Ile | Ala | Thr | Val | Gly | Arg | Asn | Val | Gly | Phe | Asp |
| | | | | 245 | | | | | 250 | | | | | 255 | |
| Asp | Gln | Leu | Tyr | Phe | Ser | Arg | Val | Phe | Lys | Lys | Cys | Thr | Gly | Ala | Ser |
| | | | 260 | | | | | 265 | | | | | 270 | | |
| Pro | Ser | Glu | Phe | Arg | Ala | Gly | Cys | Glu | Glu | Lys | Val | Asn | Asp | Val | Ala |
| | | 275 | | | | | 280 | | | | | 285 | | | |
| Val | Lys | Leu | Ser |
| | 290 | | |

<210> SEQ ID NO 8
<211> LENGTH: 861
<212> TYPE: DNA
<213> ORGANISM: Artificial Sequence
<220> FEATURE:
<221> NAME/KEY: misc_feature
<222> LOCATION: (1)..(861)
<223> OTHER INFORMATION: bla gene on plasmid pBAD24-recET at 3493-4353
<220> FEATURE:
<221> NAME/KEY: CDS
<222> LOCATION: (1)..(861)
<223> OTHER INFORMATION: bla

<400> SEQUENCE: 8

| atg | agt | att | caa | cat | ttc | cgt | gtc | gcc | ctt | att | ccc | ttt | ttt | gcg | gca | 48 |
|---|---|---|---|---|---|---|---|---|---|---|---|---|---|---|---|---|
| Met | Ser | Ile | Gln | His | Phe | Arg | Val | Ala | Leu | Ile | Pro | Phe | Phe | Ala | Ala | |
| | 295 | | | | | 300 | | | | | 305 | | | | | |

| | | | | | | | | | | | | | | | | |
|---|---|---|---|---|---|---|---|---|---|---|---|---|---|---|---|---|
| ttt | tgc | ctt | cct | gtt | ttt | gct | cac | cca | gaa | acg | ctg | gtg | aaa | gta | aaa | 96 |
| Phe | Cys | Leu | Pro | Val | Phe | Ala | His | Pro | Glu | Thr | Leu | Val | Lys | Val | Lys | |
| 310 | | | | | 315 | | | | | 320 | | | | | | |
| gat | gct | gaa | gat | cag | ttg | ggt | gca | cga | gtg | ggt | tac | atc | gaa | ctg | gat | 144 |
| Asp | Ala | Glu | Asp | Gln | Leu | Gly | Ala | Arg | Val | Gly | Tyr | Ile | Glu | Leu | Asp | |
| 325 | | | | 330 | | | | | 335 | | | | | 340 | | |
| ctc | aac | agc | ggt | aag | atc | ctt | gag | agt | ttt | cgc | ccc | gaa | gaa | cgt | ttt | 192 |
| Leu | Asn | Ser | Gly | Lys | Ile | Leu | Glu | Ser | Phe | Arg | Pro | Glu | Glu | Arg | Phe | |
| | | | | 345 | | | | | 350 | | | | | 355 | | |
| cca | atg | atg | agc | act | ttt | aaa | gtt | ctg | cta | tgt | ggc | gcg | gta | tta | tcc | 240 |
| Pro | Met | Met | Ser | Thr | Phe | Lys | Val | Leu | Leu | Cys | Gly | Ala | Val | Leu | Ser | |
| | | | 360 | | | | | 365 | | | | | 370 | | | |
| cgt | gtt | gac | gcc | ggg | caa | gag | caa | ctc | ggt | cgc | cgc | ata | cac | tat | tct | 288 |
| Arg | Val | Asp | Ala | Gly | Gln | Glu | Gln | Leu | Gly | Arg | Arg | Ile | His | Tyr | Ser | |
| | | 375 | | | | | 380 | | | | | 385 | | | | |
| cag | aat | gac | ttg | gtt | gag | tac | tca | cca | gtc | aca | gaa | aag | cat | ctt | acg | 336 |
| Gln | Asn | Asp | Leu | Val | Glu | Tyr | Ser | Pro | Val | Thr | Glu | Lys | His | Leu | Thr | |
| | 390 | | | | | 395 | | | | | 400 | | | | | |
| gat | ggc | atg | aca | gta | aga | gaa | tta | tgc | agt | gct | gcc | ata | acc | atg | agt | 384 |
| Asp | Gly | Met | Thr | Val | Arg | Glu | Leu | Cys | Ser | Ala | Ala | Ile | Thr | Met | Ser | |
| 405 | | | | 410 | | | | | 415 | | | | | 420 | | |
| gat | aac | act | gcg | gcc | aac | tta | ctt | ctg | aca | acg | atc | gga | gga | ccg | aag | 432 |
| Asp | Asn | Thr | Ala | Ala | Asn | Leu | Leu | Leu | Thr | Thr | Ile | Gly | Gly | Pro | Lys | |
| | | | | 425 | | | | | 430 | | | | | 435 | | |
| gag | cta | acc | gct | ttt | ttg | cac | aac | atg | ggg | gat | cat | gta | act | cgc | ctt | 480 |
| Glu | Leu | Thr | Ala | Phe | Leu | His | Asn | Met | Gly | Asp | His | Val | Thr | Arg | Leu | |
| | | | | 440 | | | | | 445 | | | | | 450 | | |
| gat | cgt | tgg | gaa | ccg | gag | ctg | aat | gaa | gcc | ata | cca | aac | gac | gag | cgt | 528 |
| Asp | Arg | Trp | Glu | Pro | Glu | Leu | Asn | Glu | Ala | Ile | Pro | Asn | Asp | Glu | Arg | |
| | | 455 | | | | | 460 | | | | | 465 | | | | |
| gac | acc | acg | atg | cct | gta | gca | atg | gca | aca | acg | ttg | cgc | aaa | cta | tta | 576 |
| Asp | Thr | Thr | Met | Pro | Val | Ala | Met | Ala | Thr | Thr | Leu | Arg | Lys | Leu | Leu | |
| | 470 | | | | | 475 | | | | | 480 | | | | | |
| act | ggc | gaa | cta | ctt | act | cta | gct | tcc | cgg | caa | caa | tta | ata | gac | tgg | 624 |
| Thr | Gly | Glu | Leu | Leu | Thr | Leu | Ala | Ser | Arg | Gln | Gln | Leu | Ile | Asp | Trp | |
| 485 | | | | 490 | | | | | 495 | | | | | 500 | | |
| atg | gag | gcg | gat | aaa | gtt | gca | gga | cca | ctt | ctg | cgc | tcg | gcc | ctt | ccg | 672 |
| Met | Glu | Ala | Asp | Lys | Val | Ala | Gly | Pro | Leu | Leu | Arg | Ser | Ala | Leu | Pro | |
| | | | | 505 | | | | | 510 | | | | | 515 | | |
| gct | ggc | tgg | ttt | att | gct | gat | aaa | tct | gga | gcc | ggt | gag | cgt | ggg | tct | 720 |
| Ala | Gly | Trp | Phe | Ile | Ala | Asp | Lys | Ser | Gly | Ala | Gly | Glu | Arg | Gly | Ser | |
| | | | 520 | | | | | 525 | | | | | 530 | | | |
| cgc | ggt | atc | att | gca | gca | ctg | ggg | cca | gat | ggt | aag | ccc | tcc | cgt | atc | 768 |
| Arg | Gly | Ile | Ile | Ala | Ala | Leu | Gly | Pro | Asp | Gly | Lys | Pro | Ser | Arg | Ile | |
| | | 535 | | | | | 540 | | | | | 545 | | | | |
| gta | gtt | atc | tac | acg | acg | ggg | agt | cag | gca | act | atg | gat | gaa | cga | aat | 816 |
| Val | Val | Ile | Tyr | Thr | Thr | Gly | Ser | Gln | Ala | Thr | Met | Asp | Glu | Arg | Asn | |
| | 550 | | | | | 555 | | | | | 560 | | | | | |
| aga | cag | atc | gct | gag | ata | ggt | gcc | tca | ctg | att | aag | cat | tgg | taa | | 861 |
| Arg | Gln | Ile | Ala | Glu | Ile | Gly | Ala | Ser | Leu | Ile | Lys | His | Trp | * | | |
| 565 | | | | 570 | | | | | 575 | | | | | | | |

<210> SEQ ID NO 9
<211> LENGTH: 286
<212> TYPE: PRT
<213> ORGANISM: Artificial Sequence
<220> FEATURE:
<221> NAME/KEY: DOMAIN
<222> LOCATION: (1)..(286)
<223> OTHER INFORMATION: bla gene on plasmid pBAD24-recET at 3493-4353

<400> SEQUENCE: 9

| | | | | | | | | | | | | | | |
|---|---|---|---|---|---|---|---|---|---|---|---|---|---|---|
|Met|Ser|Ile|Gln|His|Phe|Arg|Val|Ala|Leu|Ile|Pro|Phe|Phe|Ala|Ala|
|1| | | |5| | | | |10| | | | |15|

Phe Cys Leu Pro Val Phe Ala His Pro Glu Thr Leu Val Lys Val Lys
                    20                    25                    30

Asp Ala Glu Asp Gln Leu Gly Ala Arg Val Gly Tyr Ile Glu Leu Asp
        35                    40                    45

Leu Asn Ser Gly Lys Ile Leu Glu Ser Phe Arg Pro Glu Glu Arg Phe
    50                    55                    60

Pro Met Met Ser Thr Phe Lys Val Leu Leu Cys Gly Ala Val Leu Ser
65                  70                    75                  80

Arg Val Asp Ala Gly Gln Glu Gln Leu Gly Arg Arg Ile His Tyr Ser
            85                    90                    95

Gln Asn Asp Leu Val Glu Tyr Ser Pro Val Thr Glu Lys His Leu Thr
            100                  105                110

Asp Gly Met Thr Val Arg Glu Leu Cys Ser Ala Ala Ile Thr Met Ser
        115                  120                  125

Asp Asn Thr Ala Ala Asn Leu Leu Leu Thr Thr Ile Gly Gly Pro Lys
130                   135                  140

Glu Leu Thr Ala Phe Leu His Asn Met Gly Asp His Val Thr Arg Leu
145                  150                  155                160

Asp Arg Trp Glu Pro Glu Leu Asn Glu Ala Ile Pro Asn Asp Glu Arg
                165                  170                175

Asp Thr Thr Met Pro Val Ala Met Ala Thr Thr Leu Arg Lys Leu Leu
            180                  185                190

Thr Gly Glu Leu Leu Thr Leu Ala Ser Arg Gln Gln Leu Ile Asp Trp
        195                  200                  205

Met Glu Ala Asp Lys Val Ala Gly Pro Leu Leu Arg Ser Ala Leu Pro
210                  215                  220

Ala Gly Trp Phe Ile Ala Asp Lys Ser Gly Ala Gly Glu Arg Gly Ser
225                  230                  235                240

Arg Gly Ile Ile Ala Ala Leu Gly Pro Asp Gly Lys Pro Ser Arg Ile
            245                  250                255

Val Val Ile Tyr Thr Thr Gly Ser Gln Ala Thr Met Asp Glu Arg Asn
         260                  265                270

Arg Gln Ile Ala Glu Ile Gly Ala Ser Leu Ile Lys His Trp
        275                  280                285

<210> SEQ ID NO 10
<211> LENGTH: 7195
<212> TYPE: DNA
<213> ORGANISM: Artificial Sequence
<220> FEATURE:
<221> NAME/KEY: misc_feature
<222> LOCATION: (1)..(7195)
<223> OTHER INFORMATION: plasmid pBAD-ET-gamma
<220> FEATURE:
<221> NAME/KEY: CDS
<222> LOCATION: (1)..(7195)
<223> OTHER INFORMATION: red gamma

<400> SEQUENCE: 10

```
atcgatgcat aatgtgcctg tcaaatggac gaagcaggga ttctgcaaac cctatgctac     60
tccgtcaagc cgtcaattgt ctgattcgtt accaattatg acaacttgac ggctacatca    120 ttcactttttt cttcacaacc ggcacggaac tcgctcgggc tggccccggt gcattttttta   180 aatacccgcg agaaatagag ttgatcgtca aaaccaacat gcgaccgac ggtggcgata    240
```

-continued

```
ggcatccggg tggtgctcaa aagcagcttc gcctggctga tacgttggtc ctcgcgccag      300
cttaagacgc taatccctaa ctgctggcgg aaaagatgtg acagacgcga cggcgacaag      360
caaacatgct gtgcgacgct ggcgatatca aaattgctgt ctgccaggtg atcgctgatg      420
tactgacaag cctcgcgtac ccgattatcc atcggtggat ggagcgactc gttaatcgct      480
tccatgcgcc gcagtaacaa ttgctcaagc agatttatcg ccagcagctc cgaatagcgc      540
ccttcccctt gcccggcgtt aatgatttgc ccaaacaggt cgctgaaatg cggctggtgc      600
gcttcatccg ggcgaaagaa ccccgtattg caaatattg acggccagtt aagccattca       660
tgccagtagg cgcgcggacg aaagtaaacc cactggtgat accattcgcg agcctccgga      720
tgacgaccgt agtgatgaat ctctcctggc gggaacagca aaatatcacc cggtcggcaa      780
acaaattctc gtccctgatt tttcaccacc ccctgaccgc gaatggtgag attgagaata      840
taacctttca ttcccagcgg tcggtcgata aaaaaatcga gataaccgtt ggcctcaatc      900
ggcgttaaac ccgccaccag atgggcatta acgagtatc ccggcagcag gggatcattt       960
tgcgcttcag ccatactttt catactcccg ccattcagag aagaaaccaa ttgtccatat     1020
tgcatcagac attgccgtca ctgcgtcttt tactggctct ctcgctaac caaaccggta      1080
accccgctta ttaaaagcat tctgtaacaa agcgggacca aagccatgac aaaaacgcgt     1140
aacaaaagtg tctataatca cggcagaaaa gtccacattg attatttgca cggcgtcaca     1200
cttttgctatg ccatagcatt tttatccata agattagcgg atcctacctg acgctttta    1260
tcgcaactct ctactgtttc tccatacccg tttttttggg ctagcaggag gaattcacca     1320
tggatcccgt aatcgtagaa gacatagagc caggtattta ttacggaatt tcgaatgaga     1380
attaccacgc gggtcccggt atcagtaagt ctcagctcga tgacattgct gatactccgg     1440
cactatattt gtggcgtaaa aatgcccccg tggacaccac aaagacaaaa acgctcgatt     1500
taggaactgc tttccactgc cgggtacttg aaccggaaga attcagtaac cgctttatcg     1560
tagcacctga atttaaccgc cgtacaaacg ccggaaaaga agaagagaaa gcgtttctga     1620
tggaatgcgc aagcacagga aaaacggtta tcactgcgga agaaggccgg aaaattgaac     1680
tcatgtatca aagcgttatg gctttgccgc tggggcaatg gcttgttgaa agcgccggac     1740
acgctgaatc atcaatttac tgggaagatc ctgaaacagg aattttgtgt cggtgccgtc     1800
cggacaaaat tatccctgaa tttcactgga tcatggacgt gaaaactacg gcggatattc     1860
aacgattcaa aaccgcttat tacgactacc gctatacgt tcaggatgca ttctacagtg      1920
acggttatga agcacagttt ggagtgcagc caactttcgt ttttctggtt gccagcacaa     1980
ctattgaatg cggacgttat ccggttgaaa ttttcatgat gggcgaagaa gcaaaactgg     2040
caggtcaaca ggaatatcac cgcaatctgc gaaccctgtc tgactgcctg aataccgatg     2100
aatggccagc tattaagaca ttatcactgc cccgctgggc taaggaatat gcaaatgact     2160
agatctcgag gtacccgagc acgtgttgac aattaatcat cggcatagta tatcggcata     2220
gtataatacg acaaggtgag gaactaaacc atggctaagc aaccaccaat cgcaaaagcc     2280
gatctgcaaa aaactcaggg aaaccgtgca ccagcagcag ttaaaaatag cgacgtgatt     2340
agttttatta accagccatc aatgaaagag caactggcag cagctcttcc acgccatatg     2400
acggctgaac gtatgatccg tatcgccacc acagaaattg taaagttcc ggcgttagga     2460
aactgtgaca ctatgagttt tgtcagtgcg atcgtacagt gttcacagct cggacttgag     2520
ccaggtagcg ccctcggtca tgcatattta ctgccttttg gtaataaaaa cgaaaagagc     2580
```

```
ggtaaaaaga acgttcagct aatcattggc tatcgcggca tgattgatct ggctcgccgt    2640
tctggtcaaa tcgccagcct gtcagcccgt gttgtccgtg aaggtgacga gtttagcttc    2700
gaatttggcc ttgatgaaaa gttaatacac cgcccgggag aaaacgaaga tgccccggtt    2760
acccacgtct atgctgtcgc aagactgaaa gacggaggta ctcagtttga agttatgacg    2820
cgcaaacaga ttgagctggt gcgcagcctg agtaaagctg gtaataacgg gccgtgggta    2880
actcactggg aagaaatggc aaagaaaacg gctattcgtc gcctgttcaa atatttgccc    2940
gtatcaattg agatccagcg tgcagtatca atggatgaaa aggaaccact gacaatcgat    3000
cctgcagatt cctctgtatt aaccggggaa tacagtgtaa tcgataattc agaggaatag    3060
atctaagctt cctgctgaac atcaaaggca agaaacatc tgttgtcaaa gacagcatcc    3120
ttgaacaagg acaattaaca gttaacaaat aaaaacgcaa agaaaatgc cgatatccta    3180 ttggcatttt ctttttatttc ttatcaacat aaggtgaat cccatacctc gagcttcacg    3240
ctgccgcaag cactcaggc gcaagggctg ctaaaaggaa gcggaacacg tagaaagcca    3300
gtccgcagaa acggtgctga ccccggatga atgtcagcta ctgggctatc tggacaaggg    3360
aaaacgcaag cgcaaagaga aagcaggtag cttgcagtgg gcttacatgg cgatagctag    3420
actgggcggt tttatggaca gcaagcgaac cggaattgcc agctggggcg ccctctggta    3480
aggttgggaa gccctgcaaa gtaaactgga tggctttctt gccgccaagg atctgatggc    3540 gcagggatc aagatctgat caagagacag gatgaggatc gtttcgcatg gatattaata    3600
ctgaaactga gatcaagcaa aagcattcac taaccccctt tcctgttttc ctaatcagcc    3660
cggcatttcg cggcgatat tttcacagct atttcaggag ttcagccatg aacgcttatt    3720
acattcagga tcgtcttgag gctcagagct gggcgcgtca ctaccagcag ctcgcccgtg    3780
aagagaaaga ggcagaactg gcagacgaca tggaaaaagg cctgccccag cacctgtttg    3840
aatcgctatg catcgatcat ttgcaacgcc acggggccag caaaaaatcc attacccgtg    3900
cgtttgatga cgatgttgag tttcaggagc gcatggcaga acacatccgg tacatggttg    3960
aaaccattgc tcaccaccag gttgatattg attcagaggt ataaaacgag tagaagcttg    4020
gctgttttgg cggatgagag aagattttca gcctgataca gattaaatca gaacgcagaa    4080
gcggtctgat aaaacagaat ttgcctggcg gcagtagcgc ggtggtccca cctgacccca    4140
tgccgaactc agaagtgaaa cgccgtagcg ccgatggtag tgtggggtct ccccatgcga    4200
gagtagggaa ctgccaggca tcaaataaaa cgaaaggctc agtcgaaaga ctgggccttt    4260
cgttttatct gttgtttgtc ggtgaacgct ctcctgagta ggacaaatcc gccgggagcg    4320
gatttgaacg ttgcgaagca acggcccgga gggtggcggg caggacgccc gccataaact    4380
gccaggcatc aaattaagca gaaggccatc ctgacggatg gccttttgc gtttctacaa    4440 actcttttgt ttattttct aaatacattc aaatatgtat ccgctcatga gacaataacc    4500
ctgataaatg cttcaataat attgaaaaag gaagagtatg agtattcaac atttccgtgt    4560
cgcccttatt ccctttttg cggcattttg ccttcctgtt tttgctcacc cagaaacgct    4620
ggtgaaagta aaagatgctg aagatcagtt gggtgcacga gtgggttaca tcgaactgga    4680
tctcaacagc ggtaagatcc ttgagagttt tcgccccgaa gaacgttttc caatgatgag    4740
cacttttaaa gttctgctat gtggcgcggt attatcccgt gttgacgccg ggcaagagca    4800
actcggtcgc cgcatacact attctcagaa tgacttggtt gagtactcac cagtcacaga    4860
aaagcatctt acggatggca tgacagtaag agaattatgc agtgctgcca taaccatgag    4920
tgataacact gcggccaact tacttctgac aacgatcgga ggaccgaagg agctaaccgc    4980
```

-continued

```
ttttttgcac aacatggggg atcatgtaac tcgccttgat cgttgggaac cggagctgaa    5040
tgaagccata ccaaacgacg agcgtgacac cacgatgcct gtagcaatgg caacaacgtt    5100
gcgcaaacta ttaactggcg aactacttac tctagcttcc cggcaacaat taatagactg    5160
gatggaggcg gataaagttg caggaccact tctgcgctcg gcccttccgg ctggctggtt    5220
tattgctgat aaatctggag ccggtgagcg tgggtctcgc ggtatcattg cagcactggg    5280
gccagatggt aagccctccc gtatcgtagt tatctacacg acggggagtc aggcaactat    5340
ggatgaacga atagacaga tcgctgagat aggtgcctca ctgattaagc attggtaact    5400
gtcagaccaa gtttactcat atatacttta gattgattta cgcgccctgt agcggcgcat    5460
taagcgcggc gggtgtggtg gttacgcgca gcgtgaccgc tacacttgcc agcgccctag    5520
cgcccgctcc tttcgctttc ttcccttcct ttctcgccac gttcgccggc tttccccgtc    5580
aagctctaaa tcggggctc cctttagggt tccgatttag tgctttacgg cacctcgacc    5640
ccaaaaaact tgatttgggt gatggttcac gtagtgggcc atcgccctga tagacggttt    5700
ttcgcccttt gacgttggag tccacgttct ttaatagtgg actcttgttc caaacttgaa    5760
caacactcaa ccctatctcg ggctattctt ttgatttata agggattttg ccgatttcgg    5820
cctattggtt aaaaaatgag ctgatttaac aaaaatttaa cgcgaatttt aacaaaatat    5880
taacgtttac aatttaaaag gatctaggtg aagatccttt ttgataatct catgaccaaa    5940
atcccttaac gtgagttttc gttccactga gcgtcagacc ccgtagaaaa gatcaaagga    6000
tcttcttgag atcctttttt tctgcgcgta atctgctgct tgcaaacaaa aaaaccaccg    6060
ctaccagcgg tggtttgttt gccggatcaa gagctaccaa ctcttttcc gaaggtaact    6120 ggcttcagca gagcgcagat accaaatact gtccttctag tgtagccgta gttaggccac    6180
cacttcaaga actctgtagc accgcctaca tacctcgctc tgctaatcct gttaccagtg    6240
gctgctgcca gtggcgataa gtcgtgtctt accgggttgg actcaagacg atagttaccg    6300
gataaggcgc agcggtcggg ctgaacgggg ggttcgtgca cacagcccag cttggagcga    6360
acgacctaca ccgaactgag atacctacag cgtgagctat gagaaagcgc cacgcttccc    6420
gaagggagaa aggcggacag gtatccggta agcggcaggg tcggaacagg agagcgcacg    6480
agggagcttc caggggggaaa cgcctggtat ctttatagtc ctgtcgggtt tcgccacctc    6540
tgacttgagc gtcgattttt gtgatgctcg tcagggggc ggagcctatg gaaaaacgcc    6600
agcaacgcgg cctttttacg gttcctggcc ttttgctggc cttttgctca catgttcttt    6660
cctgcgttat cccctgattc tgtggataac cgtattaccg cctttgagtg agctgatacc    6720
gctcgccgca gccgaacgac cgagcgcagc gagtcagtga cgaggaagc ggaagagcgc    6780 ctgatgcggt attttctcct tacgcatctg tgcggtattt cacaccgcat agggtcatgg    6840
ctgcgccccg acaccgcca acacccgctg acgcgccctg acgggcttgt ctgctcccgg    6900
catccgctta cagacaagct gtgaccgtct ccgggagctg catgtgtcag aggttttcac    6960
cgtcatcacc gaaacgcgcg aggcagcaag gagatggcgc ccaacagtcc cccggccacg    7020
gggcctgcca ccatacccac gccgaaacaa gcgctcatga gcccgaagtg gcgagcccga    7080
tcttccccat cggtgatgtc ggcgatatag gcgccagcaa ccgcacctgt ggcgccggtg    7140
atgccggcca cgatgcgtcc ggcgtagagg atctgctcat gtttgacagc ttatc         7195
```

<210> SEQ ID NO 11
<211> LENGTH: 7010
<212> TYPE: DNA

```
<213> ORGANISM: Artificial Sequence
<220> FEATURE:
<221> NAME/KEY: misc_feature
<222> LOCATION: (1)..(7010)
<223> OTHER INFORMATION: plasmid pBAD-alpha-beta-gamma
<220> FEATURE:
<221> NAME/KEY: CDS
<222> LOCATION: (1320)..(2000)
<223> OTHER INFORMATION: red alpha
<220> FEATURE:
<221> NAME/KEY: CDS
<222> LOCATION: (2086)..(2871)
<223> OTHER INFORMATION: red beta
<220> FEATURE:
<221> NAME/KEY: CDS
<222> LOCATION: (3403)..(3819)
<223> OTHER INFORMATION: red gamma

<400> SEQUENCE: 11
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcactttt cttcacaacc ggcacggaac tcgctcgggc tggccccggt gcattttta      180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gcccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattcgcg agcctccgga     720
tgacgaccgt agtgatgaat ctctcctggc gggaacagca aaatatcacc cggtcggcaa     780
acaaattctc gtccctgatt tttcaccacc ccctgaccgc gaatggtgag attgagaata     840
taacctttca ttcccagcgg tcggtcgata aaaaaatcga gataaccgtt ggcctcaatc     900
ggcgttaaac ccgccaccag atgggcatta acgagtatc ccggcagcag gggatcattt     960
tgcgcttcag ccatactttt catactcccg ccattcagag aagaaaccaa ttgtccatat    1020
tgcatcagac attgccgtca ctgcgtcttt tactggctct ctcgctaac caaaccggta    1080
accccgctta ttaaaagcat tctgtaacaa agcgggacca aagccatgac aaaaacgcgt    1140
aacaaaagtg tctataatca cggcagaaaa gtccacattg attatttgca cggcgtcaca    1200
ctttgctatg ccatagcatt tttatccata agattagcgg atcctacctg acgctttta    1260
tcgcaactct ctactgtttc tccatacccg ttttttggg ctagcaggag gaattcacc    1319 atg aca ccg gac att atc ctg cag cgt acc ggg atc gat gtg aga gct    1367
Met Thr Pro Asp Ile Ile Leu Gln Arg Thr Gly Ile Asp Val Arg Ala
    290                 295                 300 gtc gaa cag ggg gat gat gcg tgg cac aaa tta cgg ctc ggc gtc atc    1415
Val Glu Gln Gly Asp Asp Ala Trp His Lys Leu Arg Leu Gly Val Ile
        305                 310                 315 acc gct tca gaa gtt cac aac gtg ata gca aaa ccc cgc tcc gga aag    1463
Thr Ala Ser Glu Val His Asn Val Ile Ala Lys Pro Arg Ser Gly Lys
320                 325                 330                 335 aag tgg cct gac atg aaa atg tcc tac ttc cac acc ctg ctt gct gag    1511
Lys Trp Pro Asp Met Lys Met Ser Tyr Phe His Thr Leu Leu Ala Glu
                340                 345                 350
```

```
gtt tgc acc ggt gtg gct ccg gaa gtt aac gct aaa gca ctg gcc tgg      1559
Val Cys Thr Gly Val Ala Pro Glu Val Asn Ala Lys Ala Leu Ala Trp
        355                 360                 365 gga aaa cag tac gag aac gac gcc aga acc ctg ttt gaa ttc act tcc      1607
Gly Lys Gln Tyr Glu Asn Asp Ala Arg Thr Leu Phe Glu Phe Thr Ser
            370                 375                 380 ggc gtg aat gtt act gaa tcc ccg atc atc tat cgc gac gaa agt atg      1655
Gly Val Asn Val Thr Glu Ser Pro Ile Ile Tyr Arg Asp Glu Ser Met
385                 390                 395 cgt acc gcc tgc tct ccc gat ggt tta tgc agt gac ggc aac ggc ctt      1703
Arg Thr Ala Cys Ser Pro Asp Gly Leu Cys Ser Asp Gly Asn Gly Leu
400                 405                 410                 415 gaa ctg aaa tgc ccg ttt acc tcc cgg gat ttc atg aag ttc cgg ctc      1751
Glu Leu Lys Cys Pro Phe Thr Ser Arg Asp Phe Met Lys Phe Arg Leu
                420                 425                 430 ggt ggt ttc gag gcc ata aag tca gct tac atg gcc cag gtg cag tac      1799
Gly Gly Phe Glu Ala Ile Lys Ser Ala Tyr Met Ala Gln Val Gln Tyr
            435                 440                 445 agc atg tgg gtg acg cga aaa aat gcc tgg tac ttt gcc aac tat gac      1847
Ser Met Trp Val Thr Arg Lys Asn Ala Trp Tyr Phe Ala Asn Tyr Asp
        450                 455                 460 ccg cgt atg aag cgt gaa ggc ctg cat tat gtc gtg att gag cgg gat      1895
Pro Arg Met Lys Arg Glu Gly Leu His Tyr Val Val Ile Glu Arg Asp
465                 470                 475 gaa aag tac atg gcg agt ttt gac gag atc gtg ccg gag ttc atc gaa      1943
Glu Lys Tyr Met Ala Ser Phe Asp Glu Ile Val Pro Glu Phe Ile Glu
480                 485                 490                 495 aaa atg gac gag gca ctg gct gaa att ggt ttt gta ttt ggg gag caa      1991
Lys Met Asp Glu Ala Leu Ala Glu Ile Gly Phe Val Phe Gly Glu Gln
                500                 505                 510 tgg cga tag atccggtacc cgagcacgtg ttgacaatta atcatcggca             2040
Trp Arg * tagtatatcg gcatagtata atacgacaag gtgaggaact aaacc atg agt act      2094
                                                  Met Ser Thr
                                                      1 gca ctc gca acg ctg gct ggg aag ctg gct gaa cgt gtc ggc atg gat     2142
Ala Leu Ala Thr Leu Ala Gly Lys Leu Ala Glu Arg Val Gly Met Asp
    5                   10                  15 tct gtc gac cca cag gaa ctg atc acc act ctt cgc cag acg gca ttt    2190
Ser Val Asp Pro Gln Glu Leu Ile Thr Thr Leu Arg Gln Thr Ala Phe
20                  25                  30                  35 aaa ggt gat gcc agc gat gcg cag ttc atc gca tta ctg atc gtt gcc    2238
Lys Gly Asp Ala Ser Asp Ala Gln Phe Ile Ala Leu Leu Ile Val Ala
                40                  45                  50 aac cag tac ggc ctt aat ccg tgg acg aaa gaa att tac gcc ttt cct    2286
Asn Gln Tyr Gly Leu Asn Pro Trp Thr Lys Glu Ile Tyr Ala Phe Pro
            55                  60                  65 gat aag cag aat ggc atc gtt ccg gtg gtg ggc gtt gat ggc tgg tcc    2334
Asp Lys Gln Asn Gly Ile Val Pro Val Val Gly Val Asp Gly Trp Ser
        70                  75                  80 cgc atc atc aat gaa aac cag cag ttt gat ggc atg gac ttt gag cag    2382
Arg Ile Ile Asn Glu Asn Gln Gln Phe Asp Gly Met Asp Phe Glu Gln
85                  90                  95 gac aat gaa tcc tgt aca tgc cgg att tac cgc aag gac cgt aat cat    2430
Asp Asn Glu Ser Cys Thr Cys Arg Ile Tyr Arg Lys Asp Arg Asn His
100                 105                 110                 115 ccg atc tgc gtt acc gaa tgg atg gat gaa tgc cgc cgc gaa cca ttc    2478
Pro Ile Cys Val Thr Glu Trp Met Asp Glu Cys Arg Arg Glu Pro Phe
                120                 125                 130
```

-continued

```
aaa act cgc gaa ggc aga gaa atc acg ggg ccg tgg cag tcg cat ccc      2526
Lys Thr Arg Glu Gly Arg Glu Ile Thr Gly Pro Trp Gln Ser His Pro
        135                 140                 145 aaa cgg atg tta cgt cat aaa gcc atg att cag tgt gcc cgt ctg gcc      2574
Lys Arg Met Leu Arg His Lys Ala Met Ile Gln Cys Ala Arg Leu Ala
    150                 155                 160 ttc gga ttt gct ggt atc tat gac aag gat gaa gcc gag cgc att gtc      2622
Phe Gly Phe Ala Gly Ile Tyr Asp Lys Asp Glu Ala Glu Arg Ile Val
165                 170                 175 gaa aat act gca tac act gca gaa cgt cag ccg gaa cgc gac atc act      2670
Glu Asn Thr Ala Tyr Thr Ala Glu Arg Gln Pro Glu Arg Asp Ile Thr
180                 185                 190                 195 ccg gtt aac gat gaa acc atg cag gag att aac act ctg ctg atc gcc      2718
Pro Val Asn Asp Glu Thr Met Gln Glu Ile Asn Thr Leu Leu Ile Ala
                200                 205                 210 ctg gat aaa aca tgg gat gac gac tta ttg ccg ctc tgt tcc cag ata      2766
Leu Asp Lys Thr Trp Asp Asp Asp Leu Leu Pro Leu Cys Ser Gln Ile
            215                 220                 225 ttt cgc cgc gac att cgt gca tcg tca gaa ctg aca cag gcc gaa gca      2814
Phe Arg Arg Asp Ile Arg Ala Ser Ser Glu Leu Thr Gln Ala Glu Ala
        230                 235                 240 gta aaa gct ctt gga ttc ctg aaa cag aaa gcc gca gag cag aag gtg      2862
Val Lys Ala Leu Gly Phe Leu Lys Gln Lys Ala Ala Glu Gln Lys Val
    245                 250                 255 gca gca tag atctcgagaa gcttcctgct gaacatcaaa ggcaagaaaa               2911
Ala Ala  *
260 catctgttgt caaagacagc atccttgaac aaggacaatt aacagttaac aaataaaaac    2971 gcaaagaaa atgccgatat cctattggca ttttctttta tttcttatca acataaaggt    3031 gaatcccata cctcgagctt cacgctgccg caagcactca gggcgcaagg gctgctaaaa   3091 ggaagcggaa cacgtagaaa gccagtccgc agaaacggtg ctgaccccgg atgaatgtca   3151 gctactgggc tatctggaca agggaaaacg caagcgcaaa gagaaagcag gtagcttgca   3211 gtgggcttac atggcgatag ctagactggg cggttttatg gacagcaagc gaaccggaat   3271 tgccagctgg ggcgccctct ggtaaggttg ggaagccctg caaagtaaac tggatggctt   3331 tcttgccgcc aaggatctga tggcgcaggg atcaagatc tgatcaagag acaggatgag    3391 gatcgtttcg c atg gat att aat act gaa act gag atc aag caa aag cat    3441
          Met Asp Ile Asn Thr Glu Thr Glu Ile Lys Gln Lys His
            1               5                  10 tca cta acc ccc ttt cct gtt ttc cta atc agc ccg gca ttt cgc ggg     3489
Ser Leu Thr Pro Phe Pro Val Phe Leu Ile Ser Pro Ala Phe Arg Gly
 15              20                  25 cga tat ttt cac agc tat ttc agg agt tca gcc atg aac gct tat tac     3537
Arg Tyr Phe His Ser Tyr Phe Arg Ser Ser Ala Met Asn Ala Tyr Tyr
30              35                  40                  45 att cag gat cgt ctt gag gct cag agc tgg gcg cgt cac tac cag cag     3585
Ile Gln Asp Arg Leu Glu Ala Gln Ser Trp Ala Arg His Tyr Gln Gln
            50                  55                  60 ctc gcc cgt gaa gag aaa gag gca gaa ctg gca gac gac atg gaa aaa     3633
Leu Ala Arg Glu Glu Lys Glu Ala Glu Leu Ala Asp Asp Met Glu Lys
        65                  70                  75 ggc ctg ccc cag cac ctg ttt gaa tcg cta tgc atc gat cat ttg caa     3681
Gly Leu Pro Gln His Leu Phe Glu Ser Leu Cys Ile Asp His Leu Gln
    80                  85                  90 cgc cac ggg gcc agc aaa aaa tcc att acc cgt gcg ttt gat gac gat     3729
Arg His Gly Ala Ser Lys Lys Ser Ile Thr Arg Ala Phe Asp Asp Asp
```

-continued

```
                  95                  100                 105
gtt gag ttt cag gag cgc atg gca gaa cac atc cgg tac atg gtt gaa       3777
Val Glu Phe Gln Glu Arg Met Ala Glu His Ile Arg Tyr Met Val Glu
110             115                 120                 125 acc att gct cac cac cag gtt gat att gat tca gag gta taa               3819
Thr Ile Ala His His Gln Val Asp Ile Asp Ser Glu Val  *
                130                 135 aacgagtaga agcttggctg ttttggcgga tgagagaaga ttttcagcct gatacagatt     3879
aaatcagaac gcagaagcgg tctgataaaa cagaatttgc ctggcggcag tagcgcggtg     3939
gtcccacctg accccatgcc gaactcagaa gtgaaacgcc gtagcgccga tggtagtgtg     3999
gggtctcccc atgcgagagt agggaactgc caggcatcaa ataaaacgaa aggctcagtc     4059
gaaagactgg gcctttcgtt ttatctgttg tttgtcggtg aacgctctcc tgagtaggac     4119
aaatccgccg ggagcggatt tgaacgttgc gaagcaacgg cccggagggt ggcgggcagg     4179
acgcccgcca taaactgcca ggcatcaaat taagcagaag gccatcctga cggatggcct     4239
ttttgcgttt ctacaaactc ttttgtttat ttttctaaat acattcaaat atgtatccgc     4299
tcatgagaca ataaccctga taaatgcttc aataatattg aaaaggaag agtatgagta      4359
ttcaacattt ccgtgtcgcc cttattccct tttttgcggc attttgcctt cctgtttttg     4419
ctcacccaga aacgctggtg aaagtaaaag atgctgaaga tcagttgggt gcacgagtgg     4479
gttacatcga actggatctc aacagcggta agatccttga gttttcgc cccgaagaac       4539
gttttccaat gatgagcact tttaaagttc tgctatgtgg cgcggtatta tcccgtgttg     4599
acgccgggca agagcaactc ggtcgccgca tacactattc tcagaatgac ttggttgagt     4659
actcaccagt cacagaaaag catcttacgg atggcatgac agtaagagaa ttatgcagtg     4719
ctgccataac catgagtgat aacactgcgg ccaacttact tctgacaacg atcggaggac     4779
cgaaggagct aaccgctttt tgcacaaca tgggggatca tgtaactcgc cttgatcgtt      4839
gggaaccgga gctgaatgaa gccataccaa acgacgagcg tgacaccacg atgcctgtag     4899
caatggcaac aacgttgcgc aaactattaa ctggcgaact acttactcta gcttcccggc     4959
aacaattaat agactggatg gaggcggata agttgcagg accacttctg cgctcggccc      5019
ttccggctgg ctggtttatt gctgataaat ctggagccgg tgagcgtggg tctcgcggta     5079
tcattgcagc actgggccca gatggtaagc cctcccgtat cgtagttatc tacacgacgg     5139
ggagtcaggc aactatggat gaacgaaata gacagatcgc tgagataggt gcctcactga     5199
ttaagcattg gtaactgtca gaccaagttt actcatatat actttagatt gatttacgcg     5259
ccctgtagcg gcgcattaag cgcggcgggt gtggtggtta cgcgcagcgt gaccgctaca     5319
cttgccagcg ccctagcgcc cgctcctttc gctttcttcc cttcctttct cgccacgttc     5379
gccggctttc cccgtcaagc tctaaatcgg gggctccctt tagggttccg atttagtgct     5439
ttacggcacc tcgaccccaa aaaacttgat tgggtgatg gttcacgtag tgggccatcg      5499
ccctgataga cggtttttcg ccctttgacg ttggagtcca cgttctttaa tagtggactc     5559
ttgttccaaa cttgaacaac actcaaccct atctcgggct attcttttga tttataaggg     5619
attttgccga tttcggccta ttggttaaaa atgagctga tttaacaaaa atttaacgcg      5679
aattttaaca aaatattaac gtttacaatt taaaggatc taggtgaaga tccttttga      5739
taatctcatg accaaaatcc cttaacgtga gttttcgttc cactgagcgt cagacccgt      5799
agaaaagatc aaaggatctt cttgagatcc ttttttctg cgcgtaatct gctgcttgca      5859
aacaaaaaaa ccaccgctac cagcggtggt ttgtttgccg gatcaagagc taccaactct     5919
```

-continued

```
ttttccgaag gtaactggct tcagcagagc gcagatacca aatactgtcc ttctagtgta      5979
gccgtagtta ggccaccact tcaagaactc tgtagcaccg cctacatacc tcgctctgct      6039
aatcctgtta ccagtggctg ctgccagtgg cgataagtcg tgtcttaccg ggttggactc      6099
aagacgatag ttaccggata aggcgcagcg gtcgggctga acgggggtt cgtgcacaca       6159 gcccagcttg gagcgaacga cctacaccga actgagatac ctacagcgtg agctatgaga      6219
aagcgccacg cttcccgaag ggagaaaggc ggacaggtat ccggtaagcg caggtcgg        6279 aacaggagag cgcacgaggg agcttccagg gggaaacgcc tggtatcttt atagtcctgt      6339
cgggtttcgc cacctctgac ttgagcgtcg attttgtga tgctcgtcag gggggcggag       6399
cctatggaaa aacgccagca acgcggcctt tttacggttc ctggccttt gctggccttt      6459 tgctcacatg ttctttcctg cgttatcccc tgattctgtg gataaccgta ttaccgcctt     6519
tgagtgagct gataccgctc gccgcagccg aacgaccgag cgcagcgagt cagtgagcga     6579
ggaagcggaa gagcgcctga tgcggtattt tctccttacg catctgtgcg gtatttcaca     6639 ccgcatagg tcatggctgc gcccgacac ccgccaacac ccgctgacgc gccctgacgg       6699
gcttgtctgc tcccggcatc cgcttacaga caagctgtga ccgtctccgg gagctgcatg     6759
tgtcagaggt tttcaccgtc atcaccgaaa cgcgcgaggc agcaaggaga tggcgcccaa     6819
cagtcccccg gccacggggc ctgccaccat acccacgccg aaacaagcgc tcatgagccc     6879
gaagtggcga gccgatctt ccccatcggt gatgtcggcg atataggcgc cagcaaccgc      6939
acctgtggcg ccggtgatgc cggccacgat gcgtccggcg tagaggatct gctcatgttt     6999
gacagcttat c                                                           7010
```

<210> SEQ ID NO 12  
<211> LENGTH: 226  
<212> TYPE: PRT  
<213> ORGANISM: Artificial Sequence  
<220> FEATURE:  
<221> NAME/KEY: DOMAIN  
<222> LOCATION: (1)..(226)  
<223> OTHER INFORMATION: Red-alpha from plasmid pBAD-alpha-beta-gamma

<400> SEQUENCE: 12

```
Met Thr Pro Asp Ile Ile Leu Gln Arg Thr Gly Ile Asp Val Arg Ala
 1               5                  10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
```

-continued

```
             145                 150                 155                 160
Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 13
<211> LENGTH: 261
<212> TYPE: PRT
<213> ORGANISM: Artificial Sequence
<220> FEATURE:
<221> NAME/KEY: DOMAIN
<222> LOCATION: (1)..(261)
<223> OTHER INFORMATION: Red-beta from plasmid pBAD-alpha-beta-gamma

<400> SEQUENCE: 13

Met Ser Thr Ala Leu Ala Thr Leu Ala Gly Lys Leu Ala Glu Arg Val
  1               5                  10                  15

Gly Met Asp Ser Val Asp Pro Gln Glu Leu Ile Thr Thr Leu Arg Gln
                 20                  25                  30

Thr Ala Phe Lys Gly Asp Ala Ser Asp Ala Gln Phe Ile Ala Leu Leu
            35                  40                  45

Ile Val Ala Asn Gln Tyr Gly Leu Asn Pro Trp Thr Lys Glu Ile Tyr
        50                  55                  60

Ala Phe Pro Asp Lys Gln Asn Gly Ile Val Pro Val Val Gly Val Asp
 65                  70                  75                  80

Gly Trp Ser Arg Ile Ile Asn Glu Asn Gln Gln Phe Asp Gly Met Asp
                 85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
        195                 200                 205

Leu Ile Ala Leu Asp Lys Thr Trp Asp Asp Asp Leu Leu Pro Leu Cys
    210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
                245                 250                 255

Gln Lys Val Ala Ala
            260
```

-continued

```
<210> SEQ ID NO 14
<211> LENGTH: 138
<212> TYPE: PRT
<213> ORGANISM: Artificial Sequence
<220> FEATURE:
<221> NAME/KEY: DOMAIN
<222> LOCATION: (1)..(138)
<223> OTHER INFORMATION: Red-gamma from plasmid pBAD-alpha-beta-gamma
      and plasmid pBAD-ET-gamma

<400> SEQUENCE: 14

Met Asp Ile Asn Thr Glu Thr Glu Ile Lys Gln Lys His Ser Leu Thr
 1               5                  10                  15

Pro Phe Pro Val Phe Leu Ile Ser Pro Ala Phe Arg Gly Arg Tyr Phe
                20                  25                  30

His Ser Tyr Phe Arg Ser Ser Ala Met Asn Ala Tyr Tyr Ile Gln Asp
             35                  40                  45

Arg Leu Glu Ala Gln Ser Trp Ala Arg His Tyr Gln Gln Leu Ala Arg
     50                  55                  60

Glu Glu Lys Glu Ala Glu Leu Ala Asp Asp Met Glu Lys Gly Leu Pro
 65                  70                  75                  80

Gln His Leu Phe Glu Ser Leu Cys Ile Asp His Leu Gln Arg His Gly
                 85                  90                  95

Ala Ser Lys Lys Ser Ile Thr Arg Ala Phe Asp Asp Asp Val Glu Phe
                100                 105                 110

Gln Glu Arg Met Ala Glu His Ile Arg Tyr Met Val Glu Thr Ile Ala
            115                 120                 125

His His Gln Val Asp Ile Asp Ser Glu Val
        130                 135
```